US006960617B2

(12) United States Patent
Omidian et al.

(10) Patent No.: US 6,960,617 B2
(45) Date of Patent: Nov. 1, 2005

(54) HYDROGELS HAVING ENHANCED ELASTICITY AND MECHANICAL STRENGTH PROPERTIES

(75) Inventors: Hossein Omidian, Sunrise, FL (US); Yong Qiu, Fremont, CA (US); Shicheng Yang, Hollywood, FL (US); Dukjoon Kim, Seoul (KR); Haesun Park, West Lafayette, IN (US); Kinam Park, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 76 days.

(21) Appl. No.: 10/420,323

(22) Filed: Apr. 22, 2003

(65) Prior Publication Data

US 2003/0232895 A1 Dec. 18, 2003

Related U.S. Application Data

(60) Provisional application No. 60/374,388, filed on Apr. 22, 2002.

(51) Int. Cl.$^7$ ................................................. C08F 36/04
(52) U.S. Cl. .................... 521/102; 521/109.1; 521/142; 521/146; 521/149; 521/182; 521/183; 521/186; 521/187; 521/84.1
(58) Field of Search ................................. 521/142, 146, 521/149, 182, 183, 186, 187, 84.1, 102, 109.1

(56) References Cited

U.S. PATENT DOCUMENTS

| | | |
|---|---|---|
| 4,421,824 A | 12/1983 | Gupta et al. |
| 4,814,179 A | 3/1989 | Bolton et al. |
| 5,232,704 A | 8/1993 | Franz et al. |
| 5,264,082 A | 11/1993 | Phan et al. |
| 5,718,916 A | 2/1998 | Scherr |
| 5,750,585 A | 5/1998 | Park et al. |
| 6,143,132 A | 11/2000 | Traubel et al. |
| 6,271,278 B1 | 8/2001 | Park et al. |

OTHER PUBLICATIONS

Park H., and Park K.: Hydrogel foams: A new type of fast swelling hydrogels Transactions of Society of Biomaterials 17: 158, 1994.
Chen J., Park H., and Park K.: Synthesis of superporous hydrogels: Hydrogels with fast swelling and superabsorbent properties, Journal of Biomedical Materials Research 44:53–62. 1999.
Patel V.R., A.M.M.: Preparation and characterization of freeze–dried chitosan—poly(ethylene oxide) hydrogels for site–specific antibiotic delivery in the stomach, Pharmaceutical Research 13: 588–593, 1996.
Oxley H.R., Corkhill P.H., Fitton J.H., and Tighe B.J.: Macroporous hydrogels for biomedical applications: Methods and morphology, Biomaterials 14: 1064–1072, 1993.
Kon M., d.V.A.C.: A poly(hema) sponge for restoration of articular cartilage defects, Plastic and Reconstructive Surgery 67:288–294, 1981.

Badiger M.V., McNeil M.E., and Graham N.B.: Progens in the preparation of microporous hydrogels based on poly–(ethylene oxide), Biomaterials 14: 1059–1063, 1993.
Bennett D.J., Burford R.P., Davis T.P., and Tilley H.J.: Synthesis of porous hydrogel structure by polymerizing the continuous phase of a microemulsion, Polymer International 36: 219–226. 1995.
Chirila T.V., Constable I.J., Crowford J., Vijaysekaran S., Thompson D.E., Chen Y.C., and Fletcher W.A.: Poly(2–hydroxyethyl methacrylate) sponges as implant materials: In vivo and in vitro evaluation of celluar invasion, Biomaterials 14, 26–36: 1994.
Khemani K.C: Polymeric foams: Science and technology, ACS Symposium Series, American Chemical Society, Washington DC 239: 1997.
Klempner D., and Frisch K.C.: Handbook of polymeric foams and foam technology, Hanser Publishers, Munich, 1991.
Spaans C.J.: Solvent–free fabrication of micro–porous polyurethane amide and polyurethane–urea scaffolds for repair and replacement of the knee–joint meniscus, Biomaterials 21: 2453–2460, 2000.
Elema H., deGroot J. H., and Nijenhuis A.J.: Use of porous biodegradable polymer implants in meniscus reconstruction. 2)biological evaluation of porous biodegradable polymer implants in menisci, Colloid Polymer Science 268: 1082–88, 1990.
de Groot J.H.: Use of porous biodegradable polymer implants in meniscus reconstruction. 1)preparation of porous biodegradable polyurethanes for the reconstruction of the meniscus, Colloid Polymer Science 268: 1073–81, 1990.
de Groot J. H., Zijlstra F. M., and Kuijpers H. W.: Meniscal tissue regeneration in porous 50/50 copoly(l–lactide/caprolactone) implants, Biomaterials 18: 613–22, 1997.
Kim B.S., and Mooney D. J.: Development of biocompatible synthetic extracellular matrices for tissue engineering, TIBTECH 16: 224–230, 1998.

(Continued)

Primary Examiner—James J. Seidleck
Assistant Examiner—Irina S. Zemel
(74) Attorney, Agent, or Firm—James H. Meadows; Medicus Associates

(57) ABSTRACT

Hydrogels having improved elasticity and mechanical strength properties are obtained by subjecting a hydrogel formulation containing a strengthening agent to chemical or physical crosslinking conditions subsequent to initial gel formation. Superporous hydrogels having improved elasticity and mechanical strength properties are similarly obtained whenever the hydrogel formulation is provided with a foaming agent. Interpenetrating networks of polymer chains comprised of primary polymer(s) and strengthening polymer (s) are thereby formed. The primary polymer affords capillary-based water sorption properties while the strengthening polymer imparts significantly enhanced mechanical strength and elasticity to the hydrogel or superporous hydrogel. Suitable strengthening agents can be natural or synthetic polymers, polyelectrolytes, or neutral, hydrophilic polymers.

28 Claims, 4 Drawing Sheets

OTHER PUBLICATIONS

Griffith L. G.: Polymeric biomaterials, Acta Materialia 48: 263–277, 2000.

Kang H. W., Tabata Y., and Ikada Y.: Fabrication of porous gelatin scaffolds for tissue engineering, Biomaterials 20: 1339–1344, 1999.

Bryant S. J., and Anseth K. S.: The effect of scaffold thickness on tissue engineered cartilage in photocrosslinked poly(ethylene oxide) hydrogels, Biomaterials 22: 619–626, 2001.

Park K., and Omidian H.: Experimental design in the synthesis of polyacrylamide superporous hydrogels, J. of Bioactive and Compatible Polymers, vol. 17(6), 2002.

Glicksman M.: Gum technology in the food industry, Academic Press, 163, 1969.

Gombotz W. R., and Wee SF.: Protein release from alginate matrices, Advanced Drug Delivery Reviews 31: 267–285, 1998.

Kuo C.K., and M P. X.: Ionically crosslinked alginate hydrogels as scaffolds for tissue engineering: Part 1. Structure, gelation rate and mechanical properties, Biomaterials 22: 511–521, 2001.

Eiselt P., Yeh J., Latvala R. K., Shea L.D., and Mooney D. J.: Porous carriers for biomedical applications based on alginate hydrogels, Biomaterials 21: 1921–1927, 2000.

Shapiro L., and Cohen S.: Novel alginate sponges for cell culture and transplantation, Biomaterials 18: 583–590, 1997.

Vorlop K. D., Steinert H. J., and Klein J.: Cell immobilization within coated alginate beads or hollow fibers by ionotropic gelation, Annals of the New York Academy of Sciences 501: 339–342, 1987.

Hills B. P., Godward J., Debatty M., Barras L., Saturio C. P., and Ouwerx C.: Nmr studies of calcium induced alginate gelation. Part ii. The internal bead structure, Magnetic Resonance in Chemistry 38 719–728, 2000.

Duez J. M., Mestdagh M., Demeure R., Goudemant J. F., Hills B. P., and Godward J.: Nmr studies of calcium–induced alginate gelation. Part 1–mri tests of gelation models, Magnetic Resonance in Chemistry 38: 324–330, 2000.

LeRoux M. A., Guilak F., and Setton L. A.: Compressive and shear properties of alginate gel: Effects of sodium ions and alginate concentration, Journal of Biomedical Materials Research 47: 46–53, 1999.

Kulkarni A. R., Soppimath K. S., and Aminabhavi T. M.: Controlled release of diclofenac sodium from sodium alginate beads crosslinked with glutaraldehyde, Pharmaceuica Acta Helvetiae 74:29–36, 1999.

Ostberg T., Vesterhus L., and Graffner C.: Calcium alginate matrices for oral multiple–unit administration. 2. Effect of process and formulation factors on matrix properties, International Journal of Pharmaceutics 97: 183–193, 1993.

Pillay V.: Drug release modualation from cross–linked calcium alginate microdiscs, 2:Swelling, compression, and stability of the hydrodynamically–sensitive calcium alginate matrix and the associated drug release mechanisms, Drug Delivery 5: 35–46, 1998.

Pillay V., Dangor C. M., Govender T., Moopanar K. R., and Hurbans N.: Ionotropic gelation: Encapsulation of indomethacin in calcium alginate gel discs, Journal of Microencapsulation 15: 215–226, 1998.

Pillay V., and Fassihi R.: In vitro release modulation from crosslinked pellets for site–specific drug delivery to the gastrointestinal tract —i. Comparison of ph–responsive drug release and associated kinetics, Journal of Controlled Release 59: 229–242, 1999.

Kulkarni A. R., Soppimath K. S., Aminbahavi T. M., Dave A. M., and Mehta M. H.: Glutaraldehyde crosslinked sodium alginate beads containing liquid pesticide for soil application, Journal of Controlled Release 63: 97–105, 2000.

Kim Y. J., Yoon K. J., and Ko S. W.: Preparation and properties of alginate superabsorbent filament fibers crosslinked with glutaraldehyde, Journal of Applied Polymer Science 78: 1797–1804, 2000.

Tripathy T., Pandey S. R., Karmakar N. C. Bhagat R. P., and Singh R. P.: Novel flocculating agent based on sodium alginate and acrylamide, European Polymer Journal 35: 2057–2072, 1999.

Kim S. R., Yuk S. H., and Jhon M. S.: A semi–interpenetrating network system for a polymer membrane, European Polymer Journal 33: 1009–1014, 1997.

Wang X. P.: Preparation of crosslinked alginate composite membrane for dehydration of ethanol–water mixtures, Journal of Applied Polymer Science 77: 3054–3061, 2000.

Hertzberg S., Moen E., Vogelsang C., and Ostgaard K.: Mixed photo–crosslinked poly(vinyl alcohol) and calcium–alginate gels for cell entrapment, Applied Microbiology and Biotechnology 43: 10–17, 1995.

Omidian H.: Elastic Superporous Hydrogels, Purdue University, Industrial and Physical Pharmacy, Research Report, 2001.

Shu X., and Zhu K. J.: A novel approach to prepare tripolyphosphate/chitosan complex beads for controlled release drug delivery , International Journal of Pharmaceutics 201: 51–58, 2000.

Kumar M. N. V. R.: A review of chitin and chitisan applications, Reactive, Reactive & Functional Polymers 46: 1–27, 2000.

Lee S. T., Mi F. L., Shen Y.J., and Shyu S.S.: Equilibrium and kinetic studies of cooper (ii) ion uptake by chitosan–t–ripolyphosphate chelating resin, Polymer 42:1879–1892, 2001.

Aral C., and Akbuga J.: Alternative approach to the preparation of chitosan beads, International Journal of Pharmaceutics 168: 9–15, 1998.

Aydin Z., and Akbuga J.: Chitosan beads for the delivery of salmon calcitonin: Preparation and release characteristics, International Journal of Pharmaceutics 131: 101–103, 1996.

Dureja H., Tiwary A. K., and Gupta S.: Simulation of skin permeability in chitosan membranes, International Journal of Pharmaceutics 213: 193–198, 2001.

Shu X. Z., and Zhu K. J.:Chitosan/gelatin microspheres prepared by modified emulsification and iontropic gelation, Journal of Microencapsulation 18: 237–245, 2001.

Lim L. Y., Wan L. S. C., and Thai P. Y.: Chitosan microspheres prepared by emulsification and iontropic gelation, Drug Development and Industrial Pharmacy 23:981–985, 1997.

Long D. D., and vanLuyen D.: Chitosan–carboxymethylcellulose hydrogels as supports for cell immobilization, Journal of Macromolecular Science–Pure and Applied Chemistry A33: 1875–1884, 1996.

Mi F. L., Shyu S. S., Lee S. T., and Wong T. B.: Kinetic study of chitosan–tripolyphosphate complex reaction and acid–resistive properties of the chitosan–tripolyphosphate gel beads prepared by in–liquid curing method, Journal of.

Overgaard S., Scharer J. M., Mooyoung M., and Bols N. C.: Immobilization of hybridoma cells in chitosan alginate beads, Canadian Journal of Chemical Engineering 69: 439–443, 1991.

Sezer A. D., and Akbuga J.: Release characteristics of chitosan treated alginate beads: I. Sustained release of a macromolecular drug from chitosan treated alginate beads, Journal of Microencapsulation 16: 195–203, 1999.

Sezer A. D., and Akbuga J.: Release characteristics of chitosan treated alginate beads: Li. Sustained release of a low molecular drug from chitosan treated alginate beads, Journal of Microencapsulation 16:687–696, 1999.

Wan L. S. C., Lim L. Y. and Soh B. L.: Drug–release from chitosan beads, STP Pharma Siences 4: 195–200, 1994.

Wu F. C., Tseng R. L., and Juang R. S.: Enhanced abilities of highly swollen chitosan beads for color removal and tyrosinase immobilization, Journal of Hazardous Materials 81:167–177, 2001.

Glicksman M.: Gum technology in the food industry, academic press, 412–415, 1969.

Prasad M. P. and Kalyanasundaram M.: Scanning electron microscopic analysis and swelling behaviour of ionotropically crosslinked carboxymethylcellulose and carboxymethylcellulose–gelatin matrices, Carbohydrate Polymers 26: 35–41, 1995.

Prasad M. P., and Kalyanasundaram M.: Iron (iii) carboxymethylcellulose as swellable erodible matrix for the controlled release of a mosquito larvicide, Journal of Controlled Release 22: 167–172, 1992.

Yakup Arica, M.: Immobilization of polyphenol oxidase on carboxymethylcellulose hydrogel beads: Preparation and characterization, Polymer International 49:775–181, 2000.

HYDROGELS HAVING ENHANCED ELASTICITY AND MECHANICAL STRENGTH PROPERTIES

REFERENCE TO RELATED APPLICATION

This application claims the benefit of priority of U.S. Provisional Application No. 60/374,388, filed Apr. 22, 2002.

FIELD OF THE INVENTION

The present invention relates to the synthesis of novel hydrogels, hydrogel foams, and superporous hydrogels. The invention more particularly relates to imparting enhanced elasticity and mechanical strength properties to such hydrogels.

BACKGROUND OF THE INVENTION

Superporous hydrogels (SPHs) are three-dimensional network hydrophilic polymers that absorb a considerable amount of water in a very short period of time due to the presence of many pores having diameters on the micron to millimeter scale (1–4). They are distinguished from other porous hydrogels in terms of their pore sizes and the methods used to generate the pores. For example, the generally accepted sizes for microporous, mesoporous, and macroporous hydrogels are in the range of 10 to 100 nm, 100 to 1000 nm and 1 to 100 $\mu$m, respectively. freeze drying (5), porogens (6–8), microemulsion (9) and phase separation methods (10). In contrast, SPHs are normally prepared by a gas blowing technique, such as is employed in the preparation of plastic foams, e.g., polystyrene or polyurethane foams (11, 12). Pores are generated by the introduction of a small amount of blowing agent within the SPH formulation, which can create gaseous volatile materials as the reacting mixture gels. Faster and greater water absorption are achieved due to the presence of the pores within the SPH structure. Representative reports of such methods and compositions are presented by Park et al. in U.S. Pat. Nos. 5,750,585 and 6,271,278.

The fast and high water absorbent properties of SPHs afford potentially many industrial applications in agriculture, horticulture, hygiene, construction, medical and biomedical fields. They can be used as a particulate to impart a well-defined shape to water-absorbent polymers. They can meet the requirements of such applications as long-term water holding in horticulture and hygienic products, water sealing, or caulking in civil constructions, and the like.

Although previous hydrogel foams and SPHs clearly have industrial applications, a significant shortcoming needs to be overcome in order to extend their applications. As the SPHs absorb lots of water, they become mechanically too weak to maintain their functions for long periods, with their physical structure being easily destroyed even under small stresses. They are rarely re-used once contacted with water. These problems are attributed to the inherent low elasticity properties of SPHs when swollen in water.

Accordingly, it is desired to develop SPHs having enhanced mechanical strength, e.g., by increasing their elasticity, in order to sustain their functions even under rather severe conditions. It is expected that mechanically strong or elastic superporous hydrogels can be used in a vast variety of applications, including those previously reported by Park et al. in U.S. Pat. Nos. 5,750,585 and 6,271,278.

SUMMARY OF THE INVENTION

The present invention is for hydrogels and superporous hydrogels composed of two or more different interpenetrating polymer networks (IPNs), which provide the respective hydrogel or SPH with enhanced elasticity and mechanical strength properties. In a hydrogel or SPH of the present invention, it is believed that the respective polymer chains of the IPNs interlock so as to compensate for weakness or to synergize the strength of each polymer component. A hydrogel having IPNs is sometimes referred to herein as an "IH" and a superporous hydrogel having IPNs is sometimes termed a "SPIH". The selection of polymer networks is preferably restricted to hydrophilic, biocompatible and thermally stable polymers.

A base hydrogel polymer of the invention responsible for its water-swelling properties is formed of at least one ethylenically-unsaturated monomer and a multi-olefinic crosslinking agent. In one aspect of the invention, the base hydrogel polymer is formed in the presence of a strengthening agent, which is typically a crosslinkable natural or synthetic polymer. The strengthening agent thereby occupies the interstices of the base hydrogel polymer matrix. Upon conversion of the strengthening agent to its crosslinked structural form, e.g., by ionic gellation, the resulting product acquires a greater compression modulus than is available to the base hydrogel polymer alone. A hybrid hydrogel composition is thereby formed having enhanced water absorbence and mechanical strength properties. Such hybrid IHs and SPIHs generally have a very short swelling time.

Some earlier preparations of hydrogels and superporous hydrogels have been disclosed by Park et al. in U.S. Pat. Nos. 5,750,585 and 6,271,278, the pertinent portions of which are incorporated herein by reference. The hydrogels described herein are formed without use of a blowing agent, which would impart large pores to the material. In contrast, the SPIHs described herein are formed using a blowing agent and may or may not include particles of a disintegrant, as used to make the SPH composites discussed in U.S. Pat. No. 6,271,278. Many of the disintegrant particles are crosslinked derivatives of some of the strengthening agents employed herein to generate the present elastic SPIHs. However, the methods and compositions disclosed herein afford SPIH compositions having improved mechanical strength properties.

In a typical formulation for an SPIH of the present invention, an admixture of at least one ethylenically-unsaturated monomer, a multi-olefinic crosslinker, strengthening agent, and a blowing agent is employed. This admixture is subjected to polymerization and foaming conditions to polymerize and to crosslink the monomer, and to generate an intermediate SPIH hybrid comprising semi-interpenetrating multiple networks. The intermediate hybrid is then converted to a fully interpenetrating hybrid composition by carrying out physical and/or chemical crosslinking of the strengthening agent. Particles of a disintegrant are optionally provided in the formulation prior to polymerization and foaming, as desired, to impart superporous properties to the hydrogel. The resulting SPIH product is thereby composed of at least two IPNs, whereby one network is primarily responsible for providing water absorbency properties and the other network imparts structural strength to the composite.

An SPIH of the present invention typically has an average pore size in the range of 1–5000 $\mu$m, more commonly in the range of 10–3000 $\mu$m, and frequently in the range of 100–600 $\mu$m. Fast and high water absorbent properties result from the presence of large pores, and such properties allow applications of the present SPIHs in drug delivery, e.g., application in gastric retention. Unfortunately, while previous SPHs possess similar swelling properties, their mechanical strength is too weak to be suitable for many more useful applications. The present invention affords hydrogel materials having superior elasticity and strength properties.

A strengthening agent employed in the present invention generally comprises a natural, semi-synthetic, or synthetic material, which is crosslinkable or non-crosslinkable. Alternatively, the strengthening agent can be characterized as a natural or synthetic polyelectrolyte, or a neutral, hydrophilic polymer. Preferred strengtheners are homo/copolymers of naturally occurring polysaccharides including polymers of alginic acid, chitosan, carboxymethylcellulose (and its derivatives), poly(vinyl alcohol) (PVOH), positively and negatively charged polyelectrolytes (PEL), film-forming polymer emulsions (e.g., homo/multi-polymers of vinyl acetate and various (meth) acrylate derivatives (e.g., methyl, ethyl, butyl)), polyacetonitrile (PAN), natural or synthetic rubber emulsions and dispersions, and the like, and mixtures thereof.

An SPIH of the present invention has significantly improved elasticity and mechanical strength properties compared with previous materials. For instance, the relative compression strength of the superporous hydrogel can be at least 50-fold greater than the compression strength of a superporous hydrogel absent the strengthening agent. Additionally, the tensile strength at breaking point of an SPIH of the invention can be at least about 2.0 kPa.

A strengthened hydrogel or superporous hydrogel of the invention can be employed in a variety of pharmaceutical applications. For example, it can be used to make a pharmaceutical composition in solid dosage form comprising a pharmacologically effective dose of a drug and the strengthened hydrogel or superporous hydrogel. Preferably, the strengthening agent used to make the hydrogel is selected from alginate, chitosan, carboxymethyl cellulose, tannic acid, and gelatin. The hydrogel can be provided within the pharmaceutical composition in tablet, capsule, or particulate form.

ABBREVIATIONS

Figure 1:
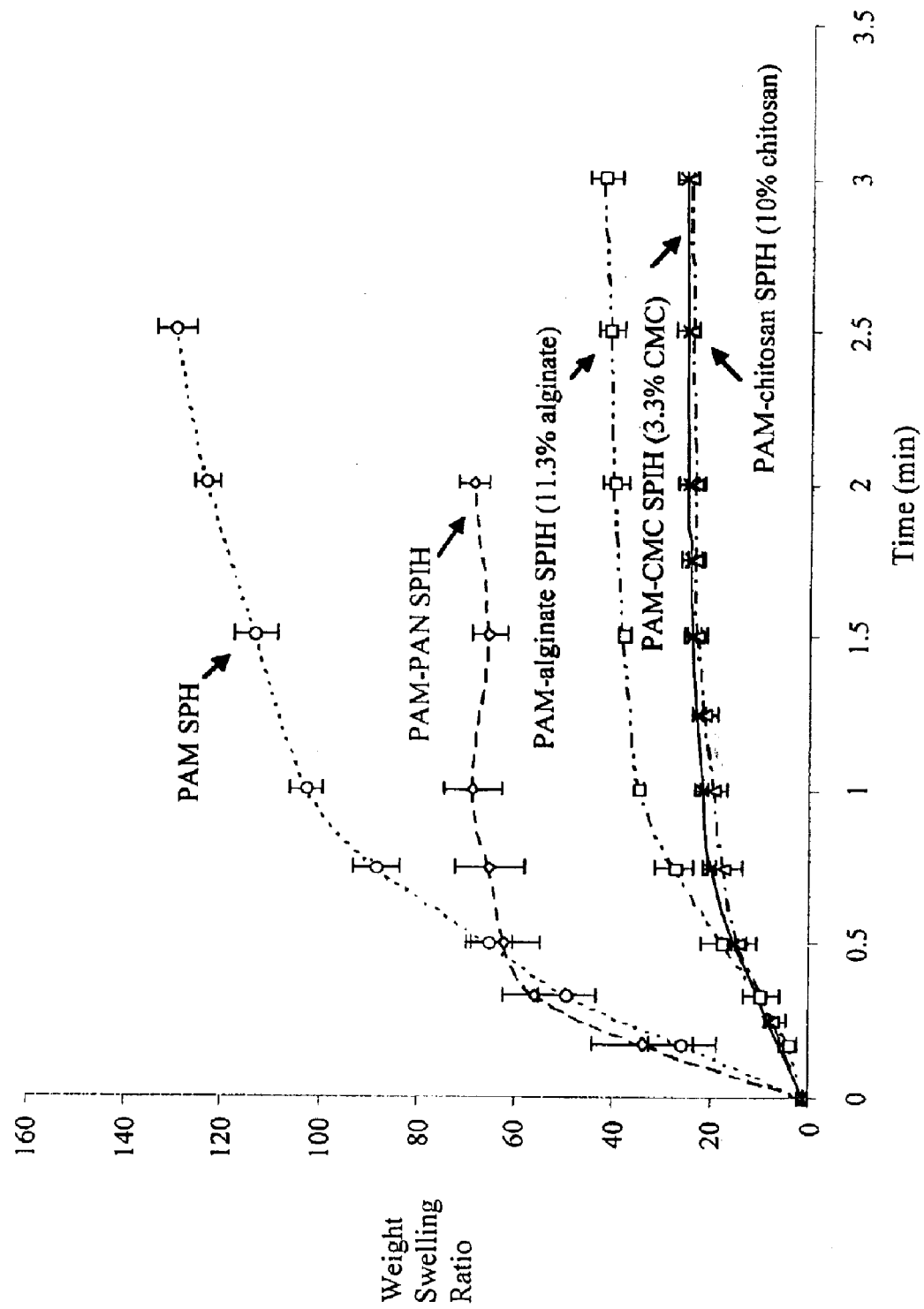
FIG. 1 depicts a graph of the weight swelling ratio as a function of time for a number of superporous IPN hydrogels (SPIH) relative to a polyacrylamide (PAM) superporous hydrogel.

AA: Acetic acid
AAc: Acrylic acid
AAm: Acrylamide
Ac-Di-Sol: Crosslinked carboxymethylcellulose
Alginate (Algin): Sodium salt of alginic acid
AN: acrylonitrile
APS: Ammonium persulfate
BIS: N,N'-methylenebisacrylamide
CAN: Ammonium cerium (IV) nitrate
CMC: Carboxymethylcellulose
DADMAC: Diallydimethylammonium chloride
DW: Distilled water
EBA: N,N'-ethylenebisacrylamide
EO: Ethylene oxide
EtOH: Ethyl alcohol
F127: Pluronic F127®
GAA: Glacial acetic acid
HEA: Hydroxyethyl acrylate
HEMA: Hydroxyethyl methacrylate
H-grade alginate: High viscous alginate
L-grade alginate: Low viscous alginate
M-grade alginate: Medium viscous alginate
NaAAc: sodium salt of acrylic acid
NaCMC: Sodium salt of carboxymethylcellulose
NIPAM: N-isopropyl acrylamide
PAAc: Poly(acrylic acid)
PAAE: A cationic resin of polyamidoamine-epichlorohydrin adduct
PAAm: Polyacrylamide
PAN: Polyacrylonitrile
PDADMAC: Poly(diallyldimethylammonium chloride)
PEC: Polyelectrolyte complexation
PEGDA: Poly(ethylene glycol) diacrylate
PEI: Polyethyleneimine
PEL: Polyelectrolyte
PEO: Poly(ethylene oxide)
PO: Propylene oxide
PPO: Poly(propylene oxide)
PVOH: Poly(vinyl alcohol)
SBC: Sodium bicarbonate
SMBS: Sodium metabisulfite
SPH: Superporous hydrogel
SPAK: 3-sulfopropyl acrylate, potassium salt
TMEDA: N,N,N',N'-tetramethylethylenediamine
TMPTA: Trimethylolpropane triacrylate
TPP: Tripolyphosphate

DETAILED DESCRIPTION OF THE INVENTION

The present invention is for novel hydrogel compositions having improved elasticity and mechanical strength properties, methods of forming them, and novel applications of such materials. A method of forming an hydrogel (HI) composition of the present invention comprises combining at least one ethylenically-unsaturated monomer, a multi-olefinic crosslinker, a strengthener, and particles of a disintegrant (if any) in the form of solid particles or solution. The components are polymerized to yield a hydrogel composite, which is subjected to post-polymerization crosslinking of the strengthener component. An elastic superporous hydrogel composite is formed by further including a blowing agent in the formulation, so that foaming occurs during the polymerization step. A subsequent crosslinking of the primary polymer system affords a superporous hydrogel (SPIH) composition of the invention.

Such a hydrogel material of the invention is provided with enhanced mechanical strength properties by a method of synthesis comprising:

(i) combining at least one ethylenically-unsaturated monomer and a multi-olefinic crosslinking agent to form an admixture thereof, (ii) subjecting the admixture to polymerization conditions, optionally further subjecting the admixture to foaming conditions substantially concurrent therewith, effective to form a hydrogel composite thereof;

(iii) combining at least one strengthening agent with the admixture prior to or after performing step (ii) so that the hydrogel composite contains the at least one strengthening agent; and (iv) subjecting the hydrogel composite containing strengthening agent to strengthening conditions effective to afford the hydrogel material having enhanced strength properties.

Whenever the reaction admixture mentioned above is subjected to foaming conditions while conducting step (ii), a strengthened superporous hydrogel is thereby produced. Generally, it is preferred that an aforesaid strengthening agent is combined with the reaction admixture prior to performing step (ii).

An ethylenically-unsaturated monomer of the present invention is capable of being polymerized, e.g., by radical polymerization, with one or more monomers, crosslinkers, and the like. Exemplary of such monomers are water-soluble or water miscible monomers, such as (meth)acrylic acid, salts of (meth)acrylic acid, esters of (meth)acrylic acid and their derivatives {e.g., 2-hydroxyethyl (meth)acrylate, hydroxypropyl (meth)acrylate, butanediol monoacrylate}, itaconic acid, salts and acids of esters of (meth)acrylic acid, amides of (meth)acrylic acid, N-alkyl amides of (meth) acrylic acid, salts and acids of N-alkyl amides of (meth) acrylic acid, N-vinyl pyrrolidone, (meth)acrylamide, (meth) acrylamide derivatives (e.g., N-isopropyl acrylamide (NIPAM), N-cyclopropyl meth(acrylamide)), diallyldimethylammonium chloride (DADMAC), {2-(methacryloyloxy)ethyl}trimethylammonium chloride, N,N-dimethylaminoethyl acrylate, 2-acrylamido-2-methyl-1-propanesulfonic acid, potassium salt of 3-sulfopropyl acrylate (SPAK), 2-(acryloyloxy)ethyl trimethyl ammonium methyl sulfate, and the like. Particularly preferred monomers include acrylamide (AAm), NIPAM, 2-hydroxyethyl (meth)acrylate (HEA, HEMA), acrylic acid (AAc), inorganic and organic salts (e.g., potassium, sodium and ammonium) of AAc, DADMAC, SPAK, and mixtures of these. Other monomers can of course be used, the identification and formulation of which is well within the skill of the practitioner.

A multi-olefinic crosslinking agent of the present invention permits chemical crosslinking of polymer chains generated during polymerization. Typically, the crosslinking agent is a monomer or polymer containing at least two vinyl groups. Preferred crosslinking agents include N,N'-methylenebisacrylamide (BIS), N,N'-ethylenebisacrylamide (EBA), (poly)ethylene glycol di(meth)acrylate, ethylene glycol diglycidyl ether, glycidyl methacrylate, polyamidoamine epichlorohydrin resin, trimethylolpropane triacrylate (TMPTA), piperazine diacrylamide, glutaraldehyde, epichlorohydrin, as well as degradable crosslinkers including those having 1,2-diol structures (e.g., N,N'-diallyltartardiamide), and functionalized peptides and proteins (e.g., albumin modified with vinyl groups).

Optionally, particles of a disintegrant, which have been found to be effective in increasing the swelling rate and capacity of hydrogels, can also be employed in the present invention. Examples of such disintegrants and their use can be found in U.S. Pat. No. 6,271,278, the disclosure of which is incorporated herein by reference. Whenever such disintegrant particles are employed it is preferred that they are selected from crosslinked natural and synthetic polymers, such as crosslinked derivatives of sodium carboxymethylcellulose, sodium starch glycolate, sodium carboxymethyl starch, dextran, dextran sulfate, chitosan, xanthan, gellan, hyaluronic acid, sodium alginate, pectinic acid, deoxyribonucleic acids, ribonucleic acid, gelatin, albumin, polyacrolein potassium, sodium glycine carbonate, poly(acrylic acid) and its salts, polyacrylamide, poly(styrene sulfonate), poly(aspartic acid) and polylysine. Further examples include crosslinked neutral, hydrophilic polymers, such as those of polyvinylpyrrolidone, ultramylopectin, poly (ethylene glycol), neutral cellulose derivatives, microcrystalline cellulose, powdered cellulose, cellulose fibers and starch. Non-crosslinked forms of the above-mentioned polymers having a particulate shape as well as porous inorganic materials that provide wicking by capillary forces can also be used.

A so-called "strengthener" of the present invention physically intertwines polymer chains formed from the at least one ethylenically-unsaturated monomer, crosslinking agent, and, optionally, disintegrant discussed hereinabove. Without wishing to be limited to any particular theory, upon activation a strengthener of the invention is itself believed to form interpenetrating chains with the aforementioned polymer chains formed from ethylenically-unsaturated monomer and crosslinking agent, thereby affording interpenetrating networks (IPNs) of two or more polymer chains. Upon completion of the foaming and hydrogel generation of the initial polymerization-crosslinking step, which takes place with the strengthener provided in-situ, a post-crosslinking of the strengthener can be conducted to attain increased elasticity. A strengthener in its non-crosslinked, e.g., linearly polymerized, form is conveniently selected from among natural, semi-synthetic, or synthetic materials that are crosslinkable or non-crosslinkable. Alternatively represented, an at least one strengthening agent the present invention is typically a monomer, polymer, or polyphenolic complexing agent. For example, a strengthening monomer can be an amino acid. Alternatively described, an at least one strengthening agent of the invention can be selected from natural and synthetic polyelectrolytes, and neutral, hydrophilic polymers.

A strengthening polymer can be a polysaccharide, such as one or more selected from alginate and derivatives thereof, chitins, chitosan and derivatives thereof, cellulose and derivatives thereof, starch and derivatives thereof, cyclodextrin, dextran and derivatives thereof, gums, lignins, pectins, saponins, deoxyribonucleic acids, and ribonucleic acids. Additionally, a strengthening polymer can be a polypeptide or protein selected from albumin, bovine serum albumin, casein, collagen, fibrinogen, gelatin and derivatives thereof, gliadin, sodium glycine carbonate, bacterial cell membrane enzymes, and poly(amino acids). As for a poly(amino acid), it is preferably selected from polyproline, poly(L-arginine), poly(L-lysine), polysarcosine, poly(L-hydroxyproline), poly(glutamic acid), poly(S-carboxymethyl-L-cysteine), and poly(aspartic acid). Synthetic polymers can also be employed as strengthening agent, such as when the polymer is a homo- or co-polymer comprised of a monomer selected from acrolein potassium, (meth)acrylamides, (meth)acrylic acid and salts thereof, (meth)acrylates, acrylonitrile, ethylene, ethylene glycol, ethyleneimine, ethyleneoxide, styrene sulfonate, vinyl acetate, vinyl alcohol, vinyl chloride, and vinylpyrrolidone.

Preferred strengtheners are homo/copolymers of naturally occurring polysaccharides, including the natural polymers of alginic acid, chitosan, and carboxymethylcellulose (and its derivatives), positively and negatively charged polyelectrolytes (PEL), synthetic polymers, such as polyacrylonitrile (PAN) and poly(vinyl alcohol) (PVOH), film-forming polymer emulsions, e.g., homo/multi-polymers of vinyl acetate and various (meth)acrylate derivatives (e.g., methyl, ethyl, butyl), natural or synthetic rubber emulsions and dispersions, natural or chemically modified proteins, polyphenolic compounds, such as tannin-based complexing agents and derivatives thereof, and the like, and mixtures thereof. Also, grafted derivatives of these using a synthetic monomer, such as AAc, acrylonitrile, AAm, and the like, and mixtures thereof, afford preferred strengtheners.

Particularly preferred strengtheners are selected from polyacrylonitrile, alginic acid (sodium salt, various molecular weights), chitosan (various degrees of deacetylation and molecular weights), sodium salt of carboxymethylcellulose, pectin, natural and seminatural gums, such as starch, xanthan, gellan, carrageenan, gum arabic, guar gum, ghatti gum, tragacanth gum, pontianac gum, karaya gum, agar-agar, methyl cellulose, and hydroxypropyl methylcellulose, natural and modified proteins, such as gelatin, collagen, albumin, bovine serum albumin, fibrinogen, casein, gliatin and the like, polyphenolic materials, such as tannin, tannic acid, galotannins, catechin, chlorogenic acid, arbutin, and the like, poly(diallydimethyl ammonium chloride), gelatin with tannic acid as complex-forming agent, polyethyleneimine (PEI), and PVOH before being crosslinked by any chemical or physical methods. In terms of the ethylenically-unsaturated monomer, it is preferably selected from acrylamide (AAm), N-isopropyl acrylamide (NIPAM), 2-hydroxyethyl (meth)acrylate (HEA, HEMA), acrylic acid (AAc), salts of acrylic acid (potassium, sodium and ammonium), potassium salt of 3-sulfopropyl acrylate (SPAK), poly(ethylene glycol)acrylate, poly(ethylene glycol)alkyl ether acrylate, methacrylic acid-2-dimethylaminoethyl ester, dimethylaminoethyl acrylate and diallyldimethylammonium chloride (DADMAC). A still more particularly preferred strengthening agent of the invention is selected from the group consisting of sodium carboxymethylcellulose, sodium starch glycolate, sodium carboxymethyl starch, dextran, dextran sulfate, chitosan, xanthan, gellan, hyaluronic acid, sodium alginate, pectinic acid, deoxyribonucleic acids, ribonucleic acid, gelatin, albumin, polyacrolein potassium, sodium glycine carbonate, poly(acrylic acid) and its salts, polyacrylonitrile, polyacrylamide, poly(styrene sulfonate), poly(aspartic acid), polylysine, polyvinylpyrrolidone, polyvinyl alcohol, CARBOPOL, ultramylopectin, poly(ethylene glycol), neutral cellulose derivatives, microcrystalline cellulose, powdered cellulose, cellulose fibers, and starch.

A preferred strengthening polyphenolic complexing agent can be a tannin such as one or more gallotannins, ellagitannins, taragallotannins, caffetannins, proanthocyanidins, catechin, epicatechin, chlorogenic acid, and arbutin.

For convenience, the molecular structures of some particularly preferred ethylenically-unsaturated monomers and strengthening agents of the present invention referred to hereinabove are shown in Table 1.

TABLE 1

Materials used for making elastic superporous IPN hydrogels

| Chemical name (abbreviation) | Chemical structure |
|---|---|
| Acrylamide (AM) | (structure: acrylamide, CH$_2$=CH-C(=O)-NH$_2$) |
| Acrylic acid (AA) | (structure: acrylic acid, CH$_2$=CH-C(=O)-OH) |
| 3-sulfopropyl acrylate, potassium salt (SPAK) | (structure: CH$_2$=CH-C(=O)-O-CH$_2$CH$_2$CH$_2$-SO$_3$K) |
| Polyacrylonitrile (PAN) | $-[CH_2-CH]_n-$ with CN side group |
| Alginate | D-Mannuronic acid residues and l-Guluronic acid residues |

TABLE 1-continued

Materials used for making elastic superporous IPN hydrogels

| Chemical name (abbreviation) | Chemical structure |
|---|---|
| Chitosan | 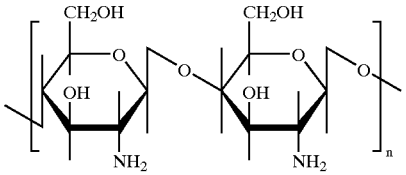 |

Hydrogel strengthening conditions mentioned above can entail contacting a hydrogel composite with a chemical strengthening agent selected from at least one of an ionotropic gellation agent, a polyphenolic complexing agent, an acid, a latex compound, and a glue. An ionotropic gellation agent is preferably selected from calcium chloride, cupric sulfate, ammonium cerium (IV) nitrate, ferric chloride hexahydrate, sodium tetraborate decahydrate, zinc chloride, aluminum chloride hexahydrate, chromium chloride, and pentasodium tripolyphosphate. A polyphenolic complexing agent is preferably selected from among gallotannins, ellagitannins, taragallotannins, caffetannins, proanthocyanidins, catechin, epicatechin, chlorogenic acid, and arbutin. Alternatively, the strengthening conditions can entail subjecting the hydrogel composite to cryogellation conditions, such as by applying a freeze-thaw cycle on PVOH and the hydrogel composite.

Post-crosslinking of a hydrogel of the present invention in the presence of a strengthener can be accomplished chemically, physically or by any other method, including irradiation. Preferred post-crosslinking chemical agents include any multifunctional crosslinkers (e.g., containing hydroxyl, carboxyl, amine, epoxy, amide, urethane groups, and the like), divalent/multivalent metallic cations (e.g., calcium, magnesium, zinc, copper, barium, iron, aluminium, chromium, cerium), phosphates (e.g., pentasodium tripolyphosphate (TPP)), chromates (e.g., dipotassium dichromate), borates (e.g., sodium tetraborate decahydrate), peroxides (e.g., t-butyl hydroperoxide), glycidyl(meth) acrylate, ethylene glycol diglycidyl ether, glutaraldehyde, glycerin, glycols, polyamidoamine epichlorohydrin resin, TMPTA, and the like, and mixtures thereof. Representative crosslinking methods include thermogelation, ionotropic gelation, cryogelation, radiation-induced gelation, chemical gelation, coagulation, crystallization, vulcanization, curing, and combinations thereof. More preferred post-crosslinking methods employ ionotropic gelation (e.g., using anhydrous calcium chloride, cupric sulfate, ammonium cerium (IV) nitrate, ferric chloride hexahydrate, sodium tetraborate decahydrate, zinc chloride, aluminum chloride hexahydrate, chromium chloride, and anhydrous TPP) and cryogelation (e.g., by applying freeze-thaw cycles to PVOH solutions and using another cryogelable materials).

Polymerization can be initiated by any known applicable mechanism, including photochemical (e.g. using a UV lamp), thermal (e.g. using ammonium persulfate (APS)) and oxidation-reduction reactions (e.g. using APS/sodium metabisulfite (SMBS) or APS/tetramethylethylene diamine (TMEDA).

Various foaming techniques can be employed within the present invention. A preferred method is to conduct the foaming by means of a blowing agent dissolved or dispersed in the admixture of monomer, crosslinking agent, (disintegrant) and strengthener. Particularly preferred blowing agents are sodium bicarbonate (SBC) and ammonium bicarbonate (ABC), which can be admixed with an acid, such as glacial acetic acid (GAA), as needed to initiate decomposition of the carbonate and generate gaseous bubbles of $CO_2$.

Suitable polymerization and foaming conditions as referred to herein include ambient pressure and a temperature in the range of 5–90° C.; more preferably ambient temperature of 20–50° C. and most preferably 25–30° C. The time allowed for successful polymerization and foaming is conveniently in the range of a few seconds to 1 hr, more preferably 30 sec to 5 min and most preferably 2–4 min.

Strong elastic SPIHs can be obtained using some of the materials employed in tissue engineering, cell immobilization and scaffolding. Chemically and ionotropically crosslinked alginate and chitosan, polyurethane-imide and polyurethane-urea (13), commercially available polyurethanes (14, 15), ∈-caprolactone and L-lactide copolymers (16), poly(glycolic acid), poly(lactic acid) and their copolymers (17, 18), gelatin (19), and photo-crosslinked poly (ethylene oxide) (20) are found useful in these fields and can potentially be used to produce an elastic SPH according to the present invention. Gums including xanthan, agar, carrageenan, guar and another food gums may also be useful to make strong and elastic superporous hydrogels.

Gelatin is a widely used pharmaceutical excipients and is a denatured, biodegradable protein obtained by acid and alkaline processing of collagen. Gelatin with different isoelectric points can be generated via the process of changing the electrical nature of collagen by acid or alkaline. A polyion complex is formed by the ionic interaction of positively or negatively charged gelatin with an oppositely charged protein. Gelatin can also form complexes with polyphenolic materials, such as tannins. Tannins have been known for their ability to form complexes with numerous types of molecules including carbohydrates and polysaccharides, proteins, bacterial cell membranes and synthetic polymers such as polyvinylpyrrolidone (PVP) and polyethylene glycol, polyacrylic acid, etc. The strong complexes formed by tannin with gelatin and carboxymethylcellulose are exploited herein as strengtheners to improve the mechanical properties of superporous hydrogels.

Techniques employed in the paper industry to make wet strength paper can also be exploited to produce strong or elastic SPHs. These may include urea-formaldehyde resins (21), melamine-formaldehyde resins (21), polyacrylamide resins (21), acrylic emulsions (21), anionic styrene-butadiene lattices (21), animal glues (22), soybean protein (22), corn or wheat starch (22), cationic cornstarch (22), polyamide resin in alcohol solution (22), ethyl cellulose in alcohol solution (22) and water-dispersible polyisocyanates (23).

Additionally, materials including silica, carbon black, glass, polyester, nylon, viscose, aramide and Kevlar fibers, alumina, methylcellulose (MC), ethyl cellulose (EC), hydroxyethylcellulose (HEC), Portland cement, calcium oxide, and the like, and mixtures thereof, can be used as particulate and fibrous fillers within a SPH formulation in order to obtain increased strength properties.

The strengtheners used in this invention can be described, and are conveniently referred to, as "primary" and "secondary" in terms of the final strength and elasticity properties they afford. The primary approaches adopted by the present invention employ alginate (using sodium alginate in the presence of calcium ions), chitosan (using chitosan in the presence of phosphate ions), carboxymethylcellulose (CMC) (using sodium carboxymethylcellulose in the presence of ferric ions), pectin (using sodium pectinate in the presence of calcium ions), and cryogel (using poly(vinyl alcohol)), polyacrylonitrile (PAN), and mixtures thereof as such strengtheners. According to the invention, another approach using polysaccharide/non-saccharide polymers can be considered "primary" if the polysaccharide or non-saccharide polymer makes a strong bead in contact with an ionic gelation medium. Accordingly, any polymer regardless of its origin, i.e., natural or synthetic, which can be crosslinked and make a strong polymer bead after gelation can be a useful approach to make elastic superporous hydrogels. Those strengtheners that afford the strongest beads can be considered primary in view of their effect on SPH modulus and elasticity.

Some "secondary" synthetic approaches of the present invention employ acidification, impregnation (e.g., with poly(DADMAC) and PEI), latex incorporation, crosslinked gelatin, ionotropically-crosslinked non-polysaccharides (e.g., acrylic acid, poly(acrylic acid), AAm and polyacrylamide), wet paper strengtheners, and thermogelation.

It should be noted that elastic superporous hydrogels of the present invention have distinctly different properties compared to those of normal superporous hydrogels. Although they can swell very rapidly to a very high capacity, the latter cannot withstand even weak pressures or stresses. Accordingly, they break easily under any kind of stress including tensile, compression, bending, twisting, and the like. In contrast, an elastic superporous hydrogel of the present invention can significantly withstand the aforementioned loads. Depending on the synthetic approach taken to make an elastic SPH, more or less elasticity can be obtained. The maximum elasticity is provided by the primary approaches mentioned above. Polymers modified by the primary approaches of this invention can resist virtually any kind of stress. The hydrogels modified by secondary approaches are resistant against certain kinds of stresses, in particular compressive stresses, and generally can be called high modulus.

In particular, a strengthened hydrogel or superporous hydrogel of the present invention typically has an average pore size of about 1 $\mu$m to about 5000 $\mu$m, and is preferably in the range of about 10 $\mu$m to about 3000 $\mu$m. A superporous hydrogel of the invention can have a relative compression strength that is at least 50-fold greater than the compression strength of a superporous hydrogel absent a strengthening agent. Also, a superporous hydrogel of the invention can have a tensile strength at breaking point of the strengthened superporous hydrogel that is at least about 2.0 kPa. For such superporous hydrogels, the equilibrium volume-swelling ratio of the strengthened superporous hydrogel is typically in the range of about 8 to about 18.

A pharmaceutical composition of the present invention in solid dosage form comprises a pharmacologically effective dose of a drug and a strengthened hydrogel or superporous hydrogel made by a foregoing method. Typically, a strengthened hydrogel or superporous hydrogel employed in the pharmaceutical composition contains at least one strengthening agent selected from alginate, chitosan, carboxymethyl cellulose, tannic acid, and gelatin. The pharmaceutical composition is typically in tablet, capsule, or particulate form, and can be administered to a patient orally, mucosally, transdermally, or by other readily apparent modes of administration. Whenever a tablet or capsule is employed, it is preferably formed by a molding, direct compression, or press coating compression technique.

I. Hydrogel IPN Compositions and Methods of Preparation

The synthetic procedures of the present invention are generally as described by Park et al., U.S. Pat. No. 6,271,278 (1), however, some modifications are described hereinbelow. Individual monomers show selective compatibility with different synthetic approaches taken. For instance, the most selective and compatible SPIH products obtained used AAm as polymerizable monomer, or AAm and SPAK as comonomers, and employed alginate, chitosan or carboxymethylcellulose as primary strengtheners. The compound 2-HEA showed the maximum compatibility with the cryogel approach of the invention.

Considering both the final polymer properties (hydrogel swelling and strength) and the SPH process requirement, the formulation of a typical AAm-based hydrogel is identified (see Examples A–C). This formulation renders the highest possible strength under the process limitations. The gelation features (inhibition period, exothermic period and temperature rise) were found to be dependent on the nature and concentration of the materials within the hydrogel formulation. This correlation is exploited later to design a simple formulation in order to make a strong superporous hydrogel network. Among the variables studied, dilution with water (monomer concentration) and comonomer concentration (acrylic acid in this case) show strong influence on the gelation properties. A reasonable relationship is found between the strength properties of the hydrogel and the gelation features. The inhibition period is the period in which normal polymerization is inhibited or retarded at least because of the presence of air, in particular oxygen. The exothermic period is the period during which normal polymerization occurs for a definite time dependent on formulation and process factors. During this period, the reaction temperature rises to its maximum again according to the formulation and process conditions. It is found that tough or very tough AAm-based hydrogels and superporous hydrogels are normally attainable under conditions of minimal inhibition and exothermic periods and maximal temperature rise (during gelation).

In qualitative terms, increased concentrations of foam stabilizer, redox couple and crosslinker (in a definite lower range of concentration) result in reduced inhibition and exothermic periods and also in increased temperature during gelation. A detailed discussion of the formulation design can be found elsewhere (24).

Normal polymerization is favored by shorter inhibition and exothermic periods due to less possibility of oxygen reaction with monomers. Therefore, to obtain a higher molecular weight polymer or high conversion of monomer to polymer, shorter inhibition and exothermic periods are desired. On the other hand, to obtain a successful well-structured and homogeneous SPH, a kind of so-called cell freezing (very fast gelation) should be practiced. These two similar requirements are mainly achieved at high monomer concentration (less dilution with water), low acrylic acid (AAc) concentration and high F127 concentration. Although increased TMEDA and APS additions result in a similar effect, care should be taken to avoid very low molecular weight polymer chains. Increased temperature rise during the exothermic process means more reaction, i.e., higher conversion of monomer to polymer. This requirement can be attained at high initiator concentration, and in particular at high reductant concentration.

For a superporous hydrogel to be tough, an optimized viscoelastic behavior is desirable. At extremely elastic behavior where the crosslink density of the hydrogel is very high, the polymer chains are not easily relaxed under certain stresses or loads. On the other hand, at extremely viscous behavior in which the lowest crosslink density is applicable, the polymer chains are free to relax and display the behavior of a fluid under load. Accordingly, an optimum amount of crosslinker concentration to permit reasonable chain stress relaxation is preferred.

With the base formulation containing 500 μl AAm (50 wt %), the following optimizations were made to give a strong base for producing an elastic superporous hydrogel:

Water concentration: preferred (0–3000 μl), more preferred (500–1500 μl) and most preferred (500–750 μl);

BIS concentration: preferred (100 μl of 0.5–4 wt % solution), more preferred (100 μl of 1–3 wt % solution) and most preferred (100 μl of 1 wt % solution);

Pluronic® concentration: preferred (25–300 μl of 10 wt % solution), more preferred (50–200 μl of 10 wt % solution) and most preferred (200 μl of 10 wt % solution);

Glacial acrylic acid concentration: preferred (10–100 μl), more preferred (20–50 μl) and most preferred (30 μl);

APS concentration: preferred (5–100 μl of 10–20 wt % solution), more preferred (15–50 μl of 10–20 wt % solution) and most preferred (40–50 μl of 20 wt % solution);

TMEDA concentration: preferred (5–100 μl of 20–40 v/v % solution), more preferred (15–50 μl of 20–40 v/v % solution) and most preferred (40–50 μl of 40 v/v % solution);

SBC concentration: preferred (5–100 mg), more preferred (20–70 mg) and most preferred (25–40 mg);

Time for SBC addition: preferred (5–400 sec before the gelation period), more preferred (5–50 sec before the gelation period) and most preferred (15–25 sec before the gelation period);

Reaction temperature: preferred (5–90° C.), more preferred (20–50° C.) and most preferred (25–30° C.); inhibition period: preferred (10 sec–10 min), more preferred (10 sec–3 min) and most preferred (less than 1 min); and Exothermic or gelation period: preferred (0.5–5 min), most preferred (0.5–2 min); temperature rise during reaction: preferred (>10° C.), more preferred (>30° C.) and most preferred (>50° C.).

According to the present invention, strengthener is generally added in its solution/emulsion or dispersion form to the mixed solution of monomer, crosslinker, foam stabilizer, disintegrant (if any), foaming aid (e.g. AA, acrylic acid) before addition of redox components. The addition can simply be done by any kind of mixing procedures. The mixing should be gentle enough to prevent any sensible viscosity change of the mixing solution. The simultaneous foaming, polymerization and crosslinking is similar to a conventional SPH preparation (1).

Particular notes on the individual approaches are made in the following sections. After foaming and temperature decline (after gel formation), the superporous hydrogel is further treated by a particular treating medium (e.g., for superporous hydrogel modified with alginate, this can be a typical calcium chloride solution). With some approaches, thermal treatment is required (e.g., latex addition or thermogelation). Another kind of treatment is cryogelation, (e.g., inducing the gelation of PVOH through successive freezing and thawing). Other post-polymerization steps, such as crosslinking, curing, crystallization, coagulation, vulcanization, gelation, and the like, and combinations of these, can be exploited to produce an elastic SPH according to the present invention.

The concentration of post-crosslinking medium can affect the mechanical properties of the elastic SPIH. Preliminary experiments showed that alginate crosslinked in the presence of low and high crosslinker concentration showed different strength properties. Strong ties between the two polymer networks are considered to lead to better mechanical strength of SPIH, so tight entanglements are desired. In addition, highly crosslinked polysaccharide system showed least extractable amounts of alginate from the network. Therefore, ionotropic gelation at high crosslinker amount is appropriate. For example, in the alginate SPIH synthesis, a highly concentrated solution of $CaCl_2$, i.e., 30 wt %, is preferably used.

For the cryogel approach, post-crosslinking can be done by controlling the freeze/thaw cycle. Because of the intermolecular hydrogen bonding between OH groups of adjacent polymer chains, ordered structures called microcrystalline zones can be formed, and in this way concentrated PVOH aqueous solution can form a noncovalent spatial network gel under prolonged storage. Since higher PVOH content in the system can lead to higher strength and thermostability, 7–15% solutions of PVOH (MW 80–100 kDa) are usually used. Though the freezing rate has little effect on the physical properties of cryogels in the range of 0.1–17.0° C. $min^{-1}$, thawing rate does significantly influence cryogel properties in that slower thawing results in higher strength. It has been shown that multiple freezing-thawing cycles can afford results similar to slow thawing.

Superporous IPN hydrogels represent a new kind of hydrogel resembling normal SPHs in having numerous large-size pores, which usually in the range of several hundred micrometers, and can be up to the millimeter range. Also, like the original SPH, most of the pores inside superporous IPN hydrogels are interconnected to form an open channel system. Even after drying, the pores of superporous IPN hydrogels remain connected to each other forming capillary channels. Because of this, dried superporous IPN hydrogels can swell extremely fast, as do the original SPHs, upon contact with water. When inspected with scanning electron microscopy (SEM), scaffold-like fiber network structures can be observed along and between the walls of most open pores of superporous IPN hydrogels. Because these scaffold polymer networks do not block the open pores of superporous IPN hydrogels, fast swelling kinetics is maintained while mechanical properties and elasticity are significantly improved. This unique microscopic structure along with the superior mechanical properties distinguishes the present superporous IPN hydrogels (SPIHs) from the original SPH and SPH composites.

Primary Approaches

Particularly satisfactory elastic superporous hydrogels are obtained by so-called primary approaches. These include:

A. The Alginate approach: Alginates are a family of linear unbranched polysaccharides that contain varying amounts of 1,4'-linked β-D-mannuronic acid and α-L-guluronic acid residues (25, 26). Alginate can make a gel in the presence of divalent cations including $Ca^{2+}$, $Sr^{2+}$ or $Ba^{2+}$. Cations $Ba^{2+}$ and $Sr^{2+}$ produce stronger alginate gels than $Ca^{2+}$. Monovalent cations and $Mg^{2+}$ do not induce gelation. Other divalent cations such as $Pb^{2+}$, $Cu^{2+}$, $Cd^{2+}$, $Co^{2+}$, $Ni^{2+}$, $Zn^{2+}$ and $Mn^{2+}$ can also crosslink the alginate but their use is limited due to their toxicity. The exchange of the sodium ions from the guluronic acids with divalent ions, and the stacking of these guluronic groups to form the characteristic egg-box structure achieve the gelation and crosslinking. The divalent cations bind to the α-L-guluronic acid blocks in a highly cooperative manner and the size of the cooperative unit is more than 20 monomers. Each alginate chain can dimerize to form junctions with many other chains to form gel networks rather than insoluble precipitates (26).

Ionically crosslinked alginate hydrogels have previously been used as scaffolds for tissue engineering(27), as biomedical(28), cell culture/transplantation (29) and cell immobilization(30). The internal bead structure(31) and gelation models(32) of calcium-induced alginate solution have been studied using NMR. In another work (33), the equilibrium and viscoelastic properties of ionotropically-crosslinked alginate gel (using $Ca^{2+}$) have been evaluated in terms of alginate concentration and exposure time to physiologic concentrations of NaCl. Moreover, chemically crosslinked alginate hydrogels have been used as a controlled release medium for drugs (34–38), pesticides (39) and also as superabsorbent filament fibers (40). In another work (41), a flocculating agent based on graft copolymers of sodium alginate with polyacrylamide has been attempted using a ceric ion-initiated solution polymerization technique at room temperature. Similarly, a novel semi-interpenetrating network (semi-IPN) system has been developed to make a polymer membrane(42). The first network consisted of sodium alginate that provided the crosslinked network. The other was polyacrylic acid or polyacrylamide, which imparted its characteristics into the polymer membrane. For this purpose, the combined solutions of the two polymers were treated with 5 wt % aqueous calcium chloride solution to form a gel matrix. Another example of the simultaneous application of two polymer systems with alginate polymers is preparation of crosslinked membrane by casting an aqueous solution of alginate and 1,6-hexanediamine (HDM) onto a hydrolyzed microporous polyacrylonitrile membrane (43). Exploiting simultaneous ion-induced and photo-induced crosslinking respectively for alginate and polyvinyl alcohol has also been attempted to produce a biocompatible material (44).

However, it is believed that no example of fully interpenetrating networks involving a synthetic monomer system and alginate have been reported. In the present invention, a semi-interpenetrating network is first prepared (e.g., through chemical crosslinking of the synthetic monomer) in the presence of uncrosslinked alginate. The system is then converted to a fully-interpenetrated network (e.g., through ionotropic gelation of the polysaccharide component, which is sodium alginate).

Since addition of strengthener results in a marked change of reaction mixture concentration, monomer concentration, and the like, the foam height should be optimized to attain reasonable swelling and elastic properties. Therefore, with a typical glass reactor that has an aspect ratio of 0.11 (I.D/H), an optimum foam volume was found around 60% of the reactor volume. With a defined SPH formulation employing a AA/ SBC/F127 combination as a foaming and stabilizing system, the most important factors determining the foam volume and its structure are the amount and the ratio of these three components. Based on an extensive study, taking into account the foam volume, swelling ratio, swelling capacity, elasticity, diffusional absorption, capillary absorption, foam homogeneity and reproducibility, the optimal concentrations were found as 40 μL AA, 30 mg SBC and 200 μL of 10 wt % F127 solution in water based on 500 μL of 50 wt % acrylamide solution (45). This formulation was employed with the other approaches.

Alginate concentration. In terms of strength properties, a preferred alginate concentration was found to be 1000–2500 μL, more preferably in the range of 1300–2000 μL and most preferably in the range of 1500–1750 μL based on a 500 μL AAm solution (50 wt %).

Alginate type: Low to high viscous grades are applicable. The same bulk alginate solution viscosities are attainable at 0.6, 2.0 and 3.0 wt % alginate concentration for high, medium and low viscous grades, respectively. At the same solution viscosity, the most preferred alginate type is a low viscous grade because of its higher solid content in solution.

Alginate solution concentration: Alginate solution concentration can be optional but is limited by process requirements. A preferred concentration is 1–4 wt % with low grade alginate. Preferred concentrations were found in the range of 2–3 wt %, more preferably 2.0 wt %.

Alginate solution preparation: The most preferred method of solution preparation is by pouring the alginate powder over distilled water under very gentle agitation for 1 min to break up aggregations, followed by setting the dispersion aside overnight and gently homogenizing it. Since viscosity of the alginate solution is shear dependent and aging dependent, care should be taken to avoid high shear mixing and long-term storage before use.

Post-crosslinker concentration: The parameters affecting the gel strength of alginate beads were examined using aqueous solutions of low viscosity grade of alginic acid (sodium salt, 3 wt %) and calcium chloride (0.089–28.57 wt %). The minimum crosslinker concentration was found between 0.089–0.17 wt % to make stable and integrated alginate beads. For this study, a micrometer (AMES, Waltham, Mass., USA), a UV detector (Gilson, Model 111B) and a bench comparator (AMES, Waltham, Mass., USA) were used to measuring the bead size, extractable fraction and the mechanical strength of the beads, respectively.

Without wishing to be bound to any particular theory, the mechanism by which polysaccharides can introduce strength to, for example, synthetic AAm-based hydrogels can be by tight interlocking of the hybrid network after ionotropic gelation. Alginate crosslinked in the presence of low and high crosslinker concentration shows different strength properties. Accordingly, at high crosslinker concentration, the SPH strength is noticeable. Given the fact that alginate composition and its strength remain nearly the same within a broad range of crosslinker concentration used (according to UV and deformation data) (45), the most applicable range of post-crosslinker concentration to assure a mechanically strong SPH should be in the range of 0.44–14.28 wt %. To produce a tight entanglement with synthetic polymer chains, the polysaccharide should presumably be highly crosslinked to prevent it from swelling in water. This can help to maintain strong ties between the two polymer systems. Also, the ties should be mechanically strong enough to prevent any deformation that presumably results in loosening the ties to polymer chains. This can also be achieved by doing ionotropic gelation at high cation concentration. Finally, a highly crosslinked polysaccharide incorporates the highest polysaccharide concentration since UV data show the least extractable amounts of alginate from a network of the highly crosslinked system. Accordingly, a highly concentrated solution of the crosslinker ($CaCl_2$), i.e., 30 wt %, is preferred in these studies.

Alginate type: According to U.S. Pat. No. 5,718,916 (46) different alginates have different ratios of their two main building blocks, i.e., mannuronic (M) and guluronic (G) acids. Depending on the source of supply, alginate from *Macrocstis pyrifera* consists of 61/39 ratio of M/G while those from *Laminaria hyperborean* consists of 31/69 ratio of M/G. This can seriously affect the consistency of the alginate gels from flexible to rigid ones. Since divalent cations bind to guluronic acid blocks, it is expected that alginate composed primarily of guluronic residues make much stronger gel than those composed of mannuronic blocks.

B. The Chitosan approach: Chitosan is a naturally occurring highly basic polysaccharide with excellent biodegradable and biocompatible characteristics. Due to its unique polymeric cationic character and its gel and film forming properties, chitosan has been examined extensively in the pharmaceutical industry for its potential in the development of drug delivery systems (47, 48). Covalently crosslinked chitosan has been attempted in chitosan-silica nanocomposites by reacting tetramethoxysilane to the hydroxyl groups of the chitosan and also using glutaraldehyde. Also, an interesting property of chitosan is its ability to make a gel in contact with specific polyanions like TPP(48, 49):

A controlled-release protein delivery system was investigated using various model drugs. Chitosan was reacted with sodium alginate in the presence of TPP for bead formation. To avoid the toxicity problems with glutaraldehyde, sodium alginate has been tried as crosslinker (50, 51). Chitosan-TPP gel has been attempted as membrane (52) and chelating resin (49). An attempt was also made to prepare chemically (53) and ionotropically-crosslinked chitosan microspheres by an emulsion-phase separation technique (54). The preparation of hydrogels from the polyelectrolyte complexes of carboxymethylcellulose (CMC) and hydrogels from the complexation with an additional or simultaneous ionotropic gelation was reported (55). An improved crosslinking characteristic of the chitosan-TPP beads was also reported (56). Cell immobilization (57) and drug delivery systems (58, 59) have been made based on ionotropically-crosslinked chitosan and alginate combination. In another study, gelatin and sodium alginate have been used to improve the mechanical strength of TPP/chitosan beads (47). Chitosan-TPP bead loaded with high dosage of drug was also made (60). Chitosan crosslinking using ethanolic NaOH solution has also been reported (61). However, nothing appears reported on fully-interpenetrating networks involving a synthetic monomer system and chitosan. In the present invention, first a semi-interpenetrating network is prepared (e.g., through chemical crosslinking of the synthetic monomer), and is then converted to a fully-interpenetrated network (e.g., through ionotropic gelation of the polysaccharide portion, i.e., chitosan).

C. The CMC (Carboxymethylcellulose) approach: One of the most important derivatives of cellulose is the sodium salt of carboxymethylcellulose (NaCMC). Although it is soluble in water and insoluble in organic solvents, it can be dissolved in mixtures of water and water-miscible solvents like alcohol or acetone (62). CMC solutions are fairly stable over a wide pH range of about 5–10, with best stability at a pH of 7–9. Acidification below pH 5 tends to reduce viscosity and viscosity stability of the CMC solution. Below pH of 3, precipitation of the free carboxymethylcellulose acid may occur (63). CMC is an anionic water-soluble polyelectrolyte (64) and its aqueous solutions can be gelled in the presence of various cations (cupric sulfate and iron chloride) to make an insoluble cupric carboxymethylcellulose and ferric carboxymethylcellulose, respectively. These gels have been used previously in controlled-release (65) and enzyme immobilization (66) studies. CMC gel matrices can also be formed using gelatin as an interactive polymer followed by ionotropic crosslinking (67, 68). Scanning electron microscopic analysis and swelling behavior of ionotropically crosslinked carboxymethylcellulose and carboxymethylcellulose-gelatin matrices have been studied (64). It is believed that fully-interpenetrating networks involving a synthetic monomer system and CMC have not been previously described. As discussed above for other systems, a semi-interpenetrating network is first prepared (e.g., through chemical crosslinking of the synthetic monomer), and then is converted to a fully-interpenetrated network (e.g., through ionotropic gelation of the polysaccharide portion, that is, sodium salt of carboxymethylcellulose).

D. The Pectin approach: Pectin has a fairly complex heterogeneous structure and is composed chiefly of polygalacturonic chains having a wide variety of molecular weights. Some of the carboxyl groups are esterified with methyl alcohol, some are neutralized with cations and some are free acids (25). In fact, pectins are predominantly linear polymers of mainly α-(1-4)-linked D-galactouronic acid residues interrupted by 1,2-linked L-rhamnose residues. Generally, divalent metal ions can react with carboxyl groups from adjacent pectinate chains to form a gel network (69), and low ester content pectin can form gels by controlled introduction of calcium ions through interchain associations. This may result in extended conformationally regular junction zones possibly similar to that depicted in the egg box model projected for alginates (70).

In a similar way, pectin beads are prepared by dropping solutions of pectin into calcium chloride solutions. The droplets instantaneously form gelled spheres by ionotropic gelation. This technique has been used previously in drug delivery(38, 71–74), protein delivery(75, 76) and cell immobilization(77). However, it is believed that fully-interpenetrating networks involving a synthetic monomer system and pectin have not been previously described. Herein, a semi-interpenetrating network is prepared and is converted to a fully-interpenetrated network (e.g., through ionotropic gelation of the polysaccharide portion, that is, sodium pectinate).

E. The Cryogel approach: PVOHs are hydrophilic polymers that can make a noncovalent spatial network gel under prolonged storage when in highly concentrated aqueous solution. The major intermolecular interaction is that of hydrogen bonds between OH groups of adjacent polymer chains. The syndiotactic and isotactic sites within the polymer chains are responsible respectively for intermolecular and intramolecular interactions through hydrogen bonding (78).

As a result of these interactions, PVOH chains can form ordered structures called microcrystalline zones. The degree of deacetylation (DD), polymer molecular weight (MW) and tacticity are important parameters in determining the ability of PVOH solutions to make a gel and for cryotropic gelation. Cryotropic gelation is favored with highly deacetylated PVOH types. The polymer concentration in the initial solution is also of importance, so that the higher the PVOH content, the higher the strength and thermostability of the frozen system. However, very concentrated (>20 wt. %) solutions of PVOH are excessively viscous especially when the polymer MW exceeds 60–70 kDa. Solutions of PVOH (7–15%) with MW 80–100 kDa are therefore usually employed.

The regimes of cryogenic treatment processes have a pronounced effect on the properties of PVOH-based cryogels. The temperature for freezing/melting of aqueous PVOH solutions lies a little below zero ($0>T_m>-1°$ C.). The change in physical properties of the cryogel is minor if the freezing rate is in the range of 0.1–17.0° C. min. On the other hand, very fast freezing, e.g., in liquid nitrogen, can cause undesirable crack formation within the bulk of the cryogel.

By far, the most significant parameter was found to be the thawing conditions. The slower the thawing process, the higher the strength of the PVOH cryogel formed. It has been shown that multiple freeze-thaw cycles play the same role as slow thawing (78). It has been noted that freeze-thaw treatment of low and highly concentrated aqueous PVOH solutions results in cryoprecipitation and opaque gels, respectively (79, 80). To increase the swelling kinetics of the cryogelled PVOH, cellular hydrogels have been attempted using NaCl (81). The structure, properties, synthesis, crystallization and morphology of the PVOH cryogels have been studied in detail (82, 83). In another study, mechanisms of cryotropic gelation of PVOH and influencing parameters were studied (84). Regarding PVOH cryogels, osmotic properties (85), rheological and thermal properties (in the presence of crosslinked dextran (86) and some polyol (87)), amount of sol and gel fraction (88), influence of low molecular weight polyelectrolytes (89) and their applications in cell immobilization (78) and protein delivery (90) systems have been studied. However, it is believed that fully-interpenetrating networks of a synthetic monomer system and a cryogel type polymer have not previously been described. As before, a semi-interpenetrating network is first prepared (e.g., through chemical crosslinking of the synthetic monomer), which is then converted to a fully-interpenetrated network (e.g., through cryogelation of the cryogellable portion, that is, PVOH chains).

F. The PEI approach: Polyethyleneimine is a branched weak polycation containing primary, secondary and tertiary amine groups (91). This polycationic polyelectrolyte can form interchain complexation in the presence of oppositely-charged monomers, oligomers and polymers by which strength properties of the superporous hydrogel can be improved.

G. The PAN approach: Superporous hydrogels, such as poly(AM-co-SPAK), can be placed in a solution of acylonitrile (AN, Aldrich) so that the SPH is filled with AN solution. The AN-filled SPH is then exposed to polymerization conditions so that AN polymerizes to form PAN within the pores and channels of the SPH. The PAN-penetrated SPH shows improved mechanical strength and elasticity properties. The concentration of AN can be controlled to adjust the elasticity of the PAN-penetrated SPH product, as desired.

Any combination of the different primary approaches described above can be practiced in any order according to the principles of the present invention to prepare elastic hydrogels or superporous hydrogels.

Secondary Approaches

All the following approaches to forming strengthened SPHs, except those using latex and PDADMAC as strengthener, showed nearly the same effect on the gel strength. They increased the compression modulus and gel strength, and potentially are very useful in this regard. In terms of accentuating strength properties, the latex and PDADMAC approaches are intermediate to primary and secondary approaches.

Acidification: This approach can be used primarily for hydrogel systems containing, in part, an anionic monomer, e.g., acrylic acid. This kind of modification promotes hydrogen bonding and van der Waals forces that in turn affect strength properties of the hydrogel product.

Impregnation with Poly(DADMAC): Mineral surfaces have been treated previously using polyelectrolyte complexes (PEC) in an attempt to modify the surfaces. The PEL tested were polyethyleneimines of different molecular weights, poly(DADMAC) and a copolymer of maleic acid and propene or styrene (91, 92). Polyelectrolyte complexes (PECs) are formed by a combination of aqueous PEL solutions containing definite amounts of polyanion and polycation charges (93). This kind of modification has been attempted to increase the solution viscosity, increase resistance to temperature and salt, and enhance oil recovery. For this purpose, a combined solution of AAm-acrylic acid copolymer and AAm-diallyldimethylammonium chloride (DADMAC) copolymer has successfully been tried (94). The interactions between these two oppositely charged polymers and the viscosity of the complex solution have been studied by instrumental analysis (95, 96). A similar approach exploiting interchain complex formation is used here to produce higher strength superporous hydrogels.

Latex addition: According to the present invention, emulsion, dispersion or solutions of polymers, in particular of rubbers having low to very low glass transition temperatures can be used to prepare elastic superporous or normal hydrogels. The glass transition temperature of the polymer can be as high as 40–60° C. The most preferred polymer systems according to this aspect of the invention are emulsions of a low glass transition temperature hydrophobic polymer in water. These, for example, may include copolymers or terpolymers of vinyl acetate and different acrylates (e.g. methyl, ethyl, butyl), natural or synthetic rubbers (e.g. polyisoprene and styrene-butadiene). An acrylic latex is used here as a strengthener of a superporous hydrogel.

Chemically crosslinked gelatin: According to this aspect of the invention, a semi-interpenetrating network involving a synthetic monomer system and gelatin are prepared (e.g., through chemical crosslinking of the synthetic monomer part) and the product is then converted to a fully-interpenetrated network (e.g., through chemical crosslinking of gelatin).

Ionotropic gelation of synthetic polymers: Analogous to polysaccharides, ionotropic gelation of synthetic polymers can produce high strength superporous hydrogels. First, a semi-interpenetrating network of a synthetic monomer system and homopolymers of poly(vinyl acetate) and PVOH is prepared (e.g., through chemical crosslinking of the synthetic monomer part). The network is then converted to a fully-interpenetrated network (e.g., through ionotropic gelation of the added homopolymer). Similarly, acrylic acid, Poly(acrylic acid), AAm and Poly(AAm) can also be separately introduced to the monomer solution of the hydrogel system and then ionotropically gelled using di- or trivalent cations.

Using paper wet strengthener: A cationic resin of polyamidoamine-epichlorohydrin adduct (PAAE, Kymene 557 H, Hercules) was studied with the AAm formulation containing acrylic acid, in part. Kymene 557 H is most commonly used as wet strengthening agent in paper manufacturing.

Thermogelation: Polymers that can be thermally gelled or crosslinked can be useful to increase the strength of superporous hydrogels. This was examined with AAm-based superporous hydrogel using egg white that contains thermogellable ovalbumin protein.

II. Swelling Properties of Superporous IPN Hydrogels

A. Swelling Ratio Measurement

For the swelling study, deionized distilled water (DDW) was used as the swelling medium. Each superporous IPN hydrogel sample was cut into a cylindrical shape. The hydrogel samples were weighed and measured in diameter and length and then immersed into DDW to swell at room temperature. At predetermined time points, the sample was taken out of water and excess water was removed from the surface using a Kimwipe® (Kimberly-Clark Corp.). The weight, diameter and length of the swollen samples were measured using a balance (Fisher Scientific) and an electronic digital caliper (VWR Scientific Prod.). The weight swelling ratio and volume swelling ratio were calculated based on those measured data. The weight swelling ratio ($Q_w$) is defined as:

$$Qw = \frac{w_s}{w_d},$$

where $w_s$ is the weight of the swollen SPIH sample and $w_d$ is the weight of dried SPIH sample. The volume swelling ratio ($Q_v$) is defined as:

$$Qv = \frac{V_s}{V_d}$$

where $V_s$ is the volume of the swollen superporous IPN and $V_d$ is the volume of the dry superporous IPN sample. The swelling time is the time for a SPIH sample to reach the equilibrium swollen state. The weight and volume swelling curves were plotted to compare the swelling kinetics of hydrogel samples.

B. Comparison of Superporous Hydrogels and Superporous IPN Hydrogels

Original superporous hydrogels (SPH) and superporous hydrogel composites (SPHC) were prepared by the same methods described in U.S. Pat. No. 6,271,278. According to the kinetics of the swelling of a gel (98), the characteristic time of swelling ($\tau$) is proportional to the square of the characteristic length of the gel (L) and is inversely proportional to the diffusion coefficient of the gel network in the solvent (D) as:

$$\tau = L^2/D$$

The diffusion coefficient of hydrogel networks in on the order of $10^{-7}$ $cm^2$/sec. Because there are many interconnected open pores inside the SPH structure, water can reach the surface of the hydrogel pores very fast due to the capillary effects. The actual swelling time of the polymer matrix is also short because the thickness of the cell wall of SPH, which is essentially the characteristic length of the SPH, is very low. Due to these, SPH and SPH composites have very fast swelling kinetics. Fast swelling kinetics is a unique property of SPHs and is preserved for SPIHs with improved mechanical properties.

When a second polymer network is formed inside a superporous hydrogel, the swelling capacity of the resulted superporous IPN hydrogel decreases. As shown in the specific samples in Table 2, the weight swelling ratio and volume swelling ratio of SPIH decreased 50%–75% depending on the type and amount of strengtheners penetrated inside the original SPH.

TABLE 2

| Superporous hydrogel Type | Equilibrium swelling ratio (weight) | Equilibrium swelling ratio (volume) | Swelling time (sec) |
|---|---|---|---|
| original SPH P(AM-co-SPAK) | 113.4 ± 9.5 | 36.3 ± 2.8 | 120 |
| SPH composite P(AM-co-SPAK) with PAN | 82.5 ± 17.2 | 26.7 ± 4.6 | 180 |
| SPIH P(AM-co-SPAK)-PAN | 45.2 ± 4.0 | 18.6 ± 0.8 | 240 |
| SPIH PAM-PAN with 0.2 mol % crosslinker | 68.7 ± 3.7 | 11.0 ± 1.4 | 90 |
| SPIH PAM-PAN with 0.1 mol % crosslinker | 49.1 ± 4.4 | 19.2 ± 3.7 | 120 |
| SPIH PAM-alginate (11.3% alginate) | 42.1 ± 3.3 | 11.5 ± 1.2 | 180 |
| SPIH PAM-alginate (12.0% alginate) | 33.0 ± 1.6 | 9.1 ± 0.9 | 180 |
| SPIH PAM-alginate (12.5% alginate) | 23.4 ± 1.3 | 8.8 ± 1.0 | 180 |
| SPIH PAM-chitosan (10% chitosan) | 24.6 ± 1.0 | 5.2 ± 0.4 | 180 |
| SPIH PAM-CMC (3.3% CMC) | 25.5 ± 2.2 | 8.1 ± 0.6 | 180 |
| SPIH PAM-alginate-CMC (11.3% alginate, 5% CMC) | 23.8 ± 2.8 | 9.5 ± 0.7 | 300 |

The decrease in weight swelling ratio is due to the fact that the loaded strengtheners, such as PAN or alginate, are not as hydrophilic as the polymers forming the original SPH, e.g. PAM or P(AM-co-SPAK). The decrease in volume swelling ratio is due to the fact that the polymer networks formed by the strengtheners are also tightly entangled and tied with the original SPH polymer networks, which restrains the volume change of the hydrogels. Although the swelling capacity was decreased when the strengtheners IPN structures formed inside superporous hydrogels, the swelling speed of superporous IPN hydrogels was not compromised, reaching equilibrium in about 2–5 minutes. These results indicated that the interconnected channels were not blocked by the strengthener networks.

From the swelling curves shown in FIG. 1, the swelling behavior is similar for the original SPH and modified SPIH, consisting of a fast water absorption process at beginning and a hydration process near the plateau. The water absorption rate is determined by the effectiveness of the capillary action in a superporous hydrogel. From the swelling curves shown in FIG. 1, it is clear that IPN networks formed by PAN have similar capillary effectiveness as original SPH, and IPN networks formed by alginate, clitosan and CMC have less capillary effectiveness, indicated by the smaller initial slope of each swelling curve.

C. Effect of Original SPH Properties on Swelling Behaviors of SPIH

Superporous IPN hydrogels are formed by two polymer networks, i.e., the original SPH network and the strengthener network. Therefore, the swelling properties of SPIH are not only determined by how hydrophilic the strengthener is, but also affected by the properties of the original SPH.

1. Effect of Monomer Type on Swelling Properties of Superporous IPN Hydrogels

The swelling capacity of superporous IPN hydrogels is affected by the monomers used to synthesize the superporous hydrogel. The weight and volume swelling ratios of SPIH using different selected monomer materials are shown in Table 3 hereinbelow. As shown, the P(AM-co-AA) SPIH has significantly lower swelling capacity compared to PAM and P(AM-co-SPAK) SPIH samples. This could be due to the carboxyl groups on the AA segments interacting with nitrile groups on the PAN chains forming some tight entanglement. Another explanation could be that the carboxyl groups of AA segment undergo hydrogen bonding among themselves because the further link of PAN networks resulted in more opportunities of interaction. Therefore, the overall hydrophilic property of the copolymer decreases because of these inner hydrogen bonds. The SPIH samples of P(AM-co-AA)-PAN are more tough and stiff than other PAN-modified SPIH samples, which is indicative of more effective crosslinking inside the gel networks. Similar effects can be expected on SPIH samples using other strengtheners.

TABLE 3

| Superporous hydrogel Type | Equilibrium swelling ratio (weight) | Equillibrium swelling ratio (volume) | Time to reach swelling equilibrium (sec) |
| --- | --- | --- | --- |
| SPIH PAM-PAN | 68.7 ± 3.7 | 11.0 ± 1.4 | 90 |
| SPIH P(AM-co-SPAK)-PAN | 45.2 ± 4.0 | 18.6 ± 0.8 | 240 |
| SPIH P(AM-co-AA)-PAN | 10.2 ± 1.0 | 2.3 ± 0.1 | 180 |

To design an elastic superporous IPN hydrogel with good swelling capacity, not only the hydrophilic and mechanic properties of the strengtheners need to be studied, but also the functional groups on the monomers forming the SPH need to be considered. The possible interaction between the side chain functional groups and strengtheners can influence the properties of SPIH substantially.

2. Effect of Crosslinking Density Swelling Properties of Superporous IPN Hydrogels As shown in Table 2, the volume swelling ratios of PAM-PAN SPIH synthesized using 0.2 mol % and 0.1 mol % crosslinker (BIS) are 11.0 and 19.2 respectively. An average of 1.75 fold increase in volume swelling ratio was observed on the PAN modified SPIH when the crosslinker concentration in the formulation was lower in half. According to previous research, less crosslinker concentration will result in less crosslinking density and therefore more interchain space [5]. After post-crosslinking modification, the volume change of superporous IPN hydrogels is further restrained by the second polymer networks formed between and along the cell walls of original SPH. When the interchain spaces are larger due to the less crosslinking, the second polymer network can move more freely, and results in apparent higher volume swelling ratio. On the other hand, when the interchain spaces are smaller because of high crosslinking, the volume change of the IPN hydrogel upon contacting of water will also be lower.

III. Mechanical Properties of Superporous IPN Hydrogels

The high mechanical strength of superporous hydrogel is critical for many potential applications. Highly swelling hydrogels usually have poor mechanical strength and such a drawback limits many hydrogels from broad practical applications. Therefore, improving the mechanical properties while maintaining high swelling ratio and kinetics is highly desirable.

A. Testing Method of Mechanical Properties

Mechanical properties of swollen superporous hydrogels and IPN gels were examined using Stable Micro Systems (Texture Technologies Corp.). The hydrogel samples were cut into certain lengths of cylindrical shape and swollen in DDW to equilibrium. The swollen hydrogel samples were longitudinally mounted on the Stable Micro Systems. The initial diameter and length of the hydrogel sample was measured in order to calculate the cross-section area and percent of strain. Both the compression and tensile strength were examined. The raw output of the strength curve was plotted as force (N) versus distance (mm). Normalization of the strength curve was conducted by obtaining compression or tension stress and strain in order to compare the different samples. The compression or tension stress can be obtained in international units, i.e., Pa, via dividing the output force by the cross-section of the swollen specimen. The compression strain was calculated by:

$$\lambda_{com} = \frac{L_1}{L_0} \cdot 100\%$$

where $L_0$ is the original length of the swollen sample, and $L_1$ is the compression displacement in the compression test. The tension strain was determined by:

$$\lambda_{ten} = \frac{L_1 + L_0}{L_0} \cdot 100\%$$

where $L_1$ is the elongation displacement in the compression test. Different test speeds of compression and tension ranging from 1.0 mm/s to 10 mm/s were conducted to determine if the deformation speed would affect the results. After the data was examined by statistical analysis, the displacement speed (compression or tension) has no significant effects on the testing results of SPIH. Thus, for either the compression or tensile test, the pre test and post test speed was set to 2.0 mm/s, and the test speed was 1.0 mm/s. The trigger force was set to be 0.02 N, and all data were obtained in quintuplicate.

B. Compression Strength Properties of Superporous IPN Hydrogels

To be used to develop a gastric retention device, the swollen superporous hydrogel should be strong enough to withstand the peristaltic contraction. Therefore, compression strength is one crucial factor to be improved for the superporous hydrogel. The original SPH is very weak after fully swollen, and it easily cracks during compression.

Figure 2A:
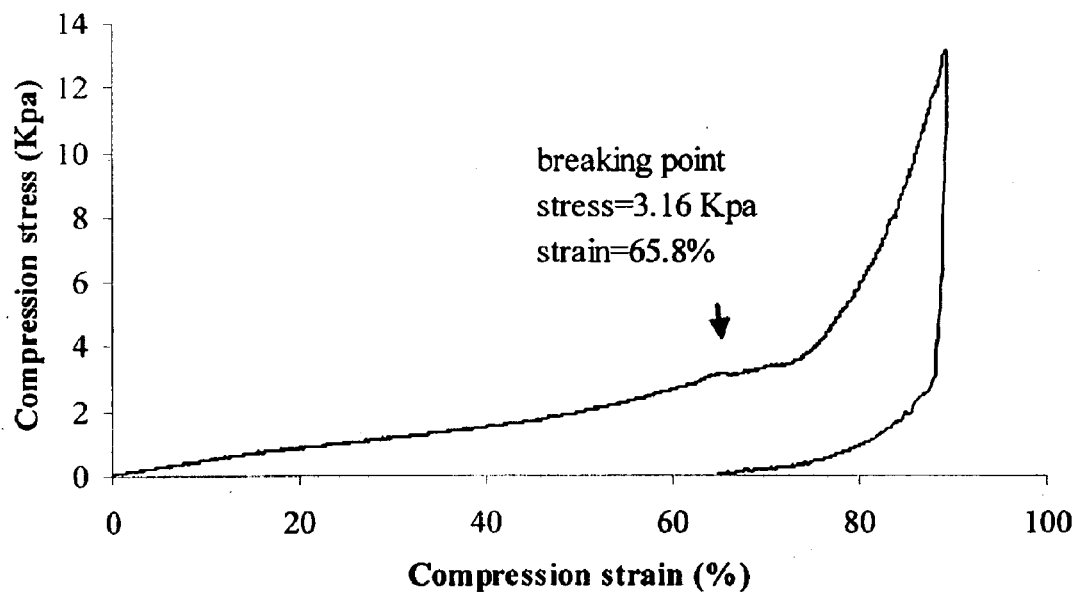
FIG. 2A illustrates the compression stress versus compression strain for a conventional poly(AM-co-SPAK) superporous hydrogel.
Figure 2B:
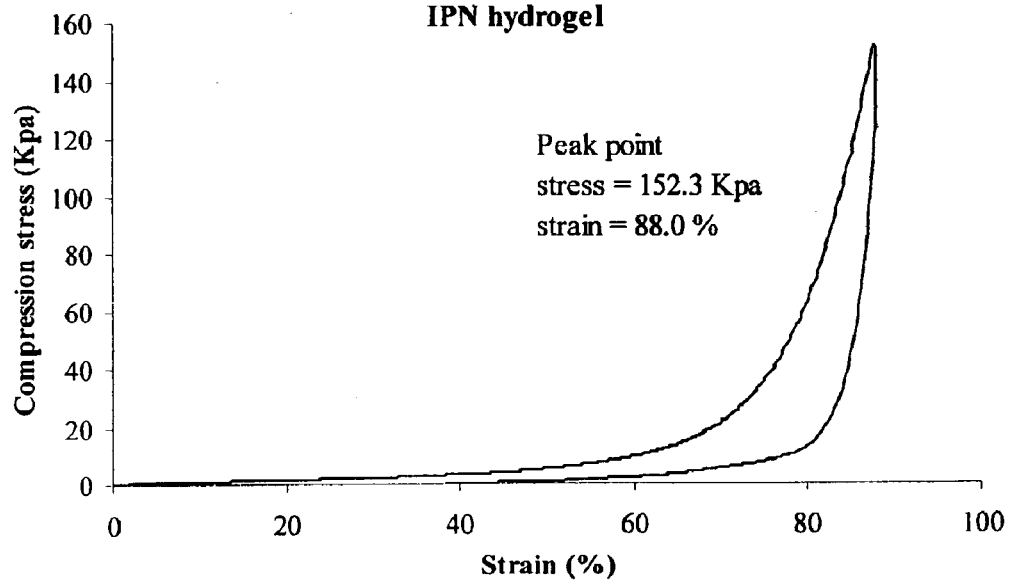
FIG. 2B illustrates the same compression curve for a poly(AM-co-SPAK) superporous IPN hydrogel where polyacrylonitrile (PAN) polymer chains are used to create the interpenetrating networks.

FIG. 2A shows a normalized compression curve of P(AM-co-SPAK) superporous hydrogel sample, and the fracture point can be observed in the curve, which is labeled as breaking point in the figure. On the other hand, PAN or polysaccharides modified superporous IPN hydrogels shows strong mechanical strength to withstand rather high compression stress. As shown in FIG. 2B, there is no fracture observed in the compression curves of P(AM-co-SPAK)-PAN superporous IPN hydrogel sample. Superior elasticity is observed in the SPIH samples, as the SPIH samples can relax back when the compression stress disappears. Because of this superior elasticity, SPIH can be compressed repeatedly without broken.

For hydrogels, the covalent network is not the only thing that keeps the hydrogel structure together. Besides the normal chain entanglements, hydrophilic polymers can mutually interact with their high polar hydrophilic groups in dry state. This explains why dry hydrogels are normally strong, hard glassy materials. When the hydrogels are hydrated, those mutual strong interactions among the hydrophilic groups are cancelled. Therefore, the hydrated hydrogels are typically rubbery and much weaker (99). Because the original superporous hydrogel is totally composed of hydrophilic polymers, it becomes very fragile after fully swollen. Since the hydrophobic groups are not hydrated, the hydrophobic interactions between chains may survive in swollen state, and thus maintain the mechanical strength. In addition to that, when a second polymer network of various strengtheners is formed inside the SPH structure, they can function as a scaffold that maintains the hydrogel structure and improves the mechanical strength. When the scaffold structures formed by the strengtheners are flexible and easily oriented, the superporous IPN hydrogels will possess superior elasticity.

The compression strength and strain of several SPHs and SPIH products of the present invention are compared in Table 4. These include previously described PAM SPH, P(AM-co-SPAK) SPH, P(AM-co-SPAK)-PAN SPH composite, as well as P(AM-co-SPAK)-PAN superporous IPN hydrogel, PAM-alginate superporous IPN hydrogels with various alginate contents, PAM-chitosan and PAM-CMC superporous IPN hydrogels. The results are summarized in Table 4 hereinbelow.

TABLE 4

| Superporous hydrogel Type | Compression stress (Kpa) | Compression strain (%) | Broken under stress |
|---|---|---|---|
| P(AM-co-SPAK) SPH | 3.51 ± 0.93 | 67.3 ± 4.6 | Yes |
| P(AM-co-SPAK)-PAN SPH composites | 3.35 ± 0.28 | 69.8 ± 2.7 | Yes |
| P(AM-co-SPAK)-PAN SPIH | 175.4 ± 26.7 | 88.2 ± 2.3 | No |
| Original PAM SPH | 12.0 ± 2.4 | 81.8 ± 4.1 | Yes |
| SPIH PAM-alginate (11.3% alginate) | 646.9 ± 34.7 | 91.7 ± 1.3 | No |
| SPIH PAM-alginate (12.0% alginate) | 435.0 ± 33.0 | 90.3 ± 2.1 | No |
| SPIH PAM-alginate (12.5% alginate) | 765.7 ± 37.6 | 94.2 ± 0.5 | No |
| SPIH PAM-chitosan (10.0% chitosan) | 656.0 ± 74.1 | 94.3 ± 0.3 | No |
| SPIH PAM-CMC (3.3% CMC) | 789.5 ± 41.9 | 92.6 ± 0.9 | No |
| SPIH PAM-alginate-CMC (11.3% alginate, 5% CMC) | 857.1 ± 75.3 | 92.3 ± 2.6 | No |

As clearly shown, introducing a complete strengthener network inside SPH structure can dramatically increase the compression strength of the superporous hydrogel. As mentioned in U.S. Pat. No. 6,271,278, incorporation of a super-disintegrant like Ac-Di-Sol® can increase the compression strength of superporous hydrogel by 1.6 fold. In the present invention, because of the complete IPN structure formed by post-crosslinking of strengtheners, the compression strength of superporous IPN hydrogels is increased to about 50–70 fold (e.g. 50-fold increase with PAN modification, 200-fold increase with alginate or chitosan modification, and 250-fold increase with CMC modification) of the original strength. Furthermore, because of the superior elasticity of superporous IPN hydrogels, they can withstand repeatedly compression without broken and relax back to their original shape.

C. Tensile Strength Properties of Superporous IPN Hydrogels

Figure 3:
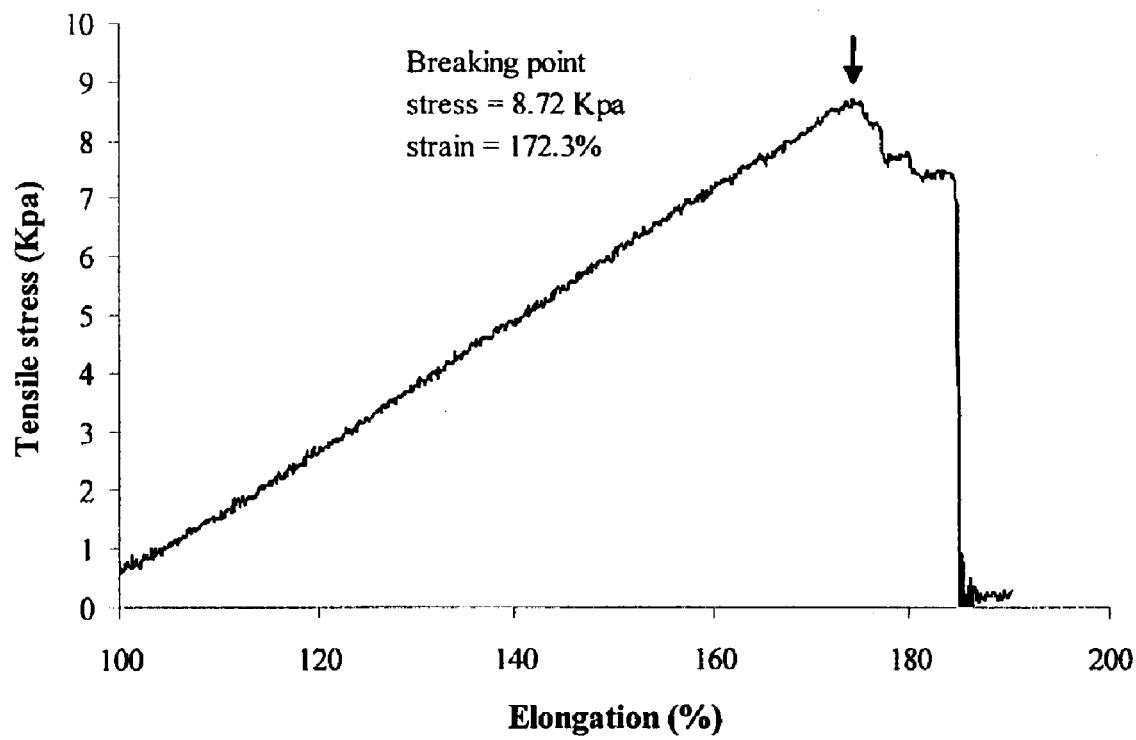
FIG. 3 shows the relationship between tensile stress and percent elongation for a PAN/poly(AM-co-SPAK) superporous IPN hydrogel.
Figure 4:
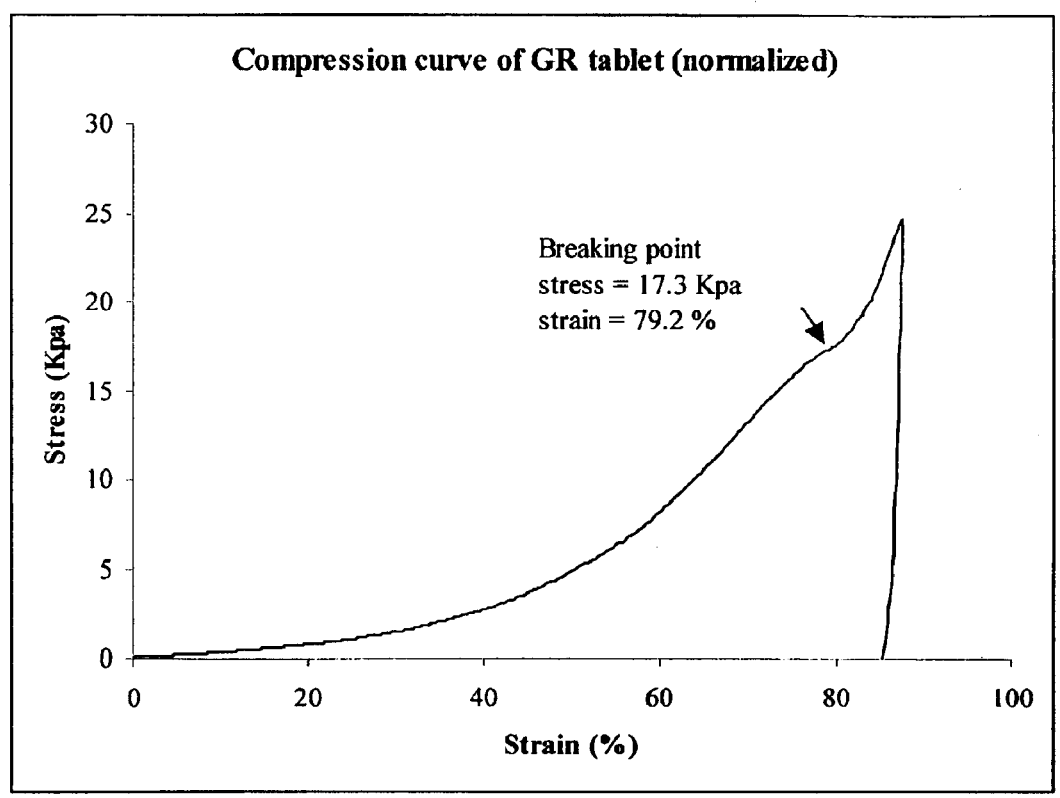
FIG. 4 shows the relationship of stress and strain for a gastric retention tablet of the invention.

To be used in tissue engineering, cell immobilization and scaffolding, a hydrogel must have high elasticity. To estimate elasticity, tensile strength was examined for the various superporous IPN hydrogels. Because originally formulated (unstrengthened) superporous hydrogels and superporous hydrogel composites are too weak, the tensile strength test could not be conducted on these two types of SPHs. A representative normalized tensile strength curve of fully swollen P(AM-co-SPAK)-PAN SPIH is shown in FIG. 3. In this sample, the PAN penetrated P(AM-co-SPAK) superporous IPN gel can be stretched to 173% of its original length before breaking. The SPIH samples modified by polysaccharide strengtheners, such as alginate or chitosan, have even better elasticity.

The elastic modulus, E, was also determined from the slope of linear dependence of equation:

$$\sigma = E(\lambda - \lambda^{-2})$$

where $\sigma$ is the applied stress, and $\lambda$ is the relative deformation of the specimen elongation strain in the tensile test. Five samples were examined for each type of superporous IPN hydrogel hybrid, and the means and standard errors of elongation strain and tensile stress at breaking point are summarized in Table 5 hereinbelow.

Because the incorporated strengthener chains are crosslinked into an entire network, the network conformation can be oriented under tensile stress. Depending on how the strengthener networks are incorporated inside the SPH pores, their elastic strains are different. For example, since the PAN networks are formed along and between the cell walls of the SPH pore structures, which is visualized in SEM images, the SPIH samples modified with PAN possess high elastic modulus but stretch less than alginate or chitosan modified SPIH. Because the networks formed along the cell walls, the superporous IPN hydrogens modified with alginate or chitosan possess relatively small elastic modulus but can be stretched to more than 250% of their original length without breaking.

TABLE 5

| Superporous hydrogel Type | Tensile stress (Kpa) | Tensile strain (%) | Elastic modulus (Kpa) |
|---|---|---|---|
| P(AM-co-SPAK)-PAN SPIH | 11.53 ± 3.76 | 170.0 ± 13.3 | 8.18 ± 2.57 |
| SPIH PAM-alginate (11.3% alginate) | 2.07 ± 0.07 | 242.9 ± 10.0 | 0.69 ± 0.18 |
| SPIH PAM-alginate (12.0% alginate) | 2.16 ± 0.09 | 302.1 ± 11.0 | 0.44 ± 0.10 |
| SPIH PAM-alginate (12.5% alginate) | 3.03 ± 0.18 | 271.8 ± 11.5 | 0.71 ± 0.17 |
| SPIH PAM-chitosan (10.0% chitosan) | 3.01 ± 0.21 | 290.0 ± 20.1 | 0.64 ± 0.18 |
| SPIH PAM-CMC (3.3% CMC) | 2.98 ± 0.29 | 281.4 ± 17.2 | 0.64 ± 0.12 |
| SPIH PAM-alginate-CMC (11.3% alginate, 5% CMC) | 3.05 ± 0.07 | 228.3 ± 15.4 | 1.16 ± 0.21 |

To obtain a visual impression of how elastic the superporous IPN hydrogels can be, photographs of repeated stretching of a PAM-alginate SPIH sample can be taken. The PAM-alginate SPIH samples can be stretched up to 2.5 times of their original length without breaking. The stretching and relaxation can be repeated many times as long as the elongation limit of the superporous IPN hydrogels is not exceeded. It is believed that such elasticity has not been reported for hydrogels before.

IV. Microscopic Structures of Superporous IPN Hydrogels

Because fast swelling kinetics is maintained for superporous IPN hydrogels, it is apparent that the capillary channels, which are formed by the interconnected pore structure, are not blocked. To confirm this hypothesis, cryo-SEM was used to observe the detailed microscopic structure inside the hydrated superporous IPN hydrogels. A P(AM-co-SPAK) superporous hydrogel sample and a P(AM-co-SPAK)-PAN superporous IPN sample were compared in dry state. From the images, it is clear that pore size and pore structure are similar for the original SPH and the PAN SPIH sample. The pore size is around 100 $\mu$m, and the pores are all interconnected. Different from the original SPH, many collapsed fibrous structures can be observed on the struts of superporous IPN samples, which make the IPN sample coarser in appearance.

The cryo-SEM images of a P(AM-co-SPAK)-PAN superporous IPN sample in swollen state clearly show that there are many fiber networks formed along and between the SPIH pore walls. But those fiber networks do not block the open pore structures; they just form scaffold-like structures connecting the pore walls together. These microscopic structures correlate well to the previous swelling studies and mechanical studies. Because the interconnected pore structures are not blocked by the strengthener polymer networks, the capillary effect of rapid absorbing water is not affected. It is believed that the mechanical property improvements are due to the PAN polymer networks formed inside the pores of SPH and these networks can prevent the fragile pore structure from collapsing under compress pressure.

Cryo-SEM images of a PAM-alginate superporous IPN hydrogel sample in swollen state were also examined. Unlike the fiber networks formed by PAN polymers, the fiber networks formed by alginate-$Ca^{2+}$ crosslink are mainly along the pore walls of SPH. Similar microscopic structures were also observed in superporous IPN hydrogels using chitosan as strengtheners. These microscopic results explain the reason why SPIH with alginate or chitosan as strengtheners possess higher elasticity (more elongation) and lower elastic modulus than the SPIH with PAN as the strengthener. The fiber networks along the pore walls of SPIH can easily orient conformation upon stretching and render more elasticity to the SPIH.

The cryo-SEM images of a PAM-CMC superporous IPN hydrogel sample in swollen state were also examined. The microscopic structures of SPIH modified with CMC as strengtheners are clearly different from those of PAN, alginate and chitosan modified superporous IPN hydrogels. The walls at the edge of the pores are very dense compared with the original SPHs and other SPIHs. On the other hand, the small cells on the pore walls are still similar as in other SPHs and SPIH samples. The interconnected open pores are conserved; therefore, the swelling kinetics of the CMC-modified SPIH is not affected. The strengthening of CMC-modified superporous IPN hydrogels is primarily on the pore walls of the hydrogel. Because of this different strengthening, the CMC modified SPIH samples have significant higher compression strength represented by withstanding higher compression stress. This means the SPIH modified with CMC as strengtheners are stiffer than other types of SPIH samples.

Because of the second polymer networks formed inside the superporous hydrogels, no matter what conformations they adopt, a restriction on volume changes is enforced upon hydrogel swelling. The volume swelling ratio of various SPIH gels is rather consistent and independent of the type and amount of strengtheners used. The volume increment is limited to the range of 8 to 18 for all the different superporous IPN hydrogels whereas the weight swelling ratios are quite different for each type of SPIH gels. This is because the volume cannot be increased once the strengtheners' fiber networks reach their extension limits in water, while the hydrophilic properties of various strengtheners can be very different.

As discussed above, all the microscopic structures are well correlated to the macroscopic properties of the various superporous hydrogel materials. Every aspect of characteristic macroscopic properties, including swelling behaviors and mechanical properties, can be explained by the microscopic structures obtained from cryo-SEM microscopic images of that material. All the significant differences found in formal statistical data analysis have their corresponding explanations in the microscopic structure images.

V. Applications of Superporous IPN Hydrogels

Superporous hydrogels were initially proposed to develop gastric retention devices (100). However, with the improved mechanical properties and superior elasticity, many more applications can be developed for the superporous IPN hydrogels. Because of the unique properties of superporous hydrogels, research has centered on the areas of gastric retention devices, superabsorbent, and chemoembolization devices.

A. Gastric Retention Devices

Gastric retention devices may be highly useful for the delivery of many drugs, although the fact that the active ingredient will be retained in the stomach for the entire time of release will make some drugs unsuitable for this delivery. Gastric retention devices would be most beneficial for drugs that need to act locally in the stomach, e.g., antacids and antibiotics for bacterially-based ulcers, or that may be absorbed primarily in the stomach, e.g., albuterol (101). For many drugs that have a narrow absorption window, i.e., mainly absorbed from the proximal small intestine, such as riboflavin, levodopa, p-aminobenzoic acid (102,103), controlled release in the stomach would improve the bioavailability. For drugs that are absorbed rapidly from the GI tract like amoxicillin (104), slow release from the stomach is also expected to improve bioavailability. Gastric retention devices can also be used for drugs that are poorly soluble at an alkaline pH or drugs that degrade in the colon (e.g., metoprolol) to realize oral controlled delivery. The drugs unsuitable for prolonged stomach delivery include aspirin and nonsteroidal anti-inflammatory drugs, which can cause gastric lesions, and drugs that are unstable in the acidic pH. In addition, for those drugs that are primarily absorbed in the colon, longer gastric retention may not be necessary because the time spent in the colon can sustain blood levels for up to 24 hours (105).

Many attempts have been made to develop gastric retention devices. Each type utilizes one of the properties of the stomach or stomach fluid in order to be retained in the stomach. For example, floating devices can stay above the pyloric sphincter by floating in the gastric juice because of their buoyant bilayer, lower density cores, or gas-generating systems (105–109). Mucoadhesive devices can be retained in the stomach because the carboxylic acid components, when protonated, are adhesive to the lining of the stomach due to hydrogen bonding (110–114).

Several important properties of the superporous hydrogel make it an excellent candidate material to develop gastric retention devices. Those properties are fast swelling, large swollen size, and surface slipperiness after certain modifications. Because of those properties, superporous hydrogels can be developed as gastric retention devices small enough to swallow easily and large enough after hydration to be kept in the stomach. Previous studies have investigated the gastric retentive time of superporous hydrogels in stomachs of dogs. The animal studies showed that the most important property to improve is the mechanical strength of the superporous hydrogels, because the SPH samples broke into smaller pieces and then emptied from the dog stomach, indicating the mechanical strength was not good enough. The addition of Ac-Di-Sol® to make superporous hydrogel composites improved the mechanical properties somewhat. However, in the present invention, superporous IPN hydrogels possess not only much improved mechanical properties but also superior elasticity for withstanding repeated compression. These improved mechanical properties make SPIH more suitable for developing successful gastric retention devices.

Example 31 hereinafter presents a representative formulation to make gastric retention tablets using the convenient methods of dry blending and direct compression, which are widely used in pharmaceutical industry. When the tablet was compressed using only superporous hydrogel powders, it disintegrated during swelling in water. By adding gelatin and tannic acid as excipients, the tablets could keep the original shape without disintegration during swelling. Because gelatin and tannic acid can form complexes, they can maintain the tablet scaffold. Since the carboxylic acid group in poly(acrylic acid) segments can also form complexes with tannic acid and hydrogen-bonding between themselves, the tablet comprised of P(AA-co-SPAK) SPH, gelatin and tannic acid is essentially an entangled IPN hydrogel structure in water, referred to herein as a superporous IPN hydrogel. Because the dried SPHs possess many micrometer scale interconnected pores, even after being ground into powders, these pores are still intact. The capillary effect generated by these pores renders the tablets rather fast swelling kinetics. A gastric retention tablet can swell up to 30 times of its original volume in 40 minutes while keeping its original conformation. Furthermore, the swollen tablet has advantageous mechanical properties. As shown in FIG. 3, it can withstand up to 16 Kpa compression stress before breaking. In low pH medium, the gelatin-tannic acid complexes become unstable, because of the degradation of gelatin. In such circumstances, CMC can be added to the formulation to prevent the tablet structure from collapsing during swelling.

With the superporous IPN hydrogel strategy, an excellent gastric retention platform can be generated. The active pharmaceutical ingredients can be dry blended with SPH powder, gelatin and tannic acid together, then direct compressed into monolithic matrix tablets. Alternatively, the active ingredients can also be compressed into a tablet core by itself, then press coated with the SPH powder, gelatin and tannic acid. In this way, the outer layer of gelatin-tannic acid modified SPIH will function only as a platform and the release kinetics will be controlled solely by the active ingredient core inside. Therefore, many potential therapeutic agents can be delivered in this way and diverse controlled release kinetics can be designed.

B. Chemoembolization Device and Occlusion Devices

Chemoembolization is a therapeutic method to combine embolization with chemotherapy (115). Embolization therapy has been used to treat cancers for some time. The mechanism is to restrict the oxygen supply to the growing tumors by blocking the blood flow to the tumor site. Combining this with the chemotherapeutic agent, local delivery and low systematic toxicity can be realized. Anti-angiogenic compounds will also be incorporated in the device to overcome angiogensis, which is used by tumors to promote the growth of new capillary blood vessels (116,117). The superporous hydrogels can be used for chemoembolization effectively. A chemotherapeutic agent and an anti-angiogenic agent can be loaded into the superporous hydrogels. The toxic effect to tumors of the chemotherapy will be amplified by the hypoxia effect of the embolization. With improved elastic properties, superporous IPN hydrogels can fit better in blood vessels and provide better blocking results.

Superporous hydrogels can also be used to develop biomedical devices for treating aneurysms. After the size and shape of an aneurysm site is determined, a superporous hydrogel can be synthesized, which has the same shape and smaller size. Because of the properties of fast swelling and high swelling ratio, the hydrogel will swell at the aneurysm site and make the blood clot (117). Studies have shown that deposition of superporous hydrogels resulted in 95% aneurysm occlusion without parent artery compromise and inflammatory response. Further developments of new occlusion devices are also under investigation (117).

C. Other Applications

Since their invention, superporous hydrogels have been studied for various possible applications. For example, development of peroral peptide delivery systems using superporous hydrogels has been conducted (118–120). These novel drug delivery systems used superporous hydrogels and superporous hydrogel composite as the conveyor of incorporated model peptide drugs. By site-specific mechanical fixation of these so-called shuttle systems, peroral administration of peptide and protein drugs with specific release pattern can be achieved. The proper selection of the type and thickness of enteric-coating will make it possible to target this dosage form to any specific site in the small intestine or to the colon.

Superporous hydrogels have also been proposed as diet control aids, long term water reservoir in horticulture and hygienic products, and water sealing or caulking products in civil construction. With improved mechanical properties, the applications of superporous IPN hydrogels in these areas will become more and more practical.

The therapy of the present invention is carried out by administering a drug component together with a hydrogel material of the invention in any manner that provides effective levels of the two compounds in the body at the same time. All of the compounds concerned are orally available and are normally administered orally. However, oral administration is not the only route or even the only preferred route. For example, transdermal administration may be very desirable for patients who are forgetful or petulant about taking oral medicine. One of the drugs may be administered by one route, such as oral, and the other may be administered by the transdermal, percutaneous, intravenous, intramuscular, intranasal or intrarectal route, in particular circumstances. The route of administration may be varied in any way, limited by the physical properties of the drugs and the convenience of the patient and the caregiver.

It is particularly preferred, however, for administration of a single pharmaceutical composition. Such compositions may take any physical form pharmaceutically acceptable, but orally usable pharmaceutical compositions are particularly preferred. Such pharmaceutical compositions contain an effective amount of each of the compounds, which effective amount is related to the daily dose of the compounds to be administered. Each dosage unit may contain the daily dose of a drug, or may contain a fraction of the daily doses, such as one-third of the doses. The amounts of each drug to be contained in each dosage unit depends on the identity of the drugs chosen for the therapy, and other factors such as the indication for which the therapy is being given.

The inert ingredients and manner of formulation of the pharmaceutical compositions are conventional. All of the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the drugs in total, depending on the desired doses and the type of composition to be used. The amount of the compounds, however, is best defined as the effective amount, that is, the amount of each compound that provides the desired dose to the patient in need of such treatment.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acid contents of the stomach. Such formulations are created by coating a solid dosage form with a film of a polymer insoluble in acid environments and soluble in basic environments. Exemplary films are cellulose acetate phthalate, polyvinyl acetate phthalate, hydroxypropyl methylcellulose phthalate and hydroxypropyl methylcellulose acetate succinate.

Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

When it is desired to administer the combination as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Other, more complicated patch compositions are also in use, particularly those having a membrane pierced with innumerable pores through which the drugs are pumped by osmotic action.

V. Conclusion

Improvements in mechanical properties and elasticity of superporous hydrogels using the mechanism of interpenetrating polymer networks are demonstrated for the present invention. Capillary uptake of fluids has been proposed as the mechanism of swelling for the SPH since they were first created. To improve the mechanical properties of superporous hydrogels while preserving this rapid swelling kinetics, a strengthener polymer network is synthesized penetrating inside the pores of superporous hydrogels. The swelling speed of the resultant various types of superporous IPN hydrogels is still fast, indicating the interconnected pore structure is not blocked by the strengthener polymer networks. A limit on volume swelling ratio is observed for various types of superporous IPN hydrogels. The existence of the scaffold-like polymer network enforces a restraint on the volume change upon hydrogel swelling, which is essentially the extension limit of the strengthener polymer networks in water.

Mechanical strength is significantly increased by incorporating such polymer networks. Both the compression strength and elasticity are improved significantly. Highly elastic superporous IPN hydrogels have been developed using naturally available polysaccharides as strengtheners. The significantly improved elasticity is found mainly due to changes in the microscopic structures of superporous IPN hydrogels. When the polysaccharide networks are formed along the pore walls of superporous hydrogels, the superporous IPN hydrogels are more flexible and stretchable. When the polymer networks are formed between and connecting the pore walls of superporous hydrogels like the polyacrylonitrile network or around the pore walls like CMC ionotropically network, the resulting superporous IPN hydrogels are stiffer, and more resistant to stretch. Depending on the type of polysaccharide strengtheners used, the superporous hydrogel hybrids can be stretched to about 200% to 300% elongation of their original length. Such elasticity has never been reported for any hydrogels.

Because of these significant improvements in mechanical properties and elasticity, the potential applications of SPHs are greatly expanded. Superporous hydrogels with improved mechanical properties can be designed as gastric retention devices as initially proposed, but also can be applied in many other fields including biomedical engineering, agriculture, civil engineering, etc. Applications of superporous IPN hydrogels will be further increased as more and more people in different research areas become aware of the unique swelling and superior mechanical properties of SPIHs.

The following examples are presented in order to illustrate practice of the present invention for purposes of clarification; they do not limit the invention.

EXAMPLES

I. Conventional Copolymer-based SPHs

Conventional (unstrengthened) polymer-type SPHs (see U.S. Pat. No. 6,271,278) were prepared using two or more monomers to form the base hydrogel polymer. Variations in copolymer composition and the effects of synthetic method on swelling behavior and mechanical strength were examined.

Example A
AAm-AAc-NaAAc(50:25:25)-BIS Copolymer.

The amount of 25 parts of monomer mixture composed of 50 w/v % acrylamide (AAm, Aldrich, Milwaukee, Wis.) and 50 w/w % acrylic acid (AAc, Aldrich) aqueous solution was mixed with 5.5 parts of 2.5 w/v % N,N'-methylenebisacrylamide (BIS, Aldrich) crosslinking agent, 2.5 parts of 10 w/v % Pluronic F127 (BASF, Gurnee, Ill.) foam stabilizer, and 1 part of 20 v/v % N,N,N',N'-tetramethylethylenediamine (TMEDA, Aldrich) aqueous solution as reductant. The reactant stock solution was placed in a borosilicate glass culture tube (Coming, New York, N.Y.) with the dimensions of 10 mm (ID)×160 mm (L). The acid monomer was then partially neutralized to a pH of 5.1 by addition of 50 w/v % aqueous NaOH solution.

The polymerization reaction was initiated by adding 60 $\mu$l of 20 w/v % ammonium persulfate (APS, Aldrich) as the oxidant to the reaction mixture. The foaming reaction was triggered by addition of sodium bicarbonate (SBC, J. T. Baker, Phillipsburg, N.J.), while the mixture was vigorously stirred with a spatula. Further polymerization reactions were conducted at room temperature for different monomer compositions of AAm to AAc weight ratios of 1/0, 0.8/0.2, 0.6/0.4, 0.4/0.6, 0.2/0.8, and 0/1. The water residing in the SPHs was extracted with ethanol and the products were stored in the convection oven for complete drying.

The SPHs were cut to 5–10 mm length with a weight of 0.15–0.2 g and samples were placed in distilled water. The sample was weighed periodically at room temperature until no weight change was observed. The equilibrium swelling ratio was determined as the water uptake weight divided by the dry polymer weight. A bench comparator (Ames, Waltham, Mass.) was used to measure the compressive strength of water-swollen SPHs. Samples were placed on the bench comparator, and a series of cylindrical weights were applied to the top of each sample. The ultimate compressive strength was determined as the applied weight divided by load contacting area when samples were broken.

Example B
SPAK-AAc-NaAAc(50:25:25)-PEGDA Copolymer

The reaction in Example A was repeated substituting AAm with SPAK monomer and using a different crosslinker. An amount of acrylic acid aqueous solution was partially neutralized to the acrylate with NaOH solution to make a final pH of 5.3 and a final monomer concentration of 50% (v/v) of total acrylic acid and acrylate. The monomer mixture was combined with 60 $\mu$l Poly(ethylene glycol) diacrylate (PEGDA, F.W. 302) (crosslinker) dissolved in 1.85 ml of HEA. After the mixture became clear, 1.85 ml of 50% acetic acid (foaming agent) was added with stirring. Finally, 1.85 ml of 50% aqueous potassium salt of 3-sulfopropyl acrylate (SPAK) monomer was added dropwise to the monomer mixture with stirring.

The SPH was prepared in a plastic test tube (17 mm in diameter×100 mm in length) by mixing 0.56 ml of monomer mixture, 50 $\mu$l of 10% Pluronic F127, 30 $\mu$l of 20% TMEDA, 40 $\mu$l of 20% APS and water to make a final volume of 1 ml. The test tube was shaken to mix the solution after each ingredient was added. Finally 23 mg NaHCO$_3$ was added and the whole solution was vigorously stirred using a spatula for 30 sec to accelerate foaming and to evenly distribute the gas bubbles. The superporous hydrogel was then cured at room temperature for 10 min. The final monomer concentration in this preparation was about 37% (w/v) and the PEGDA concentration was approximately 0.6 mol % of the total monomers. The foam volume expansion after gelation ranged from 4 to 5 times of the volume of the feed monomer mixture.

Example C
SPAK-AAc-NaAc(50:25:25)-PEDGA Copolymer+Disintegrant

Example B was repeated but with a disintegrant, Ac-Di-Sol, also provided in the formulation. The acrylic acid was partially neutralized with NaOH solution to make a final pH of 5.3 and the final monomer concentration of 50% (v/v) of total acrylic acid and acrylate. The monomer mixture was prepared by dissolving 60 $\mu$l Poly(ethylene glycol) diacrylate (PEGDA, F.W. 302) in 1.85 ml of HEA. After the mixture became clear, 1.85 ml of 50% acetic acid was added with stirring. Then 1.85 ml of 50% aqueous SPAK was added to the mixture dropwise with stirring.

The SPH was prepared in a plastic test tube (17 mm diameter×100 mm length) by mixing 0.56 ml of monomer mixture, 40 mg of Ac-Di-Sol, 50 $\mu$l of 10% Pluronic F127, 30 $\mu$l of 20% TMEDA, 40 $\mu$l of 20% APS and water to make a final volume of 1 ml. The test tube was shaken to mix the solution after each ingredient was added. APS was added last. Before APS addition, the mixture was equilibrated for a few minutes. Finally, 23 mg NaHCO$_3$ was added and the whole solution was vigorously stirred using a spatula for 30 sec to accelerate foaming and to evenly distribute the gas bubbles. The superporous hydrogel was then cured at room temperature for 10 min. The final monomer concentration in this preparation was about 37% (w/v) and the PEGDA concentration was approximately 0.6 mol % of the total monomers. The foam volume expansion after gelation ranged from 4 to 5 times of the volume of the feed monomer mixture.

II. Primary Approaches to SPIHs

A. The Alginate Approach

Example 1
AAm-BIS+alginate-Ca$^{2+}$ Strengthener

500 $\mu$L of AAm (Sigma, A-8887) solution (50wt %) was poured into a test glass tube (11.0 mm I.D., 13.0 mm O.D., 100 mm H.). 100 $\mu$L of 1.0 wt % BIS (Sigma, M-7256) was added and shaken. To this combined monomer and crosslinker solution, 50 $\mu$L of 10.0 wt % foam stabilizer (BASF, Pluronic® F-127) was added and shaken well. To promote foaming of this formulation, 50 $\mu$L GAA (Mallinckrodt, V194) was added and readily dispersed to make a homogeneous formulation. Before adding the components of the redox system, i.e., after combining AAm, BIS, Pluronic® F-127 and GAA, 1500 $\mu$L of a 2 wt % aqueous solution of sodium alginate as strengthener (Polysciences Inc, 2090) was added. After shaking and mixing well for 1 min., to initiate the polymerization at room temperature of 26° C., a couple of 20 wt % TMEDA (Aldrich 41,101-9) and 20 wt % APS (Aldrich 21,558-9) was used as the redox initiating system in an amount of 50 $\mu$L each. First, TMEDA was added and shaken well, and then APS added after 30 sec. All additions were made with 200–1000 $\mu$L and 5–50 $\mu$L micropipettes.

To determine the proper addition of SBC (Aldrich 34,094-4), it was reasonable to find the temperature/time profile of the reacting mixture. With the thick solutions of these formulations, SBC addition time is not as critical as for thin or dilute solutions of polymerizing systems. So after 30 sec, 30 mg SBC was added and dispersed well using spatula until a homogeneous foaming composition was obtained. After 5.0 min., by which the reaction temperature declined, 2 ml of ethanol (Pharmaco) was poured over the foam surface to help stabilize the foam structure and to remove the foam from the tube.

The foam was immediately put into a 30 wt % aqueous $CaCl_2$ (Mallinckrodt 4225) solution. The foam was swollen in this treating medium to its equilibrium swelling capacity. After 30 min, the swollen foam was taken out of the treating medium, thoroughly washed with fresh DW and put into EtOH for dehydrating until solid, brittle and hard feeling foam was obtained. To be dried out, the dehydrated foam was placed in an oven at about 60° C. overnight.

The dried sample was examined for its swelling properties in DW. It swelled fast like normal non-treated SPH just in 1–3 min time to its maximum equilibrium swelling, which was found around 40–50 g/g of the active swellable material (based on AAm network). The swollen foam was significantly resistant to stretching, compressing and bending stresses.

With this formulation, all ingredients were added under vigorous shaking (rpm #10) over a high-speed shaker. Under such circumstances, the following conditions should be met in order to prepare successful superporous hydrogels. The height of the whole reacting mixture is about 3 cm before reaction; height of the whole reacting mixture under shaking is around 7 cm and the height of the foam after gel formation is about 7 cm.

Example 2

AAm-BIS+alginate-$Ca^{2+}$ Strengthener

Example 1 was repeated except that 600 μl AAm (50 wt %) was used instead. Weight swelling capacities of 50–57 g/g (based on active swellable material) was obtained.

Example 3

AAm-EBA+alginate-$Ca^{2+}$ Strengthener

Repeat of Example 1, except using 600 μl AAm (50 wt %), 100 μl of 1.09 wt % EBA (Aldrich 35,887-8, equivalent to 1 wt % BIS solution) and 1500 μl of 3 wt % low viscous alginate (Sigma A2158). The product was removed from the tube using ethanol and directly placed into 10 wt % calcium chloride solution for 30 min, thoroughly washed with DW and dehydrated in ethanol. After drying to constant weight (60° C. for 2 hr), the weight swelling capacity based on the active swellable material was found in the range of 67–71 g/g and elasticity was medium. Using a more thermally stable crosslinker (EBA against BIS), the as-prepared superporous hydrogel can experience a thermal treatment step to attain higher swelling properties and more conversion of monomer to polymer. The higher swelling capacity of the EBA-crosslinked samples compared to BIS-crosslinked ones can at least be attributed to greater conversion of monomer to polymer and to better SPH homogeneity.

Example 4

AAm-EBA+alginate-$Ca^{2+}$ Strengthener

Repeat of Example 3, except that 175 μl EBA and 1700 μl of 2 wt % Algin (Polysciences Inc 2090) were used instead. All ingredients were added in the order of AAm, EBA, F1 27, GAA, Algin, TMEDA, APS and SBC. SBC was added 1.30 min after APS addition. After temperature decline, the sample was heated for 15 min at 75° C., then placed into calcium chloride solution (30 wt %) for 30 min., thoroughly washed with DW, dehydrated in ethanol and dried in an oven at 60° C. overnight. A total of 5 samples showed average weight swelling of about 54 g/g of the active swellable material. The average volume-swelling ratio was obtained around 8.6 that indicate 2.04 increase in each SPH dimension. An optimized ratio of alginate to AAm was found to be around 11.2 wt %.

Example 5

AAm-EBA-PVOH+alginate-$Ca^{2+}$ Strengthener

While keeping the final foam height constant, the reaction mixture volume was increased by adding inert viscous diluents like PVOH and CMC solutions into the alginate-modified sample. Into the control formulation consisting of 600 μl AAm (50 wt %), 175 μl EBA (1.09 wt %), 200 μl F127 (10 wt %), 1700 μl algin (2 wt %, Polysciences, Inc; 2090), 40 μl GAA, 50 μl TMEDA (40 v/v %), 50 μl APS (20 wt %) and 30 mg SBC, 750 μl of 6 wt % PVOH (Aldrich 36,306-5) was added. All ingredients were added in the order of AAm, EBA, F127, GAA, Algin, PVOH, TMED, APS and SBC. SBC was added 1.30 min after APS addition. After temperature decline, the sample was heated for 15 min at 60° C. then placed into calcium chloride solution (30 wt %) for 30 min. It was thoroughly washed with DW, dehydrated in ethanol and dried in an oven at 60° C. overnight.

Example 6

AAm-EBA-CMC+alginate-$Ca^{2+}$ Strengthener

Repeat of Example 5 except that 750 μl of 2 wt % CMC (Sigma 9481) was used instead of PVOH solution. A weight swelling ratio of about 64 g/g based on the active swellable material was attained. This value is equivalent to about 2.1 times increase in each dimension.

Example 7

AAm-TMPTA+alginate-$Ca^{2+}$ Strengthener

Example 1 was repeated, except for use of 600 μl AAm (50 wt %), 1700 μl algin (2 wt %) and 150 μl TMPTA (Aldrich 24,680-8; 0.192 g in 10 cc acetone (Aldrich 17,997–3)) as a chemical crosslinker. The SPH formed had a weight-swelling ratio of about 54 g/g.

Example 8

AAm-EBA+alginate-$Ca^{2+}$ Strengthener

Increased monomer and modifier concentrations: 800 μl AAm (50 wt %), 200 μl EBA (1.09 wt %), 200 μl F127 (10 wt %), 2500 μl algin (2 wt %), 40 μl GAA, 50 μl TMEDA (40 v/v %), 50 μl APS (20 wt %) and 30 mg SBC. SBC was added 1.30 min after APS addition. The foam was placed into an oven at 75° C. for 15 min. The same treatment and work up were done as in Example 1. A weight-swelling ratio of about 60 g/g was attained for this very tough SPH.

Example 9

AAm-EBA+alginate-$Ca^{2+}$ Strengthener with Induced Grafting.

As in Example 1, 800 μl AAm (50 wt %), 200 μl EBA (1.09 wt %), 200 μl F127 (10 wt %), 2000 μl algin (2 wt %), 10 μl cerium ammonium nitrate (Aldrich 21,547-3; 0.6 g in 6 ml 1N $HNO_3$), 40 μl GAA, 50 μl TMEDA (40 v/v %), 50 μl APS (20 wt %) and 30 mg SBC were combined. SBC was added 1.30 min after APS addition. The foam was placed into an oven at 75° C. for 15 min. The same treatment and work up as in Example 1 were carried out. A weight-swelling ratio of about 42 g/g was attained for this very tough SPH. (CAN induces grafting of monomers onto a growing polymer chain.)

Example 10
AAm-DADMAC-EBA+alginate-$Ca^{2+}$ Strengthener

As in Example 1, 800 µl AAm (50 wt %), 200 µl EBA (1.09 wt %), 200 µl F127 (10 wt %), 2000 µl algin (2 wt %), 100 µl DADMAC as cationic monomer (Aldrich 34,827-9; 65 wt % solution in water), 40 µl GAA, 50 µl TMEDA (40 v/v %), 50 µl APS (20 wt %) and 30 mg SBC were combined. SBC was added 1.30 min after APS addition. The foam was placed into an oven at 90° C. for 15 min. The same treatment and work up as in Example 1 were carried out. Although a weight-swelling ratio of about 50 g/g was attained, the increase in each dimension was about 2.1 times and the pore structure was perfect.

Example 11
AAm-DADMAC-EBA+alginate-$Ca^{2+}$ Strengthener

As in Example 10, 600 µl AAm (50 wt %), 175 µl EBA (1.09 wt %), 200 µl F127 (10 wt %), 1700 µl algin (2 wt %), 100 µl DADMAC (65 wt % solution in water), 40 µl GAA, 50 µl TMEDA (40 v/v %), 50 µl APS (20 wt %) and 30 mg SBC were combined. SBC was added 1.30 min after APS addition. The same treatment and work ups as in Example 1 were carried out except the heating step. The weight-swelling ratio was 54 g/g and showed around 2.1 increase in each dimension. Foam formation in the presence of DADMAC is perfect.

Example 12
AAm-EBA+alginate-$Ca^{2+}$ Strengthener

Increased amount of swellable material: 1200 µl AAm (50 wt %), 250 µl EBA (1.09 wt %), 200 µL F127 (10 wt %), 2500 µl algin (2 wt %), 40 µl GAA, 50 µl TMEDA (40 v/v %), 50 µl APS (20 wt %) and 30 mg SBC were combined as in Example 8. SBC was added 2.0 min after APS addition. The foam was heated at 75° C. for 15 min. The same treatment and work ups as in Example 1 were carried out. Regardless of the weight-swelling ratio of about 40 g/g, 2.2 times increase in each dimension was attained. Full swelling capacity was reached by about 1 hr for this very tough SPH.

Example 13
AAm-EBA+alginate-$Ca^{2+}$ Strengthener

1600 µl AAm (50 wt %), 200 µl EBA (1.09 wt %), 200 µl F127 (10 wt %), 2700 µl algin (2 wt %), 40 µl GAA, 50 µl TMEDA (40 v/v %), 50 µl APS (20 wt %) and 30 mg SBC were combined as in Example 12. SBC was added 2.15 min after APS addition. Foam was heated at 75° C. for 15 min. The same treatment and work ups as in Example 1 were carried out. Regardless of the weight swelling ratio of about 41.5 g/g, 2.2 times increase in each dimension was attained. The full swelling capacity can be reached in about 1 hr.

Example 14
AAm-BIS+alginate-$Ca^{2+}$ Strengthener+Glutaraldehyde.

Modification of alginate with glutaraldehyde was examined: Example 1 was repeated except 1750 µL of medium viscous sodium alginate (2 wt %) was used. The sample experienced a 2 hr treatment in calcium chloride solution (30 wt %) followed by treatment in glutaraldehyde (Fisher Chemicals G 151-1) solution for 44 hr. In order to block the aldehyde groups, the crosslinked sample was placed into glycine (Mallinckrodt 7728) solution (5 wt %). The SPH changed in color from a pale yellow to strong yellow, orange and finally red-brown (cherry) after 1 hr soaking in glycine, then was washed with water and dehydrated in ethanol. A weight-swelling ratio of about 51 g/g and a fast swelling time (1–3 min to reach the full swelling capacity) was attained.

Example 15
AAm-BIS-dextran+alginate-$Ca2+$ Strengthener+Glutaraldehyde.

The inclusion of dextran in polyAAm crosslinked with N,N'-(1,2-dihydroxyethylene) bisacrylamide (DHE-BA) has been studied in elastomeric gels (97).

Example 14 was repeated except 750 µL of aqueous dextran (Sigma D-5501) solution (20 wt %) was added. The same treatment and work ups as in Example 14 were carried out. The dextran-modified sample showed a noticeable decrease in its swelling capacity (about 40 g/g) and rate (15 min to reach the full swelling capacity). This can be accounted for in terms of greater chemical crosslinking for the dextran-containing sample. A higher crosslink density with the dextran-modified sample was indicated by brittleness in its swollen state.

Example 16
AAm-BIS+alginate-$Ca^{2+}$ Strengthener+Acid Bath

Example 1 was repeated except that the as-treated alginate modified SPH (after alginate crosslinking with calcium cations and repeated washing) was placed into an acidic medium of pH 1 (using HCl; Baker). After 2 hrs, the gel strength improved to some extent. Treatment of the acidified samples in $CaCl_2$ solution and acidifying the $CaCl_2$-treated samples showed nearly the same results.

Interchain complex formation was also examined as a replacement for crosslinker. An alginate-modified AAm-based SPH was made as in Example 1 and placed in Poly(diallyldimethylammonium chloride) (Aldrich 40,902-2) solution. Gel strength was increased to some extent but ionic gelation (with $Ca^{2+}$ ions) seemed to be much more effectual than interchain complex formation via cationic DADMAC bridges.

Example 17
Treatment with $Cu^{2+}$ and $Fe^{3+}$ Ions

Although a variety of calcium-containing salts can be used to crosslink the alginate chains, the most preferred was anhydrous calcium chloride. This kind of gelation (ionotropic) was performed using copper cations (as in cupric sulfate, 30 wt % in water) and iron cations (as in iron chloride hexahydrate ($FeCl_3.6H_2O$), 10 wt % in water).

Accordingly, alginate-modified polyacrylamide (PAAm) SPH, as in Example 1 (containing 1500 µL of 3 wt % L-grade alginate), was treated in 10 wt % iron chloride solution for just a couple of minutes. The treated products were red-brown in color possessing high toughness and stiffness. With other experiments, the alginate amount was decreased to 750 and 500 µL. The corresponding products obtained with 1500, 750 and 500 µL of alginate solution showed very high strength, high strength, and reasonable strength, respectively. Features of this kind of treatment were as follows:

SPH skin is very porous.
Water absorption is very fast.
Absorption behavior is sponge-like and mostly capillary in nature.

This observation can be accounted for in terms of the crosslinker effect on both PAAm and alginate chains. Aqueous polyAAm solution itself can also be gelled in the presence of iron chloride. The high resiliency obtained using 750 µL of alginate treated with iron chloride is presumably due to simultaneous crosslinking of the two polymer systems.

B. The Chitosan Approach

The formulation design of the alginate approach can be successfully employed in other approaches. Acidified chitosan solution was prepared in water containing 1 v/v % GAA.

Example 18
AAm-BIS+chitosan-TPP

600 µL AAm (50 wt %), 100 µL BIS (1 wt %), 200 µL F127 (10 wt %) were mixed well in a glass culture tube (100 mm H and 11 mm ID). Then 1000 µL of as-prepared chitosan (Aldrich; 44,887-7) solution (3 w/v %) was well mixed and shaken, followed by addition of 50 µL GAA, 50 µL of TMEDA (20 wt %) and 50 µL of APS (20 wt %), which were well shaken in a glass test tube (13×100 mm). SBC (40 mg) was added 1.15 min after APS addition. The exotherm appeared after 2 min time and the temperature gradually increased. After 10 min time, the foams were removed from the tube using 2 ml ethanol and put directly into pentasodium tripolyphosphate (TPP, Sigma; T-5883) solution ((pH= 1; 10 wt %) for 20 min. for 2 hrs. Treated samples were washed several times with fresh DW to remove residual TPP and any nonreacted materials, followed by dehydration using fresh batches of ethanol. Dehydrated foams were dried in an oven at 60° C. overnight to constant weight. An optimized ratio of chitosan to AAm was found to be around 10 wt %.

All samples showed nearly similar swelling behavior (very rapid water absorption in about 10–30 sec), high swelling capacity of 35–45 g/g (equivalent to about 2 times increase in each SPH dimensions), significant elasticity and extensibility of the swollen material, sustained elasticity for a long period of time (at least 1 week in DW) and the same physical properties (homogeneity, foam height). The product is extensible and very resistant to tear, tensile and compressive stresses.

Example 19
AAm-BIS+chitosan-TPP

Example 18 was repeated, except that the pH of the TPP solution was decreased to 5 using aqueous HCl (36.5 wt %). A very strong and elastic SPH foam was obtained. Since the strength dependence on pH was found very critical, other pHs down to 3 and 1 were also examined. Chitosan-modified foams treated in these crosslinker solutions all showed very high elasticity and the best result was obtained with the TPP solution at a pH range of 1–2.

Example 20
AAm-BIS+chitosan-TPP

As with the previous examples, chitosan concentrations (3 w/v %) of 500, 1000 and 2000 µL were also examined. As with the alginate approach, an optimum chitosan concentration and conditions of synthesis were identified. This optimum value was in the range of 500–1200 µL (based on 500 µL of 50 wt % AAm) and most preferably around 1000 µL.

C. Carboxymethylcellulose (CMC) Approach

Carboxymethylcellulose solution can make strong beads in contact with aqueous $FeCl_3$ solution. This feature was exploited to increase the elasticity of water-swollen superporous hydrogels. Aqueous solutions of CMC were prepared and added into AAm-based SPH formulations. The prepared SPHs were treated in ferric chloride solutions. Spongy SPHs of very high strength were prepared. Swelling and strength properties are remarkable.

Example 21
AAm-BIS+CMC-$Fe^{3+}$ Strengthener

A 2 wt % aqueous solution of CMC (Sigma; 9481) (pH of 7) was prepared having the same viscosity as 2 wt % aqueous solution of medium viscous grade of sodium alginate (Sigma; A-2033). An aqueous solution of $FeCl_3$ hexahydrate (Sigma; F-2877) (10 wt %, pH of 2) was also prepared. 600 µL AAm (50 wt %), 100 µL BIS (1 wt %), 200 µL F127 (10 wt %), 1500 µL CMC (2 wt %), 40 µL GAA, 50 µL TMEDA (40 v/v %) and 50 µL APS (20 wt %) were added in turn and mixed well in a glass culture tube (100 mm H and 11 mm ID). SBC was added 30 sec after APS addition. The foam obtained was placed into an iron (III) chloride solution (10 wt %) for 1 hr. A very strong sample was obtained, which can be stronger than a comparable alginate-modified sample. The compression modulus appears to be very high.

Example 22
AAm-BIS+CMC-$Fe^{3+}$

Example 21 was repeated, except that the CMC concentration was reduced to 500 µL. After temperature decline, samples were placed into iron (III) chloride solution (10 wt %) for an hour, then thoroughly washed with DW, dehydrated in ethanol and dried in an oven at 60° C. overnight. A total of 5 samples showed average weight swelling of about 40 g/g of the active swellable material. The average volume-swelling ratio was around 8.0, which indicates about 2 times increase in each dimension. Again, a very strong and elastic highly swellable sample was obtained. The preferred CMC (2 wt %) concentration based on 600 µL AAm (50 wt %) was found to be in the range of 100–2000 µL. More preferred and most preferred ranges are 300–1200 µL, and 500–750 µL, respectively. An optimized ratio of CMC to AAm was around 3.3 wt %.

Example 23
CMC Incorporated Alginate-PAM Superporous IPN Hydrogel

Into the solution consisting of 600 µL AM (50%), 175 µL BIS (1%), 200 µL PF127 (10%), 1700 µL 2% sodium alginate (Polysciences Inc, 2090), 40 µL glacial acetic acid, 50 µL TEMED (20%), 50 µL APS (20%) and 30 mg sodium bicarbonate, was added 750 µL of 2 wt % CMC (Sigma 9481). All ingredients were added in the order of AM, BIS, PF127, GAA, Alginate, CMC, TEMED, APS and SBC. The SBC was added 1.30 min after APS addition. The same treatment and work ups were done as in Example 1. The composition ratios of alginate and CMC to AM were 11.3% and 5%, respectively.

D. Pectin Approach

A 3 wt % aqueous solution of pectin (Sigma; P-8471) (3 g) was prepared in 97 g of DW. A 10 wt % aqueous solution of anhydrous calcium chloride (Mallinckrodt; 4225) (10 g) was also prepared using 90 g DW. Droplets of pectin solution can instantaneously be gelled as a bead when placed in contact with $CaCl_2$ solution but the beads are found not to be as strong as $Ca^{2+}$-crosslinked alginate beads. The following formulation was attempted using pectin as a polysaccharide modifier.

Example 24
AAm-BIS+pectin-$Fe^{3+}$ Strengthener

500 µL AAm (50 wt %), 100 µL BIS (1 wt %), 200 µL F127 (10 wt %), 1500 µL pectin (3 wt %), 50 µL GAA, 50 µL TMEDA (20 wt %), 50 µL APS (20 wt %) were added and mixed well in a glass culture tube (100 mm H, 11 mm ID). SBC (30 mg) was added 45 sec after APS addition. In a total time of 5 min, a well-structured superporous structure was obtained. The SPH was removed from the tube using ethanol and placed directly into 10 wt % aqueous $CaCl_2$ solution at room temperature for 30 min. The effect of pectin on gel strength and elasticity of the SPH was certain but not as much as obtained with the alginate approach. This difference can be accounted for in terms of bead strength and consistency in ionic medium. Compared to pectin, alginate solution makes stronger beads in calcium chloride solution. Conclusion on Ionic Gellation: Based on extensive study, a simple rule of thumb was found to make strong and elastic SPHs through application of ionotropic gelation on polysaccharides:

1-The efficient matrix should be a polysaccharide.
2-The polysaccharide should make a strong bead once in contact with ionic gelation medium.

This rule was confirmed for a number of gel forming materials (saccharides and non-saccharides) and three approaches were finally obtained that led to superporous hydrogels of very high gel extensibility and swelling properties:

1-Alginate in the presence of calcium ions (using calcium chloride).
2-Chitosan in the presence of phosphate ions (using TPP).
3-Carboxymethylcellulose in the presence of iron cations (using iron chloride).

All three make strong beads in the presence of their corresponding crosslinking medium. According to this invention, any other polysaccharides displaying the same behavior in the presence of ions, can presumably be useful to prepare highly elastic superporous hydrogels.

E. Cryogel Approach

In a beaker, PVOH (M.W. 124000–186000, 99% hydrolyzed; Aldrich; 36,306-5) was dispersed in DW and heated over a water bath for 45 min at temperature of 80° C. under magnetic stirring until a clear viscous solution was obtained. Different aqueous PVOH solutions (7, 13.3 and 16.6 wt %) were prepared and 3 ml of each was placed into a glass culture tube (100 mm L, 11 mm ID). Glass tubes were covered and sealed by aluminum foil and parafilm and placed into a commercial freezer at −12° C. for 24 hr, then placed in a plastic bag containing crushed ice for 12 hr in a general refrigerator. Care was taken to keep the frozen materials at about 0° C. in order to attain extended thawing. With different PVOH solutions, soft, tough and very tough hydrogels were respectively obtained after cryotreatment.

Example 25
AAm-BIS+PVOH-lowT

In this preparation, 500 µL AAm (50 wt %), 100 µL BIS (1 wt %), 200 µL F127 (10 wt %), 40 µL GAA, 1500 µL of 10 wt % PVOH (MW 124000–186000, 99% hydrolyzed; Aldrich; 36,306-5) solution, 50 µL of TMEDA (20 wt %) and 50 µL of APS (20 wt %) were added and shaken well in a glass culture tube (100 mm H and 11 mm ID). SBC (30 mg) was added 30 sec after addition of APS and shaken well. After removing from the tube using ethanol, the sample was placed into a commercial freezer at a temperature of −12° C. for 24 hr and then into a refrigerator at the temperature of 8° C. for 12 hr. An appreciable change in elasticity appeared. The sample was almost transparent, while having a very high rate of absorption, elasticity and extensibility like a rubber. This sample showed a high strength value after swelling in distilled water.

Example 26
HEA-BIS+PVOH-lowT

500 µL HEA (Aldrich; 29,281-8), 500 µL DW, 100 µL BIS (1 wt %), 200 µL F127 (10 wt %), 1000 µl PVOH (10 wt %), 50 µL AA, 50 µL TMEDA (40 v/v %) and 50 µL APS (20 wt %) were added and shaken well in a glass culture tube (100 mm H, 11 mm ID). SBC (30 mg) was added 2.50 min after APS addition. Precipitation occurs if the HEA is directly added to PVOH solution. Foams were kept in the commercial freezer (−12° C.) for 48 hr and then in the refrigerator (8° C.) for 12 hr. An elastic SPH was obtained.

Example 27
HEA-BIS+PVOH-lowT

Example 25 was repeated but DW was removed and 1500 µL PVOH (10 wt %) was added instead. SBC (30 mg) was added 45 sec after APS addition. Very well structured foams were obtained. Glass tubes were covered with aluminum foil and sealed with parafilm, then put into a commercial freezer (temperature of −12° C.) for 24 hrs, followed by placement into a plastic bag containing crushed ice at 0–1° C. for 12 hr (while in refrigerator). Samples were removed from the tubes without using ethanol (breaking the tubes) and hung in an oven at 70° C. to be dried out to constant weight. Equilibrium absorption of about 30 g/g (equivalent to two-fold increase in each dimension) can be reached in seconds and gel strength was remarkable. One exclusive advantage of the cryogel approach was that the final dehydrated (in ethanol) and dried (in oven) product is soft and rubbery and can be handled very easily. An optimized ratio of PVOH to HEA was found around 17.1 wt %.

Example 28
HEA-BIS+CMC-PVOH-lowT

With this example, simultaneous CMC and cryogel approaches were explored. 500 µL HEA, 100 µL BIS (1 wt %), 200 µL F127 (10 wt %), 50 µL GAA, 1000 µL combined solutions of CMC (2 wt %) and PVOH (10 wt %) as the volume ratios of 500/500, 200/800 and 800/200, 50 µL TMEDA (40 v/v %) and 50 µL APS (20 wt %) were used. The order of addition was AAm, BIS, F127, AA, CMC, PVOH, TMEDA and APS. All additions were done under vigorous shaking to ensure complete mixing. Finally, 30 mg SBC was added 45 sec after APS addition. With CMC addition, all mixtures were transparent, but once PVOH was added, the mixture turned from transparent to turbid. The higher the CMC concentration, the higher the transparency, but increased PVOH concentration led to increased turbidity and opacity of the reacting solution. All SPHs were well structured. The glass tube was covered with aluminum foil and parafilm and immediately put into a commercial freezer (−12° C.) for 24 hr, then into a plastic bag containing crushed ice (0–1° C.) for 12 hr (while in refrigerator). Cryogel-modified samples were ionotropically gelled upon treatment with 10 wt % $FeCl_3$ solution for 30 min. Higher modulus highly elastic superporous hydrogels were obtained in this way.

F. PEI Approach

Example 29
AAm-AAc-NaAAc(50:25:25)-BIS+PEI Strengthener

To the stock solution prepared as in Example A (using two different monomers), 15 wt % aqueous solution of highly branched PEI (weight average M.W. 750,000 g/mol, Aldrich) was added to obtain final PEI to monomer weight ratios of 2.5/100, 5/100, and 10/100, respectively.

Polymerization was conducted in a borosilicate glass culture tube (Corning, New York, N.Y.) in the dimension of 10 (ID)×160 mm (H) followed by adding 1.65 ml of stock solution and the predetermined amount of PEI aqueous solution in the culture tube. The pH of the stock solution was adjusted to 5.0 by adding 50 w/v % sodium hydroxide aqueous solution. After introduction of 60 μl of 20 w/v % APS solution, 80 mg of SBC was added. While the mixture was vigorously stirred with a spatula or vortex generator at room temperature, polymerization was completed in a few minutes. The products were stored in the convection oven for complete drying.

Results and Discussion: An increase in the PEI concentration led to a decrease in gelation time due to a reduction in the acidity of the reactant solution. The gelation time of unneutralized samples slightly decreased with AAc concentration for the same reason. The swelling ratio decreased with an increase in PEI concentration and the maximum swellings were observed around the AAc weight fraction of 0.4 for all PEI concentrations. Also, the swelling ratios of unneutralized SPHs were much lower than for neutralized ones, because the decrease of the fixed charge concentration reduced the ionic contribution to swelling pressure. The effect of PEI concentration on swelling behavior of unneutralized systems was the same as for neutralized ones. As expected, the swelling ratio also decreased with increasing crosslinking agent. The water sorption rate was considerably reduced by an increase in either the AAc or PEI concentration, presumably because an increased interaction between PEI and AM molecules reduced the observed pore sizes. Similarly, the swelling rate of unneutralized samples was somewhat higher than for neutralized ones, because the swelling rates are governed mostly by pore structures.

For neutralized samples, an increase of PEI concentration reduced equilibrium water uptake, but increased the mechanical strength. This plasticization effect was applied to the polymer system up to the AAc weight fraction of 0.5. The compressive strength, however, slightly decreased with decreasing water uptake when the AAc weight fraction was higher than 0.5, and even cracking occurred at a AAc weight fraction close to 1. The weakness of compressive strength at high AAc concentration is presumably due to swelling stress accumulated during water uptake. When this swelling stress is too high, the polymers are easily cracked by swelling force itself or by small external force. As the rate of stress relaxation decreased with increasing molecular entanglement and chemical or physical crosslinks, higher concentrations of AAc and PEI resulted in lower compressive strength, often accompanied by cracking. The compressive strength of unneutralized samples increased with increasing AAc concentration. As the water absorption content in unneutralized systems was not as high as that of neutralized ones, no high swelling stress was developed.

Conclusion: The swelling and mechanical properties of a series of SPHs of P(AM-co-AAc)/PEI IPNs were studied. Gelation time increased with increasing AAc or decreasing PEI concentration, as the redox type initiator activated more efficiently at more neutralized condition. For neutralized samples, the maximum equilibrium swelling ratio was observed at the PAAc weight fraction of around 0.4 for all PEI concentrations, but for non-neutralized samples the swelling ratio decreased monotonically with PAAc concentration. For both systems, the increase of PEI concentration decreased equilibrium swelling ratio because of the increasing physical interaction between PEI and PAAc molecules. Slower water absorption was observed for the samples composed of higher concentration of PEI or PAAc. The mechanical strength of swollen SPHs increased with PEI concentration for both systems. For non-neutralized samples the increasing AAc concentration led to increasing compressive strength by simple plasticization effect. For neutralized samples, however, it decreased the compressive strength, and even cracking occurred at PAAc concentration close to 1 because of the swelling stress accumulated during the water penetration.

G. PAN Approach

Example 30

PAN Penetrated P(AM-co-SPAK) Superporous IPN Hydrogel.

The following components were added sequentially to a 16 mm×100 mm glass test tube: 600 μL of 50% AM and 400 μL of 50% SPAK; 250 μL of 2.5% N,N'-methylenebisacrylamide (BIS) as a crosslinker; 50 μL of 10% Pluronic® F127 as a foam stabilizer; 20 μL of 50% acrylic acid; 30 μL of 20% ammonium persulfate (APS), and 30 μL of 20% N,N,N',N'-tetramethylethylenediamine (TEMED) as a redox initiator pair. The test tube was shaken to mix the solution after each component was added. 90 mg of SBC was added 90 seconds after adding the initiators, and the mixture was then stirred vigorously using a spatula to distribute $NaHCO_3$ evenly throughout the tube. After the gelation completes, the synthesized SPH was retrieved from the test tube by adding 2 mL of absolute ethanol (Pharmaco Product Inc.), and dried in an oven of 60° C. for 6 hours. The fully dried SPHs were cut into 1.5 cm discs, and immersed in 1.5 mL of 30% AN monomer solution for 6 hours. 30% (w/w) acrylonitrile (AN, Aldrich) monomer solution was made by dissolving 30 parts by weight of acrylonitrile in 70 parts by weight of aqueous 70% $ZnCl_2$ solution. Calculated amounts of 5(w/v) % potassium metabisulfite (PMBS, Aldrich, Wis.) and 5 (w/v) % APS were added to the soaked SPH samples. The polymerization was allowed to continue for 12 hours. When polymerization completed, the SPH discs were then thoroughly washed in deionized distilled water (DDW) to remove the unreacted species. Finally, the resulting SPIH was dehydrated using absolute ethanol and dried in an oven of 60° C. overnight.

H. Tannic Acid-Gelatin Approach

Example 31

Tablets Made by Tannic Acid-gelatin Modified P(AA-co-SPAK) SPIH

Acrylic acid was first neutralized with NaOH solution to achieve a 50% monomer solution (pH=5.1). In the preparation of PAA superporous hydrogel, 600 μL neutralized AA (50%), 400 μL of SPAK (50%) 6 μL poly(ethylene glycol) (200) diacrylate (PEGDA) (Polysciences Inc, PA), 50 μL PF127 (10%),40 μL of 20% TEMED (20%) and 40 μL of 20% APS were added and well shaken in a glass culture tube. SBC (40 mg) was added 30 sec after addition of APS and well shaken. After removing from the tube, the SPH sample was acidified by immersion in 0.5 M HCl for 6 hours. Dried poly(AA-co-SPAK) SPH samples were ground into powders using a grinding mill (IKA Works). Four parts of poly(AA-co-SPAK) SPH powder, 3 parts of gelatin (screened through 60 mesh US screen) and 3 parts of tannic acid (Aldrich, T3437) were blended, and the final blend was direct compressed into 500 mg flat faced tablets. CMC can be added to the formulation to improve the tablet swelling and mechanical properties in low pH (pH 1.0) medium. When CMC was added as excipient, the formulation was 40% of poly(AA-co-SPAK) SPH powder, 15% of gelatin, 15% of CMC, and 30% of tannic acid. The tablets of such formulation can swell by volume of more than 30 times in deionized distilled water and 14 times in pH 1.2 HCl solution. The swollen tablets can withstand an average 16 Kpa compression stress before breaking.

III. Secondary Approaches to SPHs Having Interpenetrating Networks

Example 32
Acidification.

300 μL of AAm (50 wt %), 200 μL AAc (Aldrich; 14,723-0) (50 v/v %), 150 μL NaOH (Aldrich; 22,146-5) (25 wt %), 500 μL DW, 100 μL BIS (1 wt %), 50 μL F127 (10 wt TMEDA (40 v/v %) and 50 μL APS (20 wt %) were added in order and shaken well in a glass culture tube (100 mm H and 11 mm ID). 30 mg SBC was added 1.15 min after APS addition. Acid (HCl) was added to the mixture until it was apparent that acidification was complete—when the swelling in acidic solution no longer continued, i.e., stable SPH dimensions were reached. This was found around 45 min for acidic solution of pH 1. The acidified sample was carefully washed in several batches of fresh DW up to the point that washing solution assumed a neutral pH, and then dehydrated in ethanol.

Dried SPHs (at 70° C. to constant weight) were examined for their swelling properties in acidic solution of pH 1 (0.1 mol HCl/l). They rapidly swelled up to about 50–70 times of their own weights and could maintain their elasticity just for a short period in water of various pHs. Elasticity and extensibility of SPH was significantly improved against a non-acidified sample. Attempts to increase the swelling capacity via decrease in monomer concentration (dilution with 2 and 3 times water) resulted in better swelling properties but at the cost of elasticity, extensibility and also foam heterogeneity. A useful upper limit of dilution with water was found around 1000 μL (for 500 μL monomer solutions).

Example 33
Impregnation with Poly(DADMAC).

SPH foams were prepared based on 300 μL AAm (50 wt %), 200 μL AAc (50 v/v %), 150 μL NaOH (25 wt %), 500 μL DW, 100 μL BIS (1 wt %), 50 μL F127 (10 wt %), 50 μL TMEDA (40 v/v %) and 50 μL APS (20 wt %). SBC (50 mg) was introduced 2.45 min after APS addition. A very well structured foam was obtained. Aqueous solutions of Poly (DADMAC) (Aldrich; 40,902-2) at different concentrations were prepared and examined as treating medium. The results are shown in Table 6.

TABLE 6

| Concentration | Control (20 wt %) | 10 wt % | 5 wt % | 2 wt % |
|---|---|---|---|---|
| Swelling time, min | Very long | 10 | 3 | 1 |
| Swelling capacity | Negligible | 3–12 | 14–25 | 27–32 |
| Consistency of the swollen material | Very tough | Tough | Soft | Very soft |

As shown in Table 6, reasonable swelling properties were attained at the lowest PDADMAC concentration. On the other hand, a high mechanical strength property appeared when high concentration of PDADMAC was employed. So, considering the consistency of the swollen material, the time required for complete swelling and reasonable swelling capacity, the PDADMAC solution of 7 wt % in water was chosen as an optimum PDADMAC concentration.

Example 34
PDADMAC Treatment.

Example 33 was repeated, except that the SPH foam was treated in both aqueous and methanol aqueous PDADMAC solutions (7 wt %). SPHs prepared were soaked in these solutions until their equilibrium swelling was reached. Samples were squeezed to remove residual PDADMAC and dried at 110° C. Swelling of the dried SPHs in DW was much better with methanol than aqueous solution of PDADMAC. Efficiency of this sort of treatment was found to be more or less dependent on PDADMAC concentration, crosslinker concentration, residence time in treating solution, drying time and temperature and also SPH dehydration procedure. Of course, copolymer composition (amide/acid ratio) can presumably affect the swelling and strength properties obtained using this kind of treatment. PDADMAC-treated SPHs showed different compressive properties in both their dimensions, so that compressive strength was observed higher in longitudinal than in transverse direction. PDADMAC-treated SPHs dehydrated in ethanol showed negligible strength. This observation is presumably due to ineffective interchain complexation at very dry conditions.

Example 35
Crosslinker Concentration.

Example 33 was repeated, except that the crosslinker concentration was changed to find its optimum value. At higher BIS concentration (330 μL), although elasticity was well improved, swelling capacity was considerably reduced. On the other hand, low strengths but high swelling properties were achieved at lower BIS concentration (50 μL). The optimum value was found around 220 μL. It seems that increased crosslinking density can assist attaining more efficient interchain complexation.

Example 36
Drying Conditions.

Example 33 was repeated, except drying conditions were changed. An as-prepared sample was immersed in 7 wt % methanol aqueous PDADMAC solution for about 20 min, followed by being squeezed to wash out residual PDADMAC. The treated sample was kept at room temperature of 25° C. for 72 hrs. The sample appeared as a solid after this long time. The solid sample showed first slow swelling behavior in water and then a very rapid kinetic to a high swelling value. It showed nearly similar high strength properties in both directions. It seems that interchain complex formation was much more facilitated upon drying at room conditions. Overall, the following optimum conditions were found with this type of treatment:

Using 220 μL aqueous BIS solution (1 wt %) as crosslinker.

Using 7 wt % methanol aqueous PDADMAC solution as treating medium.

No ethanol dehydration.

Residence time of about 20 min in treating medium.

No oven-drying just keeping the treated sample at room temperature for about 72 hr.

Considering all the above, two SPH samples (control and treated) were prepared based on Example 33. This kind of treatment resulted in about 60% decrease in swelling capacity (54 g/g against 22 g/g). The equilibrium swelling value was reached in a maximum of 5 minutes and significant compressive strength was attained in both directions.

Example 37
Introduction of Acrylic Latex into the SPH Formulation.

A typical acrylic latex (K-Mart; Acrylic Bonding Liquid, Sunny dry; bonding agent for cement and as replacement for water) was used as strengthener within an SPH formulation. It is presumably a dispersion terpolymer of different acrylates and acrylic acid (solid content of about 50 wt %) in water. The film cast from this dispersion was reasonably extensible and rubbery.

In a glass culture tube (100 mm H and 11 mm ID), 500 μL AAm (50 wt %), 500 μL DW, 100 μL BIS (1 wt %), 50 μL F127 (10 wt %), 50 μL GAA, 50 μL TMEDA (40 v/v %). and 50 μL APS (20 wt %) were placed. The acrylic latex was introduced into monomer solution in amounts of 150, 200, 300, 400, 500, 700 and 900 μL before redox pair addition. The optimum time for SBC addition was found to be dependent on latex concentration. Generally, according to individual temperature/time profile, SBC was added after a 1° C. rise in the reacting mixture. But, at low latex concentration, time or temperature schedule for SBC addition was much more critical than with higher latex concentrations. With latex concentrations higher than 200 μL, a 2, 3 and 4° C. temperature rise was tolerated in order to a successful SPH preparation.

The samples were dehydrated in ethanol and oven-dried in 110° C. for about 1 hr. A strong skin over the SPH surface was formed. The effect is noticeable. At high concentration (1/1 ratio of latex/AAm) the resulting product is very elastic with low swelling properties. The latex is stable at acidic medium and does not leach out of the product. An optimum result was obtained with the lowest latex concentration. The acidified swollen product is an extensible high strength material with swelling capacity of about 20–25 g/g and medium swelling rate of 40 min-1 hr. Strengthening effect of acrylic latex is nearly similar to PDADMAC approach. The former is not water-soluble but the latter is soluble in water.

Example 38
Treatment with Glycerol.

To improve their absorption kinetics, latex-modified SPH samples of Example 37 were treated with glycerol (Mallinckrodt; 7728) after a complete drying procedure. The dried samples were immersed in a mixture of glycerol/ethanol (volume ratio of 1/2) overnight, followed by dried to constant weight in the oven at 100–110° C. The samples were flexible after drying and the absorption rate was significantly increased. Glycerol showed a dual effect of improving the swelling rate and strengthening the product presumably as a result of additional crosslinking with residual carboxyls of the AAm-acrylic acid based SPH.

Example 39
Crosslinked Gelatin-PAM Superporous IPN Hydrogel.

An aqueous solution of gelatin (Sigma; G-6650) (same viscosity as low viscous grade sodium alginate solution) was prepared and added to the monomer solution of AM-based SPH formulation. 500 μL AM (50 wt %), 100 μL BIS (1 wt %), 200 μL PF127 (10 wt %), 50 μL glacial acetic acid were added and well shaken in a glass culture tube. 1000 μL gelatin solution (3 wt %), 50 μL TEMED (20 wt %) and 50 μL APS (20 wt %) were then added and well mixed. SBC (30 mg) was added 5 min after APS addition. Glutaraldehyde (Fisher Chemicals; G-151–1) solution (25 wt %) was used as post-crosslinker. The foam was removed from the tube using ethanol and placed into post-crosslinking medium overnight. The foam color first changed to orange and finally turned to deep brown after overnight. The foam was treated with glycine (Mallinckrodt; 7728) (5 wt % in water) to block the aldehyde groups, washed with DW, dehydrated in ethanol and dried in an oven. It showed brittle gel fracture under tensile stress but resisted compressive and bending stresses.

Example 40
Ionotropically-crosslinked Non-polysaccharides.

Poly(vinyl acetate) emulsion and aqueous PVOH solutions can be gelled in the presence of sodium tetraborate decahydrate, $Na_2B_4O_7.10\ H_2O$ (Borax). Example 24 was repeated, except that 4 wt % Borax (Aldrich; 22,133-3) solution was chosen as the post-crosslinking medium. The PVOH-containing SPH was placed into Borax solution (4 wt %) for 1 hr after its preparation. SPH modulus was increased in this way.

Example 41
Addition of Glue.

A typical poly(vinyl acetate) emulsion (Glue-All®, Elmer company) can be rapidly gelled in borax solution to a rubber-like material. This glue was diluted with water (volume ratio of 1/3), then added to the AAm SPH formulation (500 μL AAm 50 wt %, 100 μL BIS 1 wt %, 200 μL F127 10 wt %, 50 μL GAA, 50 μL TMEDA 40 v/v % and 50 μL APS 20 wt %) in an amount of 1500 μL before redox addition. SBC (30 mg) was added 45 sec after APS addition. The polymer blend was obtained as a well-structured foam and showed a minor increase in strength (compared to unmodified AAm-based SPH) after 1 hr treatment in Borax solution (10 wt %).

Example 42
Ionotropic Gelation of Acrylic Acid and Polyacrylic Acid: AAm-Based SPH.

Different concentrations (500–1500 μL) of a typical water-soluble polyacrylic acid (Aldrich; 41,600-2; Mw, 250000, 35 wt % solution in water) was incorporated into a AAm superporous formulation. Accordingly, 500 μL AAm (50 wt %), 100 μL BIS (1 wt %), 200 μL F127 (10 wt %), 40 μL AA, 500–1500 μL of PAAc solution, 50 μL of TMEDA (40 v/v %) and 50 μL of APS (20 wt %) were well mixed. The SPH formulation was practiced using 30 mg SBC, which was added 45 sec after APS addition. The well-structured foam was treated with 10 wt % $CaCl_2$ solution. The result was a very high modulus and tough SPH having reduced swelling properties. The higher the PAAc concentration applied, the lower the swelling properties were observed.

Example 43
HEA-Based SPH.

Acrylic acid itself was used to modify swelling properties of HEA-based SPH. 500 μL HEA, 500 μL of DW, 50 μL AAc, 50 μL F127 (10 wt %), 50 μL TMEDA (40 v/v %) and 50 μL APS (20 wt %) were used. SBC (30 mg) was added 4 min after APS addition. A well-structured high modulus SPH foam was obtained after 1 hr treatment in $CaCl_2$ solution (10 wt %).

Example 44
Ionotropic Gelation of AAm and PolyAAm.

Poly(AAm-co-acrylic acid), partial sodium salt containing 80 wt % AAm (Aldrich; 51,147-1) was used as strengthener to improve the gel strength of the PAAm-based SPH. 1500 μL of the solution of this copolymer (7 wt %) was added in PAAm-based SPH formulation (500 μL AAm 50 wt %, 100 μL BIS 1 wt %, 200 μL F127 10 wt %, 50 μL GAA, 50 μL TMEDA 40 v/v % and 50 μL APS 20 wt %). SBC (30 mg) was added 45 sec after APS addition. The foam after synthesis was treated in $FeCl_3$ (10 wt %) solution for 1 hr. Foam extensibility, increased gel strength and resiliency are the features of this kind of treatment.

Example 45

No Modifier/Fe Treatment.

Example 44 was repeated, except no modifier was used and the original SPH foam was treated in FeCl$_3$ solution for 30 min. Gel strength increased but failure occurred in brittle mode.

Example 46

Using a Paper Wet Strengthener.

500 µL of AAm (50 wt %), 500 µL DW, 100 µL BIS (1 wt %), 50 µL F127 (10 wt %), 50 µL AAc, 200 µL PAAE (Hercules; Kymene 557H, as received), 50 µL TMEDA (40 v/v %) and 50 µL APS (20 wt %) were added in order. SBC (30 mg) was added 1.10 min after APS addition. The foam was well structured and put (while in tube) into an oven overnight at the temperature of 70° C. and showed considerable strength. This observation was nearly similar to previous observations with increased crosslinker concentrations of BIS, ethylene glycol dimethacrylate (Aldrich; 33,568-1), and Poly(ethylene glycol) diacrylate (Aldrich; 45,500-8) in SPH formulation. All resulted in a higher modulus product.

Example 47

Thermogelation.

A small amount of homogenized egg white was completely dispersed in monomer solution of AAm-based SPH formulation (500 µL AAm 50 wt %, 100 µL BIS 1 wt %, 200 µL F127 10 wt %, 50 µL GAA, 50 µL TMEDA 40 v/v % and 50 µL APS 20 wt %) before redox addition. Again, a positive effect appeared on the gel compression modulus after that product was heated for 1 hr at the temperature of 80° C.

Example 48

Impregnation with Polyethyleneimine (PEI).

Exploiting the same approach as in the PDADMAC approach, different concentrations of polyethyleneimine (Sigma; P-3143) (50, 25, 10 and 5 wt % in water) were examined as treating medium. First, the base superporous formulation was prepared as 300 µL AAm (50 wt %), 200 µL AAc (50 v/v %), 150 µL NaOH (25 wt %), 500 µL DW, 100 µL BIS (1 wt %), 50 µL F127 (10 wt %), 50 µL TMEDA (40 v/v %) and 50 µL APS (20 wt %). SBC (50 mg) was introduced 2.45 min after APS addition. Prepared SPHs were immersed in PEI solutions for a period of 20 min. The general observations and trends were more or less similar to the PDADMAC approach.

The following modifications can be made on monomer and reacting mixture compositions in order to use them potentially as a base system for preparing elastic, strong SPIHs:

Example 49

Poly(potassium acrylate-co-acrylic acid) hydrogel.

In an attempt to make elastic SPHs based on biocompatible materials, partially hydrolyzed acrylic acid was considered and its hydrogel formation was modified as follows:

500 µL AAc, 200 µL KOH (Aldrich; 22,147-3) (54 wt %), 100 µL BIS (1 wt %), 50 µL F127 (10 wt %), 25 µL TMEDA (40 v/v %), 25 µL SMBS (Aldrich; 16,151-9) (20 wt %) and 50 µL APS (20 wt %) were added in a glass culture tube (100 mm H and 11 mm ID). Based on this formulation, a very strong hydrogel could be prepared through simultaneous application of two reductants and one oxidant for a redox polymerization reaction.

Example 50

Redox Polymerization of Acrylic Acid.

Glacial acrylic acid can be polymerized at room temperature using an ammonium cerium (IV) nitrate, persulfate/bisulfite system as in the following typical formulation. 500 µl AAc (50 v/v %); 1000 µl water; 100 µl PEGDA (Aldrich; 45,500-8) (4.34 wt % in water); 25 µl ammonium cerium (IV) nitrate (Aldrich; 21,547-3), CAN (0.6 g in 6 ml 1N HNO$_3$); 25 µl sodium metabisulfite, SMBS (20 wt %); 25 µl APS (20 wt %). Reaction is instantaneous and the product is a strong hydrogel. The order of addition for the initiating system is CAN, APS and SMBS. This system can be modified using the most compatible modifying systems including CMC (ionotropic gelation) and PVOH (cryogelation). To obtain a hydrogel or superporous hydrogel of high swelling property, it can be further treated with mild neutralizing agents, for example, anhydrous sodium carbonate (Mallinckrodt; 7527) solution (20–30 wt % in water).

Example 51

Poly(HEA-co-DADMAC).

500 µl HEA, 1700 µl water, 100 µl EBA (1.09 wt %), 50 µl TMED (40 v/v %) and 50 µl (20 wt %) were added in a glass culture tube (100 mm H and 11 mm ID). To this formulation, 50–250 µl of DADMAC (65 wt % solution in water; Aldrich; 34,827-9) monomer was added before redox addition. Amount of water used as diluent was correspondingly changed in the range of 1650–1450 µl. According to the results of the mechanical testing (bench comparator, deformation under load), an optimum DADMAC concentration around 12–15 wt % based on monomer can result in a very extensible and strong HEA-based hydrogel.

Example 52

Incorporation of Very High Molecular Weight Dextran as Softener.

500 µl HEA, 1700 µl water, 100 µl EBA (1.09 wt %), 50 µl TMED (40 v/v %) and 50 µl APS (20 wt %) were used as a base formulation. To this, 500 µl of 2 wt % aqueous dextran (Sigma; D-5501) solution was added before redox addition. According to the results of the mechanical testing (deformation under load), softness and extensibility of the HEA-based hydrogel were remarkably improved.

A superporous HEA-based hydrogel was examined using 500 µl of 2 wt % dextran solution. In order to make a major modification, the cryogel technique was applied using PVOH solution. 500 µl HEA, 100 µl EBA (1.09 wt %), 200 µl F127 (10 wt %), 40 µl GAA, 500 µl Dextran (2 wt %), 1000 µl PVOH (6 wt %), 50 µl TMEDA (40 v/v %), 50 µl APS (20 wt %) and 30 mg SBC. SBC was added 2.30 min after APS addition. After an inhibition period of about 3.16 min, the temperature rose to 51° C. in about 2.15 min. A similar formulation was made except using 100 µl of glutaraldehyde solution (20 wt %) as chemical crosslinker. SBC was added 2.0 min after APS addition. Samples were placed into an oven at 75° C. for 2 hr, then frozen in a commercial freezer at −12° C. for 24 hr and thawed at 0° C. for 12 hr. The results are shown in Table 7.

TABLE 7

| | Freezing at −12° C. for 24 hr, Thawing at 0° C. for 12 hr. |
|---|---|
| Hydrogel modified with Dextran and PVOH | About 1.8 times increase in each dimension. Very high strength and low rate of absorption. |
| Hydrogel modified with Dextran, PVOH and Glutaraldehyde | Very high strength in particular at surface (skin strength), low rate of absorption and medium swelling. |

This general formulation can at least be further modified in terms of dextran, glutaraldehyde and PVOH solution concentrations.

Example 53
HEA-based Hydrogel Formation in a Mixed Solvent.

Radical solution polymerization of HEA was studied in mixed solvents of water and EtOH as follows. Increases in ethanol concentration result in softer gel and finally lead to precipitation polymerization. As found, it seems the formulation containing 50/50 ratio of mixed alcohol and water can produce a soft and extensible hydrogel. Given the fact that the CMC and PV6H solutions are completely miscible with the mixed alcohol/water solvent system, this formulation can be tried with CMC and PVOH modifying systems. A typical formulation may be as follows: 250 μl HEA, 250 μl DW, 250 μl EtOH, 200 μl F127 (10 wt %), 100 μl PEGDA (4.34 wt water or in ethyl alcohol), 500 μl CMC (2 wt %), 50 μl TMEDA (40 v/v %), 50 μl APS (20 wt %) and 30 mg SBC. SBC should be added instantaneously.

The present invention has been described hereinabove with reference to certain examples for purposes of clarity and understanding. It should be appreciated that obvious modifications of the present invention can be practiced within the scope of the appended claims.

REFERENCES

The pertinent disclosures of the following references are incorporated herein by reference:

1. Park K., Chen J., and Park H.: Hydrogel composites and superporous hydrogel composites having fast swelling, high mechanical strength and superabsorbent properties. U.S. Pat. No. 6,271,278 2001.
2. Chen J., Park H., and Park K.: Hydrogel foams: A new type of fast swelling hydrogels, *Transactions of Society of Biomaterials* 17: 158, 1994.
3. Chen J., Park H., and Park K.: Synthesis of superporous hydrogels: Hydrogels with fast swelling and superabsorbent properties, *Journal of Biomedical Materials Research* 44: 53–62, 1999.
4. Park K., and Park H.: Super absorbent hydrogel foams, U.S. Pat. No. 5,750,585 1998.
5. Patel V. R., A. M. M.: Preparation and characterization of freeze-dried chitosan—poly(ethylene oxide) hydrogels for site-specific antibiotic delivery in the stomach, *Pharmaceutical Research* 13: 588–593, 1996.
6. Oxley H. R., Corkhill P. H., Fitton J. H., and Tighe B. J.: Macroporous hydrogels for biomedical applications: Methods and morphology, *Biomaterials* 14: 1064–1072, 1993.
7. Kon M., d.V.A.C.: A poly(hema) sponge for restoration of articular cartilage defects, *Plastic and Reconstructive Surgery* 67: 288–294, 1981.
8. Badiger M. V., McNeil M. E., and Graham N. B.: Progens in the preparation of microporous hydrogels based on poly(ethylene oxide), *Biomaterials* 14: 1059–1063, 1993.
9. Bennett D. J., Burford R. P., Davis T. P., and Tilley H. J.: Synthesis of porous hydrogel structure by polymerizing the continuous phase of a microemulsion, *Polymer International* 36: 219–226, 1995.
10. Chirila T. V., Constable I. J., Crowford J., Vijaysekaran S., Thompson D. E., Chen Y. C., and Fletcher W. A.: Poly(2-hydroxyethyl methacrylate) sponges as implant materials: In vivo and in vitro evaluation of celluar invasion, *Biomaterials* 14, 26–36: 1994.
11. Khemani K. C.: Polymeric foams: Science and technology, *ACS Symposium Series, American Chemical Society*, Washington D.C. 239: 1997.
12. Klempner D., and Frisch K. C.: Handbook of polymeric foams and foam technology, Hanser Publishers, Munich, 1991,
13. Spaans C. J., Belgraver V. W., Rienstra O., de Groot J. H., Veth R. P. H., and Pennings A. J.: Solvent-free fabrication of micro-porous polyurethane amide and polyurethane-urea scaffolds for repair and replacement of the knee-joint meniscus, *Biomaterials* 21: 2453–2460, 2000.
14. Elema H., deGroot J. H., and Nijenhuis A. J.: Use of porous biodegradable polymer implants in meniscus reconstruction. 2) biological evaluation of porous biodegradable polymer implants in menisci, *Colloid Polymer Science* 268: 1082–8, 1990.
15. de Groot J. H., Nijenhuis A. J., and Bruin P.: Use of porous biodegradable polymer implants in meniscus reconstruction. 1) preparation of porous biodegradable polyurethanes for the reconstruction of the meniscus, *Colloid Polymer Science* 268: 1073–81, 1990.
16. de Groot J. H., Zijlstra F. M., and Kuijpers H. W.: Meniscal tissue regeneration in porous 50/50 copoly(l-lactide/caprolactone) implants, *Biomaterials* 18: 613–22, 1997.
17. Kim B. S., and Mooney D. J.: Development of biocompatible synthetic extracellular matrices for tissue engineering, *TIBTECH* 16: 224–230, 1998.
18. Griffith L. G.: Polymeric biomaterials, *Acta Materialia* 48: 263–277, 2000.
19. Kang H. W., Tabata Y., and Ikada Y.: Fabrication of porous gelatin scaffolds for tissue engineering, *Biomaterials* 20: 1339–1344, 1999.
20. Bryant S. J., and Anseth K. S.: The effect of scaffold thickness on tissue engineered cartilage in photocrosslinked poly(ethylene oxide) hydrogels, *Biomaterials* 22: 619–626, 2001.
21. Phan D. V., and Trokhan P. D.: Soft absorbent tissue paper containing a biodegradable quarternized amine-ester softening compound and a permanent wet strength resin, U.S. Pat. No. 5,264,082 1993.
22. Gupta D. B., and Granzow R. H.: Process for reconditioning of currency and currency, U.S. Pat. No. 4,421,824 1983.
23. Traubel H., Laas H. J., Reiff H., Konig J., Reiners J., and Faika H.: Process for imparting wet strength to paper, U.S. Pat. No. 6,143,132 2000.
24. Park K., and Omidian H.: Experimental design in the synthesis of polyacrylamide superporous hydrogels, *J. of Bioactive and Compatible Polymers*, Vol. 17(6), 2002.
25. Glicksman M.: Gum technology in the food industry, academic press, 163, 1969.
26. Gombotz W. R., and Wee S. F.: Protein release from alginate matrices, *Advanced Drug Delivery Reviews* 31: 267–285, 1998.
27. Kuo C. K., and Ma P. X.: Ionically crosslinked alginate hydrogels as scaffolds for tissue engineering: Part 1. Structure, gelation rate and mechanical properties, *Biomaterials* 22: 511–521, 2001.
28. Eiselt P., Yeh J., Latvala R. K., Shea L. D., and Mooney D. J.: Porous carriers for biomedical applications based on alginate hydrogels, *Biomaterials* 21: 1921–1927, 2000.
29. Shapiro L., and Cohen S.: Novel alginate sponges for cell culture and transplantation, *Biomaterials* 18: 583–590, 1997.

30. Vorlop K. D., Steinert H. J., and Klein J.: Cell immobilization within coated alginate beads or hollow fibers by ionotropic gelation, *Annals of the New York Academy of Sciences* 501: 339–342, 1987.
31. Hills B. P., Godward J., Debatty M., Barras L., Saturio C. P., and Ouwerx C.: Nmr studies of calcium induced alginate gelation. Part ii. The internal bead structure, *Magnetic Resonance in Chemistry* 38: 719–728, 2000.
32. Duez J. F., Mestdagh M., Demeure R., Goudemant J. F., Hills B. P., and Godward J.: Nmr studies of calcium-induced alginate gelation. Part 1—mri tests of gelation models, *Magnetic Resonance in Chemistry* 38: 324–330, 2000.
33. LeRoux M. A., Guilak F., and Setton L. A.: Compressive and shear properties of alginate gel: Effects of sodium ions and alginate concentration, *Journal of Biomedical Materials Research* 47: 46–53, 1999.
34. Kulkarni A. R., Soppimath K. S., and Aminabhavi T. M.: Controlled release of diclofenac sodium from sodium alginate beads crosslinked with glutaraldehyde, *Pharmaceuica Acta Helvetiae* 74: 29–36, 1999.
35. Ostberg T., Vesterhus L., and Graffner C.: Calcium alginate matrices for oral multiple-unit administration. 2. Effect of process and formulation factors on matrix properties, *International Journal of Pharmaceutics* 97: 183–193, 1993.
36. Pillay V., Dangor C. M., Govender T., Moopanar K. R., and Hurbans N.: Drug release modulation from cross-linked calcium alginate microdiscs, 2: Swelling, compression, and stability of the hydrodynamically-sensitive calcium alginate matrix and the associated drug release mechanisms, *Drug Delivery* 5: 35–46, 1998.
37. Pillay V., Dangor C. M., Govender T., Moopanar K. R., and Hurbans N.: Ionotropic gelation: Encapsulation of indomethacin in calcium alginate gel discs, *Journal of Microencapsulation* 15: 215–226, 1998.
38. Pillay V., and Fassihi R.: In vitro release modulation from crosslinked pellets for site-specific drug delivery to the gastrointestinal tract—i. Comparison of ph-responsive drug release and associated kinetics, *Journal of Controlled Release* 59: 229–242, 1999.
39. Kulkarni A. R., Soppimath K. S., Aminabhavi T. M., Dave A. M., and Mehta M. H.: Glutaraldehyde crosslinked sodium alginate beads containing liquid pesticide for soil application, *Jounal of Controlled Release* 63: 97–105, 2000.
40. Kim Y. J., Yoon K. J., and Ko S. W.: Preparation and properties of alginate superabsorbent filament fibers crosslinked with glutaraldehyde, *Journal of Applied Polymer Science* 78: 1797–1804, 2000.
41. Tripathy T., Pandey S. R., Karmakar N. C., Bhagat R. P., and Singh R. P.: Novel flocculating agent based on sodium alginate and acrylamide, *European Polymer Journal* 35: 2057–2072, 1999.
42. Kim S. R., Yuk S. H., and Jhon M. S.: A semi-interpenetrating network system for a polymer membrane, *European Polymer Journal* 33: 1009–1014, 1997.
43. Wang X. P.: Preparation of crosslinked alginate composite membrane for dehydration of ethanol-water mixtures, *Journal of Applied Polymer Science* 77: 3054–3061, 2000.
44. Hertzberg S., Moen E., Vogelsang C., and Ostgaard K.: Mixed photo-crosslinked poly(vinyl alcohol) and calcium-alginate gels for cell entrapment, *Applied Microbiology and Biotechnology* 43: 10–17, 1995.
45. Omidian H.: Elastic Superporous Hydrogels, Purdue University, Industrial and Physical Pharmacy, Research Report, 2001.
46. Scherr G. H.: Alginate foam products, U.S. Pat. No. 5,718,916 1998.
47. Shu X., and Zhu K. J.: A novel approach to prepare tripolyphosphate/chitosan complex beads for controlled release drug delivery, *International Journal of Pharmaceutics* 201: 51–58, 2000.
48. Kumar M. N. V. R.: A review of chitin and chitosan applications, *Reactive & Functional Polymers* 46: 1–27, 2000.
49. Lee S. T., Mi F. L., Shen Y. J., and Shyu S. S.: Equilibrium and kinetic studies of copper(ii) ion uptake by chitosan-tripolyphosphate chelating resin, *Polymer* 42: 1879–1892, 2001.
50. Aral C., and Akbuga J.: Alternative approach to the preparation of chitosan beads, *International Journal of Pharmaceutics* 168: 9–15, 1998.
51. Aydin Z., and Akbuga J.: Chitosan beads for the delivery of salmon calcitonin: Preparation and release characteristics, *International Journal of Pharmaceutics* 131: 101–103, 1996.
52. Dureja H., Tiwary A. K., and Gupta S.: Simulation of skin permeability in chitosan membranes, *International Journal of Pharmaceutics* 213: 193–198, 2001.
53. Shu X. Z., and Zhu K. J.: Chitosan/gelatin microspheres prepared by modified emulsification and ionotropic gelation, *Journal of Microencapsulation* 18: 237–245, 2001.
54. Lim L. Y., Wan L. S. C., and Thai P. Y.: Chitosan microspheres prepared by emulsification and ionotropic gelation, *Drug Development and Industrial Pharmacy* 23: 981–985, 1997.
55. Long D. D., and vanLuyen D.: Chitosan-carboxymethylcellulose hydrogels as supports for cell immobilization, *Journal of Macromolecular Science—Pure and Applied Chemistry* A33: 1875–1884, 1996.
56. Mi F. L., Shyu S. S., Lee S. T., and Wong T. B.: Kinetic study of chitosan-tripolyphosphate complex reaction and acid-resistive properties of the chitosan-tripolyphosphate gel beads prepared by in-liquid curing method, *Journal of Polymer Science, Part B—Polymer Physics* 37: 1551–1564, 1999.
57. Overgaard S., Scharer J. M., Mooyoung M., and Bols N. C.: Immobilization of hybridoma cells in chitosan alginate beads, *Canadian Journal of Chemical Engineering* 69: 439–443, 1991.
58. Sezer A. D., and Akbuga J.: Release characteristics of chitosan treated alginate beads: I. Sustained release of a macromolecular drug from chitosan treated alginate beads, *Journal of Microencapsulation* 16: 195–203, 1999.
59. Sezer A. D., and Akbuga J.: Release characteristics of chitosan treated alginate beads: Ii. Sustained release of a low molecular drug from chitosan treated alginate beads, *Journal of Microencapsulation* 16: 687–696, 1999.
60. Wan L. S. C., Lim L. Y., and Soh B. L.: Drug-release from chitosan beads, *STP Pharma Sciences* 4: 195–200, 1994.
61. Wu F. C., Tseng R. L., and Juang R. S.: Enhanced abilities of highly swollen chitosan beads for color removal and tyrosinase immobilization, *Journal of Hazardous Materials* 81: 167–177, 2001.
62. Glicksman M.: Gum technology in the food industry, academic press, 412, 1969.
63. Glicksman M.: Gum technology in the food industry, academic press, 415, 1969.
64. Prasad M. P., and Kalyanasundaram M.: Scanning electron microscopic analysis and swelling behaviour of ionotropically crosslinked carboxymethylcellulose and carboxymethylcellulose-gelatin matrices, *Carbohydrate Polymers* 26: 35–41, 1995.
65. Prasad M. P., and Kalyanasundaram M.: Iron (iii) carboxymethylcellulose as swellable erodible matrix for the controlled release of a mosquito larvicide, *Journal of Controlled Release* 22: 167–172, 1992.
66. Yakup Arica, M.: Immobilization of polyphenol oxidase on carboxymethylcellulose hydrogel beads: Preparation and characterization, *Polymer International* 49: 775–781, 2000.

67. Prasad M. P., and Kalyanasundaram M.: Effect of incorporation of gelatin, an interactive polymer on the matrix stability and release of fenthion from crosslinked matrices of carboxymethylcellulose, *Journal of Controlled Release* 27: 219–225, 1993.
68. Prasad M. P., and Kalyanasundaram M.: Ionotropic crosslinking of sodium carboxymethylcellulose and sodium carboxymethylcellulose-gelatin matrices and their errosion properties, *Journal of Applied Polymer Science* 49: 2075–2079, 1993.
69. Glicksman M.: Gum technology in the food industry, academic press, 165, 1969.
70. Pillay V., and Fassihi R.: In vitro release modulation from crosslinked pellets for site-specific drug delivery to the gastrointestinal tract—ii. Physicochemical characterization of calcium-alginate, calcium-pectinate and calcium-alginate-pectinate pellets, *Journal of Controlled Release* 59: 243–256, 1999.
71. Sungthongjeen S., Pitaksuteepong T., Somsiri A., and Sriamornsak P.: Studies on pectins as potential hydrogel matrices for controlled-release drug delivery, *Drug Development and Industrial Pharmacy* 25: 1271–1276, 1999.
72. Sriamornsak P., and Nunthanid J.: Calcium pectinate gel beads for controlled release drug delivery: Ii. Effect of formulation and processing variables on drug release, *Journal of Microencapsulation* 16: 303–313, 1999.
73. Sriamornsak P., and Nunthanid J.: Calcium pectinate gel beads for controlled release drug delivery: I. Preparation and in vitro release studies, *International Journal of Pharmaceutics* 160: 207–212, 1998.
74. Aydin Z., and Akbuga J.: Preparation and evaluation of pectin beads, *International Journal of Pharmaceutics* 137: 133–136, 1996.
75. Sriamornask P.: Investigation of pectin as a carrier for oral delivery of proteins using calcium pectinate gel beads, *International Journal of Pharmaceutics* 169: 213–220, 1998.
76. Sriamornsak P.: Effect of calcium concentration, hardening agent and drying condition on release characteristics of oral proteins from calcium pectinate gel beads, *European Journal of Pharmaceutical Sciences* 8: 221–227, 1999.
77. Sriamornsak P., and Nunthanid J.: Preliminary investigation of some polysaccharides as a carrier for cell entrapment, *European Journal of Pharmaceutics and Biopharmaceutics* 46: 233–236, 1998.
78. Lozinsky V. I., and Plieva F. M.: Poly(vinyl alcohol) cryogels employed as matrices for cell immobilization. 3. Overview of recent research and developments, *Enzyme and Microbial Technology* 23: 227–242, 1998.
79. Damshkaln L. G., Simenel I. A., and Lozinsky V. I.: Study of cryostructurization of polymer systems. Xv. Freeze-thaw-induced formation of cryoprecipitate matter from low-concentrated aqueous solutions of poly(vinyl alcohol), *Journal of Applied Polymer Science* 74: 1978–1986, 1999.
80. Lozinsky V. I., and Damshkaln L. G.: Study of cryostructurization of polymer systems. Xvii. Poly(vinyl alcohol) cryogels: Dynamics of the cryotropic gel formation, *Journal of Applied Polymer Science* 77: 2017–2023, 2000.
81. Hassan C. M., and Peppas N. A.: Cellular pva hydrogels produced by freeze/thawing, *Journal of Applied Polymer Science* 76: 2075–2079, 2000.
82. Hassan C. M., and Peppas N. A.: Structure and applications of poly(vinyl alcohol) hydrogels produced by conventional crosslinking or by freezing/thawing methods, *Advances in Polymer Science* 153: 37–65, 2000.
83. Hassan C. M., and Peppas N. A.: Structure and morphology of freeze/thawed pva hydrogels, *Macromolecules* 33: 2472–2479, 2000.
84. Lozinsky V. I., and Damshkaln L. G.: Cryotropic gelation of poly(vinyl alcohol) solutions, *Uspekhi Khimi* 67: 641–655, 1998.
85. Lozinsky V. I., Zubov A. L., and Titova E. F.: Swelling behavior of poly(vinyl alcohol) cryogels employed as matrices for cell immobilization, *Enzyme and Microbial Technology* 18: 561–569, 1996.
86. Lozinsky V. I., Zubov A. L., Kulakova V. K., Titova E. F., and Rogozhin S. V.: Study of cryostructurization of polymer systems. 9. Poly(vinyl alcohol) cryogels filled with particles of crosslinked dextran gel, *Journal of Applied Polymer Science* 44: 1423–1435, 1992.
87. Lozinsky V. I., Solodova E. V., Zubov A. L., and Simenel I. A.: Study of cryostructurization of polymer systems. 11.The formation of pva cryogels by freezing-thawing the polymer aqueous solutions containing additives of some polyols, *Journal of Applied Polymer Science* 58: 171–177, 1995.
88. Lozinsky V. I., Zubov A. L., Savina I. N., and Plieva F. M.: Study of cryostructurization of polymer systems. Xiv. Poly(vinyl alcohol) cryogels: Apparent yield of the freeze-thaw-induced gelation of concentrated aqueous solutions of the polymer, *Journal of Applied Polymer Science* 77: 1822–1831, 2000.
89. Lozinsky V. I., Domotenko L. V., Zubov A. L., and Simenel I. A.: Study of cryostructurization of polymer systems .12. Poly(vinyl alcohol) cryogels: Influence of low-molecular electrolytes, *Journal of Applied Polymer Science* 61: 1991–1998, 1996.
90. Hassan C. M., Stewart J. E., and Peppas N. A.: Diffusional characteristics of freeze/thawed poly(vinyl alcohol) hydrogels: Applications to protein controlled release from multilaminate devices, *European Journal of Pharmaceutics and Biopharmaceutics* 49: 161–165, 2000.
91. Kramer G., Buchhammer H. M., and Lunkwitz K.: Investigation of the stability of surface modification by polyelectrolyte complexes—influence of polyelectrolyte complex components and of substrates and media, *Colloids and Surfaces A—Physicochemical and Engineering Aspects* 137: 45–56, 1998.
92. Kramer G., Buchhammer H. M., and Lunkwitz K.: Surface modification by polyelectrolyte complexes: Influence of modification procedure, polyelectrolyte components, and substrates, *Journal of Applied Polymer Science* 65: 41–50, 1997.
93. Kramer G., Buchhammer H. M., and Lunkwitz K.: Surface modification by polyelectrolyte complexes: Influence of different polyelectrolyte components and substrates, *Colloids and Surfaces A—Physicochemical and Engineering Aspects* 122: 1–12, 1997.
94. Dan Y., and Wang Q.: Studies on viscosity enhancement of p(am-aa)/p(am-dmdaac) complex used as polymer flooding agent, *Chemical Journal of Chinese Universities—Chinese* 18: 818–822, 1997.
95. Dan Y., and Wang Q.: Homogeneous complex solution formed through interpolyelectrolyte complexation of poly (acrylamide-acrylic acid) with poly(acrylamide-dimethyldiallylammonium chloride) in aqueous media, *Polymer International* 49: 551–560, 2000.
96. Wang Q., Dan Y., and Wang X. G.: A new polymer flooding agent prepared through intermacromolecular complexation, *Journal of Macromolecular Science—Pure and Applied Chemistry* A34: 1155–1169, 1997.
97. Aizawa K.: Elastomeric polyacrylamide gels for high-resolution electrophoresis of proteins, *Polymers for Advanced Technologies* 11: 481–487, 2000.
98. T. Tanaka and D. J. Fillmore, "Kinetics of swelling of gels," *Journal of Chemical Physics*, vol. 70, pp. 1214–1218, 1979.
99. V. A. Stoy, "New type of hydrogel for controlled drug delivery," *Journal of Biomaterials Applications*, vol. 3, pp. 553–605, 1989.

100. J. Chen, W. E. Blevins, H. Park, and K. Park, "Gastric retention properties of superporous hydrogel composites," *Journal of Controlled Release*, vol. 64(1–4), pp. 39–51, 2000.
101. G. A. Agyilirah, M. Green, R. DuCret, and G. S. Banker, "Evaluation of the gastric retention properties of a cross-linked polymer coated tablet versus those of a non-disintegrating tablet," *International Journal of Pharmaceutics*, vol. 75, pp. 241, 1991.
102. M. Ichikawa, S. Watanabe, and Y. Miyake, "A new multiple-unit oral floating dosage system. I: Preparation and in vitro evaluation of floating and sustained-release characteristics," *Journal of Pharmaceutical Sciences*, vol. 80, pp. 1062, 1991.
103. M. Ichikawa, T. Kato, M. Kawahara, S. Watanabe, and M. Kayano, "A new multiple-unit oral floating dosage system. II: In vivo evaluation of floating and sustained-release characteristics with p-aminobenzoic acid and isosorbide dinitrate as model drugs," *Journal of Pharmaceutical Sciences*, vol. 80, pp. 1153, 1991.
104. A. K. Hilton and P. B. Deasy, "In vitro and in vivo evaluation of an oral sustained-release floating dosage form of amoxicillin trihydrate," *International Journal of Pharmaceutics*, vol. 86, pp. 79–88, 1992.
105. D. R. Swanson, B. L. Barclay, P. S. Wong, and F. Theeuwes, "Nifedipine gastrointestinal therapeutic system," *American Journal of Medicine*, vol. 83, pp. 3–9, 1987.
106. S. Bolton and S. Desai, Floating sustained release therapeutic compositions, U.S. Pat. No. 4,814,179 1989.
107. V. S. Gerogiannis, D. M. Rekkas, P. P. Dallas, and N. H. Choulis, "Floating and swelling characteristics of various excipients used in controlled release technology," *Drug Development and Industrial Pharmacy*, vol. 19, pp. 1061–1081, 1993.
108. M. R. Franz and M. P. Oth, "Sustained release bilayer buoyant dosage form," U.S. Pat. No. 5,232,704, 1993.
109. H. Yuasa, Y. Takashima, and Y. Kanaya, "Studies on the development of intragastric floating and sustained release preparation. Part 1. Application of calcium silicate as a floating carrier," *Chemical and Pharmaceutical Bulletin*, vol. 44, pp. 1361–1366, 1996.
110. K. Park and J. R. Robinson, "Bioadhesive polymers as platforms for oral controlled drug delivery: method to study bioadhesion," *International Journal of Pharmaceutics*, vol. 19, pp. 107–127, 1984.
111. H. Park and J. R. Robinson, "Physico-chemical properties of water insoluble polymers important to mucin/epithelial adhesion," *Journal of Controlled Release*, vol. 2, pp. 47–57, 1985.
112. N. A. Peppas, G. Ponchel, and D. Duchene, "Bioadhesive analysis of controlled release systems. Part 2. Time dependent bioadhesive stress in poly(acrylic acid) containing systems," *Journal of Controlled Release*, vol. 5, pp. 143–149, 1987.
113. Y. Lee and Y. W. Chien, "Oral mucosa controlled delivery of LHRH by bilayer mucoadhesive polymer systems," *Journal of Controlled Release*, vol. 37, pp. 251–261, 1995.
114. N. A. Peppas and J. R. Robinson, "Bioadhesives for optimization of drug delivery," *Journal of Drug Targeting*, vol. 3, pp. 183–184, 1995.
115. A. Jayakrishnan, M. Mohanty, R. Mandalam, V. R. K. Rao, A. K. Gupta, and S. Joseph, "Endovascular emoblization using hydrogel microspheres," *Journal of Materials Science: Materials in Medicine*, vol. 5, pp. 729–727, 1994.
116. D. J. Martinelli, S. Wadler, C. W. Bakal, J. Cynamon, A. Rozenblit, H. Haynes, R. Kaleya, and P. H. Wiernik, "Utility of Embolization or Chemoembolization As 2nd-Line Treatment in Patients With Advanced or Recurrent Colorectal-Carcinoma," *Cancer*, vol. 74, pp. 1706–1712, 1994.
117. C. Tellez, A. B. Benson, M. T. Lyster, M. Talamonti, J. Shaw, M. A. Braun, A. A. Nemcek, and R. L. Vogelzang, "Phase II trial of chemoembolization for the treatment of metastatic colorectal carcinoma to the liver and teview of the literature," *Cancer*, vol. 82, pp. 1250–1259, 1998.
118. K. Park, "Superporous Hydrogels for Pharmaceutical & Other Applications," *Drug Delivery Technology*, vol. 2, pp. 38–44, 2002.
119. F. A. Dorkoosh, J. Brussee, J. C. Verhoef, G. Borchard, M. Rafiee-Tehrani, and H. E. Junginger, "Preparation and NMR characterization of superporous hydrogels (SPH) and SPH composites," *Polymer*, vol. 41(23), pp. 8213–8220, 2000.
120. F. A. Dorkoosh, J. C. Verhoef, G. Borchard, M. Rafiee-Tehrani, and H. E. Junginger, "Development and characterization of a novel peroral peptide drug delivery system," *Journal of Controlled Release*, vol. 71, pp. 307–318, 2001.
121. F. A. Dorkoosh, J. C. Verhoef, M. H. Ambagts, M. Rafiee-Tehrani, G. Borchard, and H. E. Junginger, "Peroral delivery systems based on superporous hydrogel polymers: release characteristics for the peptide drugs buserelin, octreotide and insulin," *European Journal of Pharmaceutical Sciences*, vol. 15, pp. 433–439, 2002.

What is claimed is:

1. A method of forming a hydrogel material having enhanced mechanical strength properties comprising:
   (i) combining at least one ethylenically-unsaturated monomer and a multi-olefinic crosslinking agent to form an admixture thereof;
   (ii) subjecting the admixture to polymerization conditions, optionally further subjecting the admixture to foaming conditions substantially concurrent therewith, effective to form a hydrogel composite thereof;
   (iii) combining at least one strengthening agent with the admixture prior to or after performing step (ii) so that said hydrogel composite contains said at least one strengthening agent; and
   (iv) subjecting the hydrogel composite containing strengthening agent to strengthening conditions effective to afford the hydrogel material having enhanced strength properties, wherein said strengthening conditions entail (a) contacting the hydrogel composite with a chemical strengthening agent selected from at least one of an ionotropic gellation agent, a polyphenolic complexing agent, an acid, a latex compound, and a glue, or (b) cryogellation conditions.

2. The method of claim 1, wherein said admixture is subjected to foaming conditions in step (ii), thereby affording a strengthened superporous hydrogel.

3. The method of claim 1, wherein the strengthening agent is combined with said admixture prior to performing step (ii).

4. The method of claim 1, wherein the at least one ethylenically-unsaturated monomer is selected from (meth)acrylic acid, salts of (meth)acrylic acid, esters of (meth)acrylic acid and hydroxyl derivatives thereof, itaconic acid, salts and acids of esters of (meth)acrylic acid, amides of (meth)acrylic acid, N-alkyl amides of (meth)acrylic acid, salts and acids of N-alkyl amides of(meth)acrylic acid, N-vinyl pyrrolidone, (meth)acrylamide, N-alkyl derivatives of (meth)acrylamide, alkyl ammonium salts, N-alkyl derivatives of an alkyl (meth)acrylate, 2-acrylamido-2-methyl-1-propanesulfonic acid, potassium salt of 3-sulfopropyl acrylate, and 2-(acryloyloxy)ethyl trimethyl ammonium methyl sulfate.

5. The method of claim 4, wherein the ethylenically-unsaturated monomer is selected from acrylamide (AAm), N-isopropyl acrylamide (NIPAM), 2-hydroxyethyl (meth) acrylate (HEA, HEMA), acrylic acid (AAc), salts of acrylic acid (potassium, sodium and ammonium), potassium salt of 3-sulfopropyl acrylate (SPAK), poly(ethylene glycol) acrylate, poly(ethylene glycol)alkyl ether acrylate, methacrylic acid-2-dimethylaminoethyl ester, dimethylaminoethyl acrylate and diallyldimethylammonium chloride (DADMAC).

6. The method of claim 1, wherein the crosslinking agent is selected from the group consisting of N,N'-methylenebisacrylamide (BIS), N,N'-ethylenebisacrylamide (EBA), (poly)ethylene glycol di(meth)acrylate, ethylene glycol diglycidyl ether, glycidyl methacrylate, polyamidoamine epichlorohydrin resin, trimethylolpropane triacrylate (TMPTA), piperazine diacrylamide, glutaraldehyde, epichlorohydrin, crosslinkers containing 1,2-diol structures, and functionalized peptides and proteins.

7. The method of claim 1, wherein the at least one strengthening agent is a monomer, polymer, or polyphenolic complexing agent.

8. The method of claim 7, wherein the monomer is an amino acid.

9. The method of claim 7, wherein the polymer is a polysaccharide selected from the group consisting of alginate and derivatives thereof, chitins, chitosan and derivatives thereof, cellulose and derivatives thereof, starch and derivatives thereof, cyclodextrin, dextran and derivatives thereof, gums, lignins, pectins, saponins, deoxyribonucleic acids, and ribonucleic acids.

10. The method of claim 7, wherein the polymer is a polypeptide or protein selected from the group consisting of albumin, bovine serum albumin, casein, collagen, fibrinogen, gelatin and derivatives thereof, gliadin, sodium glycine carbonate, bacterial cell membrane enzymes, and poly(amino acids).

11. The method of claim 10, wherein the poly(amino acid) is selected from polyproline, poly(L-arginine), poly(L-lysine), polysarcosine, poly(L-hydroxyproline), poly(glutamic acid), poly(S-carboxymethyl-L-cysteine), and poly(aspartic acid).

12. The method of claim 7, wherein the polymer is a homo- or co-polymer comprised of a monomer selected from the group consisting of acrolein potassium, (meth)acrylamides, (meth)acrylic acid and salts thereof, (meth)acrylates, acrylonitrile, ethylene, ethylene glycol, ethyleneimine, ethyleneoxide, styrene sulfonate, vinyl acetate, vinyl alcohol, vinyl chloride, and vinylpyrrolidone.

13. The method of claim 7, wherein the polyphenolic complexing agent is selected from the group consisting of gallotannins, ellagitannins, taragallotannins, caffetannins, proanthocyanidins, catechin, epicatechin, chlorogenic acid, and arbutin.

14. The method of claim 1, wherein the at least one strengthening agent is selected from natural and synthetic polyelectrolytes, and neutral, hydrophilic polymers.

15. The method of claim 14, wherein the at least one strengthening agent is selected from the group consisting of sodium carboxymethylcellulose, sodium starch glycolate, sodium carboxymethyl starch, dextran, dextran sulfate, chitosan, xanthan, gellan, hyaluronic acid, sodium alginate, pectinic acid, deoxyribonucleic acids, ribonucleic acid, gelatin, albumin, polyacrolein potassium, sodium glycine carbonate, poly(acrylic acid) and its salts, polyacrylonitrile, polyacrylamide, poly(styrene sulfonate), poly(aspartic acid), polylysine, polyvinylpyrrolidone, polyvinyl alcohol, CARBOPOL, ultramylopectin, poly(ethylene glycol), neutral cellulose derivatives, microcrystalline cellulose, powdered cellulose, cellulose fibers, and starch.

16. The method of claim 1, wherein the ionotropic gellation agent is selected from calcium chloride, cupric sulfate, ammonium cerium (IV) nitrate, ferric chloride hexahydrate, sodium tetraborate decahydrate, zinc chloride, aluminum chloride hexahydrate, chromium chloride, and pentasodium tripolyphosphate.

17. The method of claim 1, wherein the polyphenolic complexing agent is selected from the group consisting of gallotannins, ellagitannins, taragallotannins, caffetannins, proanthocyanidins, catechin, epicatechin, chlorogenic acid, and arbutin.

18. The method of claim 1, wherein the cryogellation conditions comprise applying a freeze-thaw cycle on PVOH and the hydrogel composite.

19. A strengthened hydrogel or superporous hydrogel formed by the method of claim 1.

20. The superporous hydrogel of claim 19 having an average pore size of about 1 $\mu$m to about 5000 $\mu$m.

21. The superporous hydrogel of claim 20, wherein the average pore size is about 10 $\mu$m to about 3000 $\mu$m.

22. The superporous hydrogel of claim 19, wherein the relative compression strength of the superporous hydrogel is at least 50-fold greater than the compression strength of a superporous hydrogel absent said strengthening agent.

23. The superporous hydrogel of claim 19, wherein the tensile strength at breaking point of the strengthened superporous hydrogel is at least about 2.0 kPa.

24. The superporous hydrogel of claim 19, wherein the equilibrium volume swelling ratio of the strengthened superporous hydrogel is in the range of about 8 to about 18.

25. A pharmaceutical composition in solid dosage form comprising a pharmacologically effective dose of a drug and a strengthened hydrogel or superporous hydrogel made by the method of claim 1.

26. The pharmaceutical composition of claim 25, wherein the strengthened hydrogel or superporous hydrogel contains at least one strengthening agent selected from alginate, chitosan, carboxymethyl cellulose, tannic acid, and gelatin.

27. The pharmaceutical composition of claim 25, which is in tablet, capsule, or particulate form.

28. The pharmaceutical composition of claim 25, which is a tablet or capsule formed by a molding, direct compression, or press coating compression technique.

* * * * *